(12) United States Patent
De Jonghe et al.

(10) Patent No.: US 9,822,127 B2
(45) Date of Patent: Nov. 21, 2017

(54) GAK MODULATORS AS ANTIVIRALS

(71) Applicants: Katholieke Universiteit Leuven, Leuven (BE); The Board of Trustees of the Leland Stanford Junior University, Stanford, CA (US)

(72) Inventors: Steven De Jonghe, Tervuren (BE); Piet Herdewyn, Heverlee (BE); Elena Bekerman, Castro Valley, CA (US); Shirit Einav, Los Altos Hills, CA (US); Gregory Neveu, Lyons (FR)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days.

(21) Appl. No.: 15/327,568

(22) PCT Filed: Jul. 23, 2015

(86) PCT No.: PCT/EP2015/066864
§ 371 (c)(1),
(2) Date: Jan. 19, 2017

(87) PCT Pub. No.: WO2016/012536
PCT Pub. Date: Jan. 28, 2016

(65) Prior Publication Data
US 2017/0152271 A1 Jun. 1, 2017

(30) Foreign Application Priority Data

Jul. 23, 2014 (GB) .................................. 1413013.2
Feb. 27, 2015 (GB) .................................. 1503288.1

(51) Int. Cl.
*C07D 513/04* (2006.01)
*A61K 31/4365* (2006.01)
*C07D 519/00* (2006.01)

(52) U.S. Cl.
CPC ......... *C07D 513/04* (2013.01); *C07D 519/00* (2013.01)

(58) Field of Classification Search
CPC .......................... C07D 513/04; A61K 31/4365
See application file for complete search history.

(56) References Cited

U.S. PATENT DOCUMENTS

| 9,221,822 B2 * | 12/2015 | Herdewijn ........... A61K 31/519 |
| 9,518,066 B2 | 12/2016 | Herdewijn et al. |
| 2001/0007867 A1 | 7/2001 | Chen et al. |

FOREIGN PATENT DOCUMENTS

| WO | 2007/015866 A2 | 2/2007 |
| WO | 2015/001076 A1 | 1/2015 |

OTHER PUBLICATIONS

PCT/EP2015/066864 International Search Report.
PCT/EP2015/066864 Written Opinion of the International Search Authority.
Taurins et al. (1973) Isothiazolopyridines. 1. Synthesis and Spectra of Isothiazolo[3,4-b],3-Aminoisothiazolo[5,4-b] and 3-Methylisothiazolo[5,4-c]pyridines. Preparation and Spectra of Some 2,3- and 3,4-Disubstituted Pyridines. Canadian Journal of Chemistry 51:1741-1748.
Gewald et al. (1979) Synthese and Reaktionen von 4-Aminoisothiazolen. Liebigs Annalen der Chemie 1979: p. 1537, compounds 12a, 12b, 12c, 13.

\* cited by examiner

*Primary Examiner* — Golam M M Shameem
(74) *Attorney, Agent, or Firm* — Jenny Buchbinder

(57) ABSTRACT

The present invention relates to the use of a class of novel isothiazolo[4,3-b]pyridine derivatives as well as to pharmaceutical compositions comprising one or more of said isothiazolo[4,3-b]pyridine derivatives and one or more pharmaceutically acceptable excipients as biologically active ingredients, more specifically as medicaments for the treatment of disorders and pathologic conditions such as viral diseases.

4 Claims, 3 Drawing Sheets

GAK MODULATORS AS ANTIVIRALS

FIELD OF THE INVENTION

The present invention relates to the use of a class of novel isothiazolo[4,3-b]pyridine derivatives as well as to pharmaceutical compositions comprising one or more of said isothiazolo[4,3-b]pyridine derivatives and one or more pharmaceutically acceptable excipients as biologically active ingredients, more specifically as medicaments for the treatment of disorders and pathologic conditions such as viral diseases.

BACKGROUND OF THE INVENTION

The ubiquitously expressed kinase GAK (cyclin G-associated kinase, also known as auxillin 2) is a 160 kDa serine/threonine protein kinase that was first identified as a cyclin G1-binding protein. GAK is composed of a N-terminal kinase domain that phosphorylates the µ-subunits of adaptor proteins 1 and 2, a clathrin binding domain, and a C-terminal J-domain that interacts with a heat shock cognate 70 (Hsc70).

As suggested by its strong homology (43%) to the neuronal-specific protein auxilin, a heat shock cognate 70 (Hsc70) cochaperone with a role in uncoating clathrin vesicles, GAK regulates clathrin-mediated membrane trafficking as an essential cofactor for the Hsc70-dependent uncoating of clathrin-coated vesicles. Moreover, down-regulation of GAK by a small hairpin RNA enhanced the levels of expression and tyrosine kinase activity of EGFR and altered the spectrum of downstream signaling, at least partly due to alterations in receptor trafficking.

GAK forms a complex with Cyclin G and the protein phosphatase 2A (PP2A) B'γ subunit, which suggests that it may play yet unidentified roles in cellular events other than membrane trafficking. In support of this hypothesis, GAK acts as a transcriptional coactivator of the androgen receptor (AR; a ligand-dependent transcription factor), and GAK expression was significantly increased in hormone refractory prostate cancer. Moreover, both GAK and its association partner clathrin heavy chain (CHC), localize to both the cytoplasm and nucleus with distinct association modes, and CHC colocalizes with GAK in the nucleus, while Cyclin G and PP2A B'γ are also present in the nucleus.

Moreover, siRNA-mediated GAK knockdown caused cell-cycle arrest at metaphase, which revealed two novel functions of GAK: maintenance of proper centrosome stability and of mitotic chromosome congression.

High-throughput screening of the kinome is a powerful tool with which one can identify multiple kinases related to the survival of cancer cells. Kinase shRNA screening revealed that the loss of function of GAK, among others, resulted in marked growth inhibition of osteosarcoma cells (*Mol. Cancer Ther.* 2010, 9 (12), 3342-3350).

In contrast to the high expression of GAK in osteosarcomas, normal human osteoblasts expressed only low quantity of the protein. The result of kinase shRNA screening was further confirmed by siRNA knockdown of GAK on several osteosarcoma cell lines. Although 100 nmol/L of nonspecific siRNA did not have any cytotoxic activity on osteosarcoma cell lines, a concentration of as low as 10 nmol/L of GAK siRNA was enough to inhibit the proliferation of osteosarcoma cells. Importantly, it had similar effects on both drug-sensitive and drug-resistant osteosarcoma cell lines, which implicate that it exerts its effects independently of ATP-binding cassette transporters such as P-gp. This was further confirmed by Western blot analysis of P-gp, which did not show any effect on Pgp trafficking. Therefore, GAK has the potential to be a target for the treatment of drug-naive osteosarcomas as well as multidrug-resistant osteosarcomas.

In addition, recent genome wide association studies (GWAS) have been performed to identify genetic risk factors in sporadic, non-familial forms of disease. The GWAS showed an association for a few genes previously identified in the linkage studies (alpha-synuclein, LRRK2) and also identified new genetic risk factors for Parkinson's disease, such as glucocerebrosidase (GBA), microtubule associated protein tau (MAPT), PARK16, the human leukocyte antigen (HLA) locus, bone marrow stromal antigen 1 (BST1) and GAK (*The Application of Clinical Genetics* 2011, 4, 67-80). GAK has been labeled as the PARK17 gene. Later studies confirmed an association between Parkinson's disease and GAK (*Hum. Genet.* 2009, 124, 593-605; *Nature Genet.* 2010, 42, 781-785; *Hum. Mol. Genet.* 2011, 20, 345-353; *Neurology* 2012, 79, 659-667; *Ann. Hum. Genet.* 2011, 75, 195-200). A systematic meta-analysis in Parkinson's disease genetics confirms overall probability values showing robust association of genetic markers in the GAK gene with Parkinson's disease (*PLoS Genet.* 2012, 8, e1002548). Therefore, multiple genetic studies confirm a role for GAK in Parkinson's disease.

Hypoxia induces changes to cancer cells that facilitate their survival, make them more resistant to classical drug treatments and increases the metastatic potential of tumor cells. Researchers from Wyeth have therefore carried out a kinome wide siRNA screening in order to identify kinase genes that affect hypoxic colon cancer cells (*J Biomol Screen.* 2013 18, 782-796.). Hits identified in the screen were characterized for effects on different molecular responses to hypoxia. The hits were validated by short hairpin RNA studies. These studies led to the observation that GAK plays in important role in the adaptation of cancer cells to hypoxia. Therefore, GAK can be considered as a promising drug target for the treatment of cancer cells within the hypoxic regions of a solid tumor.

GAK phosphorylates the µ-subunits of adaptor proteins 1 and 2, which are membrane trafficking proteins. AP2M1, the µ subunit of AP-2, has recently been shown to be essential for Hepatitis C virus (HCV) assembly. While its knockdown had no effect on HCV RNA replication, it dramatically decreased both intra- and extra-cellular infectivity, consistent with an assembly defect (*Plos Pathogens* 2012, 8, e1002845). Phosphorylation of AP2M1 by GAK stimulates binding of AP2M1 to the core protein of HCV. Hence, GAK is a cellular host factor essential in mediating HCV assembly. Kinase inhibitors, such as erlotinib, which is known to target GAK, inhibits AP2M1 phosphorylation, disrupts the binding of core to AP2M1 and inhibits HCV assembly, as well as infectious virus production. Therefore, GAK inhibitors hold the potential to treat HCV infections, based on inhibition of a viral-host interaction.

The synthesis of a very limited number of isothiazolo[4,3-b]pyridine has been described in literature. The synthesis of 3-aminoisothiazolo[4,3-b]pyridine from 3-aminopicolinonitrile via 3-aminothiopicolinamide, followed by a subsequent oxidative cyclization with $H_2C_2$ to give 3-aminoisothiazolo[4,3-b]pyridine has been described in *Can. J. Chem.* 1973, 51(11), 1741-1748. Isothiazolo[4,3-b]pyridines have also been synthesized also as M1 positive allosteric modulators (*Bioorg. Med. Chem. Lett.* 2010, 20, 2533-2537).

However, none of these documents teaches or suggests isothiazolo[4,3-b]pyridine derivatives having the substitution pattern disclosed by the present invention nor their use as antiviral medicaments.

However, there is a continuous need in the art for specific and highly therapeutically active compounds, that act as GAK inhibitors and are useful for the treatment of viral infections.

SUMMARY OF THE INVENTION

The present invention is based on the unexpected finding that certain combinations of substituents at positions 3 and 6 of the isothiazolo[4,3-b]pyridine ring system, said combinations not being suggested by the prior art, show unexpected biological properties, in particular have significant GAK inhibitory activity and antiviral activities.

Numbered statements of this invention are:
1. An isothiazolo[4,3-b]pyridine derivative having the general formula I:

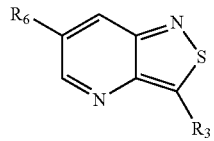

wherein
$R_3$ is selected from the group consisting of halogen, amino, morpholinyl, thiomorpholinyl, pyrrolidinyl, piperazinyl, homopiperazinyl, piperidinyl, (mono- or di-) $C_{1-12}$ alkylamino, (mono- or di-) $C_{2-12}$ alkenylamino, (mono- or di-) $C_{2-12}$ alkynylamino, monoarylamino; diarylamino; (mono- or di-) $C_{3-10}$ cycloalkylamino, $C_{3-10}$ cycloalkyl$C_{1-4}$ alkylamino, (mono- or di-) $C_{3-10}$ cycloalkenylamino, (mono- or di-) hydroxy $C_{1-7}$ alkylamino, (mono- or di-) $C_{1-4}$ alkylarylamino, (mono- or di-) aryl$C_{1-4}$ alkylamino, mercapto $C_{1-7}$ alkyl, $C_{1-7}$ alkoxy, $C_{1-4}$ alkoxy$C_{1-4}$ alkylamino, alkoxyaryl, $C_{3-10}$ cycloalkoxy, heterocyclic-substituted alkylamino, heterocyclic-substituted arylamino, heterocyclic amino, hydroxy-alkylamino, mercaptoalkylamino, hydroxypiperidinyl, aryl and heteroaryl groups, and, wherein said morpholinyl, thiomorpholinyl, pyrrolidinyl, piperazinyl, piperidinyl, heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, and, wherein one or more carbon atoms in any ring group may be replaced with —C(=O)—;

$R_6$ is selected from the group consisting of halogen, heteroaryl and aryl groups, wherein said heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thio-heterocyclic, arylalkylthio, heterocyclic-substituted alkylthio, formyl, carbamoyl, thiocarbamoyl, ureido, thioureido, sulfonamido, hydroxylamino, alkoxy-amino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cycloalkenylamino, alkynylamino, arylamino, arylalkylamino, hydroxyalkylamino, mercaptoalkylamino, heterocyclic amino;

and/or a pharmaceutical acceptable addition salt thereof and/or a stereoisomer thereof and/or a solvate thereof, for use in the prevention or treatment of a viral infection in an animal, mammal or human.

2. An isothiazolo[4,3-b]pyridine derivative for the use according to statement 1, wherein said viral infection is an infection with an RNA-virus.

3. An isothiazolo[4,3-b]pyridine derivative for the use according to statement 1, wherein said viral infection is a Retroviral infection, a Flaviviral infection, a Coronaviridal infection, a Filoviridae infection, an orthomyxoviridae infection, a picoRNAviridae infection, or an enteroviral infection.

4. An isothiazolo[4,3-b]pyridine derivative for the use according to statement 1, wherein said viral infection is a HIV-1 infection, a HIV-2 infection, a HCV infection, a Dengue virus infection, an infection with a Flavivirus other than HCV and Dengue virus such as a yellow fever virus infection, an Ebolavirus infection, a SARS coronavirus infection, an influenza virus infection, or a polio virus infection.

5. An isothiazolo[4,3-b]pyridine derivative for the use according to statement 1, wherein said viral infection is a Retroviral or a Flaviviral infection.

6. An isothiazolo[4,3-b]pyridine derivative for the use according to statement 1, wherein said viral infection is a HIV-1 infection, a HIV-2 infection, a HCV infection, a Dengue virus infection or an infection with a Flavivirus other than HCV and Dengue virus such as a yellow fever virus infection.

7. An isothiazolo[4,3-b]pyridine derivative for the use according to any of statements 1 to 6, wherein $R^6$ is selected from the group consisting of 3,4-dimethoxyphenyl; 3-thienyl; phenyl; 2-thienyl; 4-methoxycarbonyl-3-methoxy-phenyl; 4-acetoxy-3-methoxyphenyl; 3-acetoxy-4-methoxyphenyl; 3,5-dimethoxyphenyl; 3,4,5-trimethoxyphenyl, 2,5-dimethoxyphenyl, 3-methoxyphenyl; 4-methoxyphenyl; 3-furanyl; N-methylbenzamide; 2-bromo-4,5-dimethoxyphenyl; 3-methoxy-4-hydroxyphenyl and 4-amino-3-methoxyphenyl.

8. An isothiazolo[4,3-b]pyridine derivative for the use according to any of statements 1 to 7, wherein $R^3$ is selected from the group consisting of morpholinyl, ethanolamino, thiomorpholinyl, piperidinyl, 4-piperidinone, 4-hydroxypiperidinyl, 3-hydroxypiperidinyl, n-pentanolamino, tetrahydropyranyl-4-amino, diethanolamino, 2,3-dihydroxy-propanylamino, pyrrolidinyl, methoxyethylamino, cyclopropylmethylamino, dimethylamino, diethylamino, 2,6-dimethylmorpholinyl, phenyl, pyridinyl, thienyl and ethoxy.

9. An isothiazolo[4,3-b]pyridine derivative for the use according to any of statements 1 to 8, wherein the isothiazolo[4,3-b]pyridine derivative is selected from the group consisting of:
3-morpholino-6-phenyl-isothiazolo[4,3-b]pyridine;
3-morpholino-6-(4-fluoro-phenyl)-isothiazolo[4,3-b]pyridine;
3-morpholino-6-(3-pyridyl))-isothiazolo[4,3-b]pyridine;

3-morpholino-6-(3,4-dimethoxyphenyl)-isothiazolo[4,3-b]pyridine;
3-morpholino-6-(3-thienyl)-isothiazolo[4,3-b]pyridine;
3-ethanolamino-6-(3-pyridyl)-isothiazolo[4,3-b]pyridine;
3-ethanolamino-6-(3,4-dimethoxyphenyl)-isothiazolo[4,3-b]pyridine;
3-ethanolamino-6-(3-thienyl)-isothiazolo[4,3-b]pyridine;
3-ethanolamino-6-(3-phenyl)-isothiazolo[4,3-b]pyridine;
3-methoxy-6-phenyl-isothiazolo[4,3-b]pyridine;
3-methoxy-6-(4-fluoro-phenyl)-isothiazolo[4,3-b]pyridine;
3-methoxy-6-(3-pyridyl)-isothiazolo[4,3-b]pyridine;
3-methoxy-6-(3,4-dimethoxyphenyl)-isothiazolo[4,3-b]pyridine;
3-methoxy-6-(3-thienyl)-isothiazolo[4,3-b]pyridine;
3-(N-Me-piperazinyl)-6-phenyl-isothiazolo[4,3-b]pyridine;
3-(N-Me-piperazinyl)-6-(3-pyridyl)-isothiazolo[4,3-b]pyridine;
3-(N-Me-piperazinyl)-6-(3,4-dimethoxyphenyl)-isothiazolo[4,3-b]pyridine;
3-(N-Me-piperazinyl)-6-(3-thienyl)-isothiazolo[4,3-b]pyridine;
3-(N-Me-piperazinyl)-6-(4-fluorophenyl)-isothiazolo[4,3-b]pyridine;
3-amino-6-phenyl-isothiazolo[4,3-b]pyridine;
3-amino-6-(3-pyridyl)-isothiazolo[4,3-b]pyridine;
3-amino-6-(3,4-dimethoxyphenyl)isothiazolo[4,3-b]pyridine;
3-amino-6-(4-fluorophenyl)isothiazolo[4,3-b]pyridine;
3-amino-6-(3-thienyl)isothiazolo[4,3-b]pyridine;
4-(6-(Thiophen-2-yl)isothiazolo[4,3-b]pyridin-3-yl)morpholine;
4-(6-(2,5-Dimethoxyphenyl)isothiazolo[4,3-b]pyridin-3-yl)morpholine;
4-(6-(2,4-Dimethoxyphenyl)isothiazolo[4,3-b]pyridin-3-yl)morpholine;
Methyl 2-methoxy-4-(3-morpholinoisothiazolo[4,3-b]pyridin-6-yl)benzoate;
2-Methoxy-4-(3-morpholinoisothiazolo[4,3-b]pyridin-6-yl)phenyl acetate;
4-(6-(3,5-Dimethoxyphenyl)isothiazolo[4,3-b]pyridin-3-yl)morpholine;
4-(6-(3,4,5-Trimethoxyphenyl)isothiazolo[4,3-b]pyridin-3-yl)morpholine;
2-Methoxy-4-(3-morpholinoisothiazolo[4,3-b]pyridin-6-yl)aniline;
4-(6-(Benzo[d][1,3]dioxol-5-yl)isothiazolo[4,3-b]pyridin-3-yl)morpholine;
4-(6-(Furan-3-yl)isothiazolo[4,3-b]pyridin-3-yl)morpholine;
Methyl 4-(3-morpholinoisothiazolo[4,3-b]pyridin-6-yl)benzoate;
N-Methyl-4-(3-morpholinoisothiazolo[4,3-b]pyridin-6-yl)benzamide;
6-bromo-3-(piperidin-1-yl)isothiazolo[4,3-b]pyridine;
6-bromo-3-thiomorpholinoisothiazolo[4,3-b]pyridine;
3-morpholino-6-aryl-isothiazolo[4,3-b]pyridines;
6-(3,4-dimethoxyphenyl)-3-(piperidin-1-yl)isothiazolo[4,3-b]pyridine;
6-(3,4-dimethoxyphenyl)-3-thiomorpholinoisothiazolo[4,3-b]pyridine;
3-bromo-6-(2-bromo-4,5-dimethoxyphenyl)isothiazolo[4,3-b]pyridine;
4-(6-(2-bromo-4,5-dimethoxyphenyl)isothiazolo[4,3-b]pyridin-3-yl)morpholin;
4-(6-(3-methoxyphenyl)isothiazolo[4,3-b]pyridin-3-yl)morpholine;
2-methoxy-5-(3-morpholinoisothiazolo[4,3-b]pyridin-6-yl)phenyl acetate;
4-(6-(4-methoxyphenyl) isothiazolo[4,3-b]pyridin-3-yl)morpholine;
1-(6-(3,4-dimethoxyphenyl)isothiazolo[4,3-b]pyridin-3-yl)piperidin-4-one;
1-(6-(3,4-dimethoxyphenyl)isothiazolo[4,3-b]pyridin-3-yl)piperidin-4-ol;
5-(6-(3,4-dimethoxyphenyl)isothiazolo[4,3-b]pyridin-3-ylamino)pentan-1-ol;
1-(6-(3,4-dimethoxyphenyl)isothiazolo[4,3-b]pyridin-3-yl)piperidin-3-ol;
6-(3, 4-dimethoxyphenyl)-N-(tetrahydro-2H-pyran-4-yl)isothiazolo[4,3-b]pyridin-3-amine;
2,2'-(6-(3,4-dimethoxyphenyl)isothiazolo[4,3-b]pyridin-3-ylazanediyl)diethanol;
3-(6-(3,4-dimethoxyphenyl)isothiazolo[4,3-b]pyridin-3-ylamino)propane-1,2-diol;
ethyl-4-(6-(3,4-dimethoxyphenyl)isothiazolo[4,3-b]pyridin-3-ylamino)piperidine-1-carboxylate;
6-(3,4-dimethoxyphenyl)-3-(pyrolidin-1-yl)isothiazolo[4,3-b]pyridine;
6-(3,4-dimethoxyphenyl)-N-phenethylisothiazolo[4,3-b]pyridin-3-amine;
6-(3,4-dimethoxyphenyl)-N-(2-methoxyethyl)isothiazolo[4,3-b]pyridin-3-amine;
N-(cyclopropylmethyl)-6-(3,4-dimethoxyphenyl)isothiazolo[4,3-b]pyridin-3-amine;
6-(3,4-dimethoxyphenyl)-N,N-dimethylisothiazolo[4,3-b]pyridin-3-amine;
6-(3,4-dimethoxyphenyl)-N,N-diethylisothiazolo[4,3-b]pyridin-3-amine;
(2R,6S)-4-(6-(3,4-dimethoxyphenyl)isothiazolo[4,3-b]pyridin-3-yl)-2,6-dimethylmorpholine;
8-(6-(3,4-dimethoxyphenyl)isothiazolo[4,3-b]pyridin-3-yl)-1,4-dioxa-8-azaspiro[4.5]decane;
6-(3,4-dimethoxyphenyl)-3-phenylisothiazolo[4,3-b]pyridine;
6-(3,4-dimethoxyphenyl)-3-(pyridin-4-yl)isothiazolo[4,3-b]pyridine;
6-(3,4-dimethoxyphenyl)-3-(thiophen-3-yl)isothiazolo[4,3-b]pyridine;
6-(3,4-dimethoxyphenyl)isothiazolo[4,3-b]pyridine;
6-(2-bromo-4,5-dimethoxyphenyl)-3-(4-methylpiperdin-1-yl)isothiazolo[4,3-b]pyridine; and
6-(2-bromo-4,5-dimethoxyphenyl)-3-ethoxyisothiazolo[4,3-b]pyridine.

10. A method of prevention or treatment of a viral infection in an animal, mammal or human, comprising the administration of a therapeutically effective amount of an isothiazolo[4,3-b]pyridine derivative according to formula I, and/or a pharmaceutical acceptable addition salt thereof and/or a stereoisomer thereof and/or a solvate thereof,

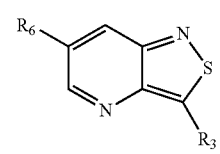

I wherein
R₃ is selected from the group consisting of halogen, amino, morpholinyl, thiomorpholinyl, pyrrolidinyl, piperazinyl, homopiperazinyl, piperidinyl, (mono- or di-) $C_{1-12}$ alkylamino, (mono- or di-) $C_{2-12}$ alkenylamino, (mono- or di-) $C_{2-12}$ alkynylamino, monoarylamino; diarylamino; (mono- or di-) $C_{3-10}$ cycloalkylamino, $C_{3-10}$ cycloalkyl$C_{1-4}$ alkylamino, (mono- or di-) $C_{3-10}$ cycloalkenylamino, (mono- or di-) hydroxy $C_{1-7}$ alkylamino, (mono- or di-) $C_{1-4}$ alkylarylamino, (mono- or di-) aryl$C_{1-4}$ alkylamino, mercapto $C_{1-7}$ alkyl, $C_{1-7}$ alkoxy, $C_{1-4}$-alkoxy$C_{1-4}$ alkylamino, alkoxyaryl, $C_{3-10}$ cycloalkoxy, heterocyclic-substituted alkylamino, heterocyclic-substituted arylamino, heterocyclic amino, hydroxy-alkylamino, mercaptoalkylamino, hydroxypiperidinyl, aryl and heteroaryl groups, and, wherein said morpholinyl, thiomorpholinyl, pyrrolidinyl, piperazinyl, piperidinyl, heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, and, wherein one or more carbon atoms in any ring group may be replaced with —C(=O)—;
R₆ is selected from the group consisting of halogen, heteroaryl and aryl groups, wherein said heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thio-heterocyclic, arylalkylthio, heterocyclic-substituted alkylthio, formyl, carbamoyl, thiocarbamoyl, ureido, thioureido, sulfonamido, hydroxylamino, alkoxy-amino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cycloalkenylamino, alkynylamino, arylamino, arylalkylamino, hydroxyalkylamino, mercaptoalkylamino, heterocyclic amino.

11. An isothiazolo[4,3-b]pyridine derivative for the use according to any of statements 1 to 8, wherein $R^6$ is a dimethoxyphenyl or a trimethoxyphenyl, wherein said phenyl optionally has one or more substituents selected from the group consisting of a halogen, amino, trifluoromethyl, hydroxyl, sulfhydryl, nitro, methoxy, acetoxy, and methoxycarbanoyl.

12. An isothiazolo[4,3-b]pyridine derivative for the use according to any of statements 1 to 8, wherein $R^6$ is a thienyl, for example 3-thienyl or 2-thienyl.

13. An isothiazolo[4,3-b]pyridine derivative for the use according to any of statements 1 to 8, wherein $R^6$ is a methoxyphenyl, wherein said phenyl optionally has one or more substituents selected from the group consisting of a halogen, amino, trifluoromethyl, hydroxyl, sulfhydryl, nitro, methoxy, acetoxy, and methoxycarbanoyl.

14. An isothiazolo[4,3-b]pyridine derivative for the use according to any of statements 1 to 8, wherein $R^6$ is a 3-methoxyphenyl or 4-methoxyphenyl, wherein said phenyl optionally has one or more substituents selected from the group consisting of a halogen, amino, trifluoromethyl, hydroxyl, sulfhydryl, nitro, methoxy, acetoxy, and methoxycarbanoyl.

15. An isothiazolo[4,3-b]pyridine derivative for the use according to any of statements 1 to 8, wherein $R^6$ is selected from 3,4-dimethoxyphenyl, 4-methoxycarbonyl-3-methoxy-phenyl, 4-amino-3-methoxyphenyl, 3-methoxy-4-hydroxyphenyl, 3,5-dimethoxyphenyl, 2-bromo-4,5-dimethoxyphenyl, 3,4,5-trimethoxyphenyl and 4-amino-3-methoxyphenyl.

16. An isothiazolo[4,3-b]pyridine derivative for the use according to any of statements 1 to 8 and 13, wherein $R^6$ is acetoxymethoxyphenyl, such as 4-acetoxy-3-methoxyphenyl and 3-acetoxy-4-methoxyphenyl.

17. An isothiazolo[4,3-b]pyridine derivative for the use according to any of statements 1 to 8 and 11, wherein $R^6$ is 2,5-dimethoxyphenyl; 3,4-dimethoxyphenyl, 3,5-dimethoxyphenyl, or 4,5-dimethoxyphenyl, wherein said phenyl optionally has one or more substituents selected from the group consisting of a halogen, amino, trifluoromethyl, hydroxyl, sulfhydryl, nitro, methoxy, acetoxy, and methoxycarbanoyl, such as 2-bromo-4,5-dimethoxyphenyl.

18. An isothiazolo[4,3-b]pyridine derivative for the use according to any of statements 1 to 8, wherein $R^6$ is furanyl, such as 3-furanyl.

19. An isothiazolo[4,3-b]pyridine derivative for the use according to any of statements 1 to 8, wherein $R^6$ is N-methylbenzamide, for example 4-(N-methylaminocarbonyl)phenyl.

20. An isothiazolo[4,3-b]pyridine derivative for the use according to any of statements 1 to 8 and 11 to 19, wherein $R^3$ is a morpholinyl, optionally substituted with one or more substituents selected from the group consisting of a halogen, $C_{1-4}$ alkyl, amino, trifluoromethyl, hydroxyl, sulfhydryl, nitro, methoxy, acetoxy, and methoxycarbanoyl, such as 2,6-dimethylmorpholinyl.

21. An isothiazolo[4,3-b]pyridine derivative for the use according to any of statements 1 to 8 and 11 to 20, wherein $R^3$ is a (mono- or di-) $C_{1-4}$ alkyl substituted morpholinyl or a (mono- or di-) $C_{1-2}$ alkyl substituted morpholinyl.

22. An isothiazolo[4,3-b]pyridine derivative for the use according to any of statements 1 to 8 and 11 to 21, wherein $R^3$ is thiomorpholinyl.

23. An isothiazolo[4,3-b]pyridine derivative for the use according to any of statements 1 to 8 and 11 to 21, wherein $R^3$ is piperidinyl optionally substituted with one or more substituents selected from the group consisting of a halogen, $C_{1-2}$ alkyl, amino, trifluoromethyl, hydroxyl, sulfhydryl, nitro, methoxy, acetoxy, and methoxycarbanoyl, such as 4-hydroxypiperidinyl or 3-hydroxypiperidinyl.

24. An isothiazolo[4,3-b]pyridine derivative for the use according to any of statements 1 to 8 and 11 to 21, wherein $R^3$ is 4-piperidinone.

25. An isothiazolo[4,3-b]pyridine derivative for the use according to any of statements 1 to 8 and 11 to 21, wherein $R^3$ is (mono- or di-)$C_{1-7}$ alkylamino, such as dimethylamino and diethylamino.

26. An isothiazolo[4,3-b]pyridine derivative for the use according to any of statements 1 to 8 and 11 to 21, wherein $R^3$ is (mono- or di-) hydroxy $C_{1-7}$ alkylamino, such as ethanolamino, n-pentanolamino, diethanolamino and 2,3-dihydroxy-propanylamino.

27. An isothiazolo[4,3-b]pyridine derivative for the use according to any of statements 1 to 8 and 11 to 21, wherein $R^3$ is $C_{1-4}$ alkoxy$C_{1-4}$ alkyl amino such as methoxyethylamino.

28. An isothiazolo[4,3-b]pyridine derivative for the use according to any of statements 1 to 8 and 11 to 21, wherein $R^3$ is $C_{3-10}$ cycloalkyl$C_{1-4}$ alkylamino, such as cyclopropylmethylamino.
29. An isothiazolo[4,3-b]pyridine derivative for the use according to any of statements 1 to 8 and 11 to 21, wherein $R^3$ is $C_{1-7}$ alkoxy, or $C_{1-4}$ alkoxy, such as ethoxy.
30. An isothiazolo[4,3-b]pyridine derivative for the use according to any of statements 1 to 8 and 11 to 21, wherein $R^3$ is an aryl such as a phenyl.
31. An isothiazolo[4,3-b]pyridine derivative for the use according to any of statements 1 to 8 and 11 to 21, wherein $R^3$ is a heteroaryl, such as pyridinyl and thienyl.
32. An isothiazolo[4,3-b]pyridine derivative for the use according to any of statements 1 to 8 and 11 to 21, wherein $R^3$ is an unsubstituted or substituted thiomorpholinyl, morpholinyl, pyrrolidinyl, piperazinyl or piperidinyl and said $R^3$ is attached in formula I via its nitrogen atom.
33. An isothiazolo[4,3-b]pyridine derivative for the use according to any of statements 1 to 9 and 11 to 32, wherein said isothiazolo[4,3-b]pyridine derivative is used in combination with one or more biologically active antiviral drugs.
34. An isothiazolo[4,3-b]pyridine derivative for the use according to any of statements 1 to 9 and 11 to 33, wherein said isothiazolo[4,3-b]pyridine derivative is used in combination with at least one AAK1 (adaptor-associated kinase 1) inhibitor.
35. An isothiazolo[4,3-b]pyridine derivative for the use according to statement 34, wherein said at least one AAK1 inhibitor is sunitinib.
36. A composition comprising an isothiazolo[4,3-b]pyridine derivative as defined in any of statements 1 to 9 and 11 to 32, and at least one AAK1 inhibitor.
37. The composition according to statement 36, wherein said at least one AAK1 inhibitor is sunitinib.
38. A composition according to any one of statements 36 or 37, for use in the prevention or treatment of Ebolavirus infections.

One embodiment of the present invention concerns a compound according to the invention and its use according to the present invention, including the isothiazolo[4,3-b]pyridine of formula (I), wherein $R^6$ is a dimethoxyphenyl or a trimethoxyphenyl. Another embodiment of the present invention concerns a compound according to the invention and its use according to the present invention, including the isothiazolo[4,3-b]pyridine of formula (I), wherein $R^6$ is a thienyl. Another embodiment of the present invention concerns a compound according to the invention and its use according to the present invention, including the isothiazolo[4,3-b]pyridine of formula (I), wherein $R^6$ is a methoxyphenyl, more specifically a 3-methoxyphenyl or 4-methoxyphenyl, wherein said phenyl optionally has one or more substituents selected from the group consisting of a halogen, amino, trifluoromethyl, hydroxyl, sulthydryl, nitro, methoxy, acetoxy, and methoxycarbanoyl, such as 3,4-dimethoxyphenyl, 4-methoxycarbonyl-3-methoxy-phenyl, 4-amino-3-methoxyphenyl, 3-methoxy-4-hydroxyphenyl, 3,5-dimethoxyphenyl, 2-bromo-4,5-dimethoxyphenyl, 3,4,5-trimethoxyphenyl and 4-amino-3-methoxyphenyl.

One embodiment of the present invention concerns a compound according to the invention and its use according to the present invention, including the isothiazolo[4,3-b]pyridine of formula (I), wherein $R^3$ is morpholinyl or $C_{1-4}$ alkoxy$C_{1-4}$ alkyl amino such as methoxyethylamino.

DETAILED DESCRIPTION OF THE INVENTION AND DEFINITIONS

Scheme 1 schematically shows a method for making 3,6-disubstituted isothiazolo[4,3-b]pyridine derivatives.

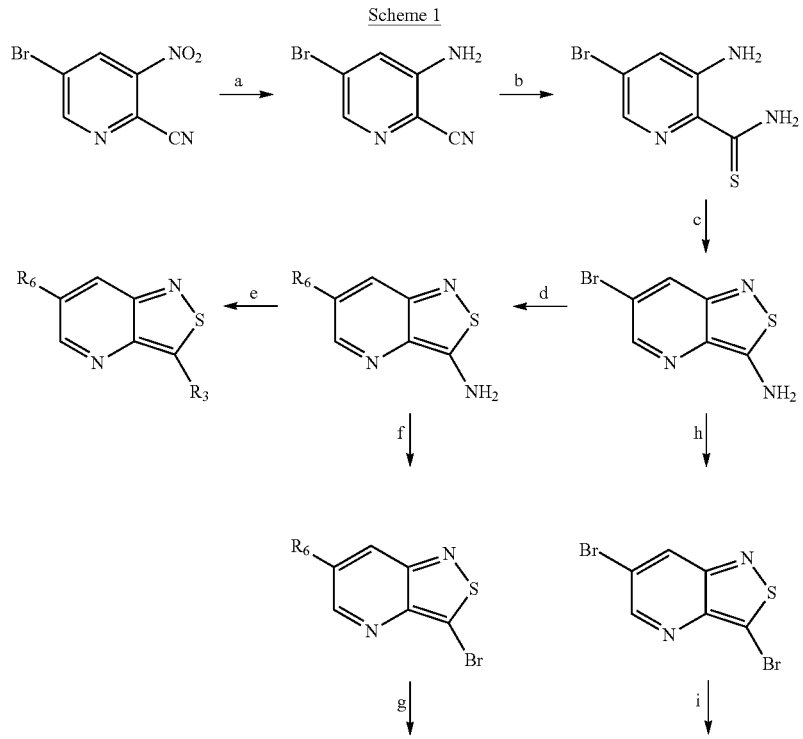

-continued

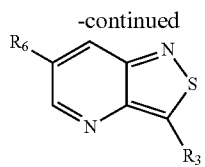 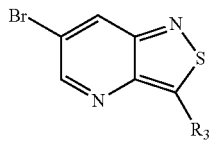

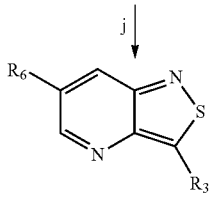

The nitro group of 3-nitro-5-bromopyridine-2-carbonitrile is reduced in step (a) either catalytically (e.g. by using platinum or palladium under an atmosphere of hydrogen) or chemically (e.g. by using iron or tin under acidic conditions). The aromatic thioamide can then be obtained by treatment of the corresponding nitrile with gaseous hydrogen sulfide in the presence of alkali metal sulfide or ammonium sulfide in alcohols. Alternatively, thionation agents (such as phosphorus pentasulfide or Lawesson's reagent) can be used in step (b). An oxidative ring closure using hydrogen peroxide, yields then the isothiazolo[4,3-b]pyridine scaffold in step (c). The bromine on the pyridine moiety can be used as leaving group for a variety of palladium-catalyzed reactions such as, but not limited to, a Suzuki reaction (by reaction with an arylboronic acid), a Heck reaction (by reaction with a terminal alkene), a Sonogashira reaction (by reaction with a terminal alkyne), a Buchwald-Hartwig coupling (by reaction with amines) in step (d), yielding 3-amino-6-substituted isothiazolo[4,3-b]pyridine analogues. The amino group can be used for further derivatisation by coupling with acid chlorides (yielding amides), by reaction with iso(thio)cyanates affording (thio)urea analogues, by coupling with sulfonyl chlorides (furnishing sulfonamides), by reaction with chloroformates (yielding carbamates) in step (e). Alternatively, reductive amination with aldehydes in step (e) is also feasible, yielding 3-alkylamino-6-substituted isothiazolo[4,3-b]pyridine derivatives. In step (f), a diazotation reaction furnished the 3-bromo-6-substituted-isothiazolo[4,3-b]pyridine analogue. This bromo derivative can be used in step (g) for a wide variety of palladium-catalyzed cross-coupling reactions yielding 3,6-disubsituted isothiazolo[4,3-b]pyridine analogues.

Alternatively, a diazotation reaction in step (h) afforded the 3,6-dibromo-isothiazolo[4,3-b]pyridine. Treatment with a suitable nucleophile, bearing the general formula $R_3H$ (amines, thiols or alcoxides) yielded a 3-$R_3$-substituted-6-bromo-isothiazolo[4,3-b]pyridine analogue in step (i). Palladium-catalyzed reactions allow to introduce structural variety in step (j) at position 6 of the isothiazolo[4,3-b]pyridine scaffold.

According to one embodiment, the present invention encompasses the isothiazolo[4,3-b]pyridine derivatives of the general formula I:

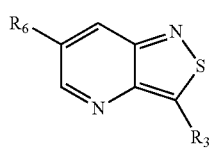

I wherein $R_3$ is selected from the group consisting of halogen, amino, morpholinyl, thiomorpholinyl, pyrrolidinyl, piperazinyl, homopiperazinyl, piperidinyl, (mono- or di-) $C_{1-12}$ alkylamino, (mono- or di-) $C_{2-12}$ alkenylamino, (mono- or di-) $C_{2-12}$ alkynylamino, monoarylamino; diarylamino; (mono- or di-) $C_{3-10}$ cycloalkylamino, $C_{3-10}$ cycloalkyl$C_{1-4}$ alkylamino, (mono- or di-) $C_{3-10}$ cycloalkenylamino, (mono- or di-) hydroxy $C_{1-7}$ alkylamino, (mono- or di-) $C_{1-12}$ alkylarylamino, (mono- or di-) aryl$C_{1-4}$ alkylamino, mercapto $C_{1-7}$ alkyl, $C_{1-7}$ alkoxy, $C_{1-4}$ alkoxy$C_{1-4}$ alkylamino, alkoxyaryl, $C_{3-10}$ cycloalkoxy, heterocyclic-substituted alkylamino, heterocyclic-substituted arylamino, heterocyclic amino, hydroxy-alkylamino, mercaptoalkylamino, hydroxypiperidinyl, aryl and heteroaryl groups, and, wherein said morpholinyl, thiomorpholinyl, pyrrolidinyl, piperazinyl, piperidinyl, heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, and, wherein one or more carbon atoms in any ring group may be replaced with —C(=O)—;

$R_6$ is selected from the group consisting of halogen, heteroaryl and aryl groups, wherein said heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thio-heterocyclic, arylalkylthio, heterocyclic-substituted alkylthio, formyl, carbamoyl, thiocarbamoyl, ureido, thioureido, sulfonamido, hydroxylamino, alkoxy-amino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cycloalkenylamino, alkynylamino, arylamino, arylalkylamino, hydroxyalkylamino, mercaptoalkylamino, heterocyclic amino;

and/or a pharmaceutical acceptable addition salt thereof and/or a stereoisomer thereof and/or a solvate thereof, and their use in the prevention or treatment of a viral infection in an animal, mammal or human.

One embodiment of the present invention concerns a compound according to the invention, including its use according to the present invention, including the isothiazolo[4,3-b]pyridine of formula (I), wherein $R^6$ is a dimethoxyphenyl or a trimethoxyphenyl. Another embodiment of the present invention concerns a compound according to the invention, including its use according to the present invention, including the isothiazolo[4,3-b]pyridine of formula (I), wherein $R^6$ is a thienyl. Another embodiment of the present invention concerns a compound according to the invention, including its use according to the present invention, including the isothiazolo[4,3-b]pyridine of formula (I), wherein $R^6$ is a methoxyphenyl, more specifically a 3-methoxyphenyl or 4-methoxyphenyl, wherein said phenyl optionally has one or more substituents selected from the group consisting of a halogen, amino, trifluoromethyl, hydroxyl, sulfhydryl, nitro, methoxy, acetoxy, and methoxycarbanoyl, such as 3,4-dimethoxyphenyl, 4-methoxycarbonyl-3-methoxy-phenyl, 4-amino-3-methoxyphenyl, 3-methoxy-4-hydroxyphenyl, 3,5-dimethoxyphenyl, 2-bromo-4,5-dimethoxyphenyl, 3,4,5-trimethoxyphenyl and 4-amino-3-methoxyphenyl.

One embodiment of the present invention concerns a compound according to the invention, including its use according to the present invention, including the isothiazolo[4,3-b]pyridine of formula (I), wherein $R^6$ is selected from the group consisting of 3,4-dimethoxyphenyl; 3-thienyl; phenyl; 2-thienyl; 4-methoxycarbonyl-3-methoxy-phenyl; 4-acetoxy-3-methoxyphenyl; 3-acetoxy-4-methoxyphenyl; 3-methoxyphenyl; 4-methoxyphenyl; 3-furanyl; N-methylbenzamide; 3-methoxy-4-hydroxyphenyl; 3,5-dimethoxyphenyl; 2,5-dimethoxyphenyl; 2-bromo-4,5-dimethoxyphenyl; 3,4,5-trimethoxyphenyl and 4-amino-3-methoxyphenyl. In a more specific embodiment said $R^6$ is 3,4-dimethoxyphenyl. In another specific embodiment said $R^6$ is 3-thienyl. In another specific embodiment said $R^6$ is phenyl. In another specific embodiment said $R^6$ is 2-thienyl. In another specific embodiment said $R^6$ is 4-methoxycarbonyl-3-methoxy-phenyl. In another specific embodiment said $R^6$ acetoxymethoxyphenyl, such as 4-acetoxy-3-methoxyphenyl and 3-acetoxy-4-methoxyphenyl. In another specific embodiment said $R^6$ 2,5-dimethoxyphenyl or 3,5-dimethoxyphenyl. In another specific embodiment said $R^6$ is a dimethoxyphenyl, such as 2,5-dimethoxyphenyl; 3,4-dimethoxyphenyl, 3,5-dimethoxyphenyl, or 4,5-dimethoxyphenyl, wherein said phenyl optionally has one or more substituents selected from the group consisting of a halogen, amino, trifluoromethyl, hydroxyl, sulfhydryl, nitro, methoxy, acetoxy, and methoxycarbanoyl, such as 2-bromo-4,5-dimethoxyphenyl. In another specific embodiment said $R^6$ is trimethoxyphenyl, such as 3,4,5-trimethoxyphenyl. In another specific embodiment said $R^6$ is 4-amino-3-methoxyphenyl. In another specific embodiment said $R^6$ is furanyl, such as 3-furanyl. In another specific embodiment said $R^6$ is N-methylbenzamide. One embodiment of the present invention concerns a compound according to the invention, including its use according to the present invention, including the isothiazolo[4,3-b]pyridine of formula (I), wherein $R^3$ is selected from the group consisting of morpholinyl, ethanolamino, thiomorpholinyl, piperidinyl, 4-piperidinone, 4-hydroxypiperidinyl, 3-hydroxypiperidinyl, n-pentanolamino, tetrahydropyranyl-4-amino, diethanolamino, 2,3-dihydroxy-propanylamino, pyrrolidinyl, methoxyethylamino, cyclopropylmethylamino, dimethylamino, diethylamino, 2,6-dimethylmorpholinyl, phenyl, pyridinyl, thienyl and ethoxy. In a specific embodiment said $R^3$ is morpholinyl. In certain embodiments said $R^3$ is a substituted morpholinyl, wherein said morpholinyl is substituted with one or more substituents selected from the group consisting of a halogen, $C_{1-4}$ alkyl, amino, trifluoromethyl, hydroxyl, sulfhydryl, nitro, methoxy, acetoxy, and methoxycarbanoyl, such as 2,6-dimethylmorpholinyl. In another embodiment said $R^3$ is a (mono- or di-) $C_{1-4}$ alkyl substituted morpholinyl or a (mono- or di-) $C_{1-2}$ alkyl substituted morpholinyl. In another specific embodiment said $R^3$ is thiomorpholinyl. In another specific embodiment said $R^3$ is piperidinyl. In another specific embodiment said $R^3$ is a piperidinyl, optionally substituted with one or more substituents selected from the group consisting of a halogen, $C_{1-2}$ alkyl, amino, trifluoromethyl, hydroxyl, sulfhydryl, nitro, methoxy, acetoxy, and methoxycarbanoyl, such as 4-hydroxypiperidinyl or 3-hydroxypiperidinyl. In another specific embodiment said $R^3$ is 4-piperidinone. In another embodiment said $R^3$ is (mono- or di-)$C_{1-7}$ alkylamino, such as dimethylamino and diethylamino. In another embodiment said $R^3$ is (mono- or di-) hydroxy $C_{1-7}$ alkylamino, such as ethanolamino, n-pentanolamino, diethanolamino and 2,3-dihydroxy-propanylamino. In another specific embodiment said $R^3$ is tetrahydropyran-4-amino. In another specific embodiment said $R^3$ is pyrrolidinyl. In another embodiment said $R^3$ is $C_{1-4}$ alkoxy$C_4$ alkyl amino such as methoxyethylamino. In another embodiment said $R^3$ is $C_{3-10}$ cycloalkyl$C_{1-4}$ alkylamino, such as cyclopropylmethylamino. In another embodiment said $R^3$ is $C_{1-7}$ alkoxy, or $C_{1-4}$ alkoxy, such as ethoxy. In another embodiment said $R^3$ is an aryl such as a phenyl. In another embodiment said $R^3$ is a heteroaryl, such as pyridinyl and thienyl.

In a particular embodiment, when said $R^3$ is an unsubstituted or substituted thiomorpholinyl, morpholinyl, pyrrolidinyl, piperazinyl or piperidinyl said $R^3$ is attached in formula I via its nitrogen atom.

In a particular embodiment, the present invention also relates to the isothiazolo[4,3-b]pyridine derivatives of formula I, including their use according to the present invention, being selected from the group consisting of:
  3-morpholino-6-phenyl-isothiazolo[4,3-b]pyridine;
  3-morpholino-6-(4-fluoro-phenyl)isothiazolo[4,3-b]pyridine;
  3-morpholino-6-(3-pyridyl))isothiazolo[4,3-b]pyridine;
  3-morpholino-6-(3,4-dimethoxyphenyl)isothiazolo[4,3-b]pyridine;
  3-morpholino-6-(3-thienyl)isothiazolo[4,3-b]pyridine;
  3-ethanolamino-6-(3-pyridyl)isothiazolo[4,3-b]pyridine;
  3-ethanolamino-6-(3,4-dimethoxyphenyl)isothiazolo[4,3-b]pyridine;
  3-ethanolamino-6-(3-thienyl)isothiazolo[4,3-b]pyridine;
  3-ethanolamino-6-(3-phenyl)isothiazolo[4,3-b]pyridine;
  3-methoxy-6-phenyl-isothiazolo[4,3-b]pyridine;
  3-methoxy-6-(4-fluoro-phenyl)isothiazolo[4,3-b]pyridine;
  3-methoxy-6-(3-pyridyl)isothiazolo[4,3-b]pyridine;
  3-methoxy-6-(3, 4-dimethoxyphenyl)isothiazolo[4,3-b]pyridine;
  3-methoxy-6-(3-thienyl)isothiazolo[4,3-b]pyridine;
  3-(N-Me-piperazinyl)-6-phenyl-isothiazolo[4,3-b]pyridine;
  3-(N-Me-piperazinyl)-6-(3-pyridyl)isothiazolo[4,3-b]pyridine;
  3-(N-Me-piperazinyl)-6-(3,4-dimethoxyphenyl)isothiazolo[4,3-b]pyridine;
  3-(N-Me-piperazinyl)-6-(3-thienyl)isothiazolo[4,3-b]pyridine;
  3-(N-Me-piperazinyl)-6-(4-fluorophenyl)isothiazolo[4,3-b]pyridine;
  3-amino-6-phenyl-isothiazolo[4,3-b]pyridine;
  3-amino-6-(3-pyridyl)isothiazolo[4,3-b]pyridine;

3-amino-6-(3,4-dimethoxyphenyl)isothiazolo[4,3-b]pyridine;
3-amino-6-(4-fluorophenyl)isothiazolo[4,3-b]pyridine;
3-amino-6-(3-thienyl)isothiazolo[4,3-b]pyridine;
4-(6-(Thiophen-2-yl)isothiazolo[4,3-b]pyridin-3-yl)morpholine;
4-(6-(2,5-Dimethoxyphenyl)isothiazolo[4,3-b]pyridin-3-yl)morpholine;
4-(6-(2,4-Dimethoxyphenyl)isothiazolo[4,3-b]pyridin-3-yl)morpholine;
Methyl 2-methoxy-4-(3-morpholinoisothiazolo[4,3-b]pyridine-6-yl)benzoate;
2-Methoxy-4-(3-morpholinoisothiazolo[4,3-b]pyridin-6-yl)phenyl acetate;
4-(6-(3,5-Dimethoxyphenyl)isothiazolo[4,3-b]pyridin-3-yl)morpholine;
4-(6-(3,4,5-Trimethoxyphenyl)isothiazolo[4,3-b]pyridin-3-yl)morpholine;
2-Methoxy-4-(3-morpholinoisothiazolo[4,3-b]pyridin-6-yl)aniline;
4-(6-(Benzo[d][1,3]dioxol-5-yl)isothiazolo[4,3-b]pyridin-3-yl)morpholine;
4-(6-(Furan-3-yl)isothiazolo[4,3-b]pyridin-3-yl)morpholine;
Methyl 4-(3-morpholinoisothiazolo[4,3-b]pyridin-6-yl)benzoate;
N-Methyl-4-(3-morpholinoisothiazolo[4,3-b]pyridin-6-yl)benzamide;
6-bromo-3-(piperidin-1-yl)isothiazolo[4,3-b]pyridine;
6-bromo-3-thiomorpholinoisothiazolo[4,3-b]pyridine;
3-morpholino-6-aryl-isothiazolo[4,3-b]pyridines;
6-(3,4-dimethoxyphenyl)-3-(piperidin-1-yl)isothiazolo[4,3-b]pyridine;
6-(3,4-dimethoxyphenyl)-3-thiomorpholinoisothiazolo[4,3-b]pyridine;
3-bromo-6-(2-bromo-4,5-dimethoxyphenyl)isothiazolo[4,3-b]pyridine;
4-(6-(2-bromo-4,5-dimethoxyphenyl)isothiazolo[4,3-b]pyridin-3-yl)morpholine;
4-(6-(3-methoxyphenyl)isothiazolo[4,3-b]pyridin-3-yl)morpholine;
2-methoxy-5-(3-morpholinoisothiazolo[4,3-b]pyridin-6-yl)phenyl acetate;
4-(6-(4-methoxyphenyl) isothiazolo[4,3-b]pyridin-3-yl)morpholine;
1-(6-(3,4-dimethoxyphenyl)isothiazolo[4,3-b]pyridin-3-yl)piperidin-4-one;
1-(6-(3,4-dimethoxyphenyl)isothiazolo[4,3-b]pyridin-3-yl)piperidin-4-ol;
5-(6-(3,4-dimethoxyphenyl)isothiazolo[4,3-b]pyridin-3-ylamino)pentan-1-ol;
1-(6-(3,4-dimethoxyphenyl)isothiazolo[4,3-b]pyridin-3-yl)piperidin-3-ol;
6-(3, 4-dimethoxyphenyl)-N-(tetrahydro-2H-pyran-4-yl) isothiazolo[4,3-b]pyridin-3-amine;
2,2'-(6-(3,4-dimethoxyphenyl)isothiazolo[4,3-b]pyridin-3-ylazanediyl)diethanol;
3-(6-(3,4-dimethoxyphenyl)isothiazolo[4,3-b]pyridin-3-ylamino)propane-1,2-diol;
ethyl-4-(6-(3,4-dimethoxyphenyl)isothiazolo[4,3-b]pyridin-3-ylamino)piperidine-1-carboxylate;
6-(3,4-dimethoxyphenyl)-3-(pyrolidin-1-yl)isothiazolo[4,3-b]pyridine;
6-(3,4-dimethoxyphenyl)-N-phenethylisothiazolo[4,3-b]pyridin-3-amine;
6-(3,4-dimethoxyphenyl)-N-(2-methoxyethyl)isothiazolo[4,3-b]pyridin-3-amine;
N-(cyclopropylmethyl)-6-(3,4-di methoxyphenyl)isothiazolo[4,3-b]pyridin-3-amine;
6-(3,4-dimethoxyphenyl)-N,N-dimethylisothiazolo[4,3-b]pyridin-3-amine;
6-(3,4-dimethoxyphenyl)-N,N-diethylisothiazolo[4,3-b]pyridin-3-amine;
(2R, 6S)-4-(6-(3, 4-dimethoxyphenyl)isothiazolo[4,3-b]pyridin-3-yl)-2,6-dimethylmorpholine;
8-(6-(3,4-dimethoxyphenyl)isothiazolo[4,3-b]pyridin-3-yl)-1,4-dioxa-8-azaspiro[4.5]decane;
6-(3,4-dimethoxyphenyl)-3-phenylisothiazolo[4,3-b]pyridine;
6-(3,4-dimethoxyphenyl)-3-(pyridin-4-yl)isothiazolo[4,3-b]pyridine;
6-(3,4-dimethoxyphenyl)-3-(thiophen-3-yl)isothiazolo[4,3-b]pyridine;
6-(3,4-dimethoxyphenyl)isothiazolo[4,3-b]pyridine;
6-(2-bromo-4,5-dimethoxyphenyl)-3-(4-methylpiperdin-1-yl)isothiazolo[4,3-b]pyridine; and
6-(2-bromo-4,5-dimethoxyphenyl)-3-ethoxyisothiazolo[4,3-b]pyridine.

In another particular embodiment, the invention relates to a group isothiazolo[4,3-b]pyridine derivatives, including their use according to the present invention, including the ones represented by the above mentioned structural formula (I), as well as pharmaceutical compositions comprising such isothiazolo[4,3-b]pyridine derivatives as active principle, represented by the above mentioned structural formula (I) and being in the form of a pharmaceutically acceptable salt. The latter include any therapeutically active nontoxic addition salt which compounds represented by structural formula (I) are able to form with a salt-forming agent. Such addition salts may conveniently be obtained by treating the isothiazolo[4,3-b]pyridine derivatives of the invention with an appropriate salt-forming acid or base. For instance, isothiazolo[4,3-b]pyridine derivatives having basic properties may be converted into the corresponding therapeutically active, non-toxic acid addition salt form by treating the free base form with a suitable amount of an appropriate acid following conventional procedures. Examples of such appropriate salt-forming acids include, for instance, inorganic acids resulting in forming salts such as but not limited to hydrohalides (e.g. hydrochloride and hydrobromide), sulfate, nitrate, phosphate, diphosphate, carbonate, bicarbonate, and the like; and organic monocarboxylic or dicarboxylic acids resulting in forming salts such as, for example, acetate, propanoate, hydroxyacetate, 2-hydroxypropanoate, 2-oxopropanoate, lactate, pyruvate, oxalate, malonate, succinate, maleate, fumarate, malate, tartrate, citrate, methanesulfonate, ethanesulfonate, benzoate, 2-hydroxybenzoate, 4-amino-2-hydroxybenzoate, benzene-sulfonate, p-toluene-sulfonate, salicylate, p-aminosalicylate, palmoate, bitartrate, camphorsulfonate, edetate, 1,2-ethanedisulfonate, fumarate, glucoheptonate, gluconate, glutamate, hexyiresorcinate, hydroxynaphtoate, hydroxyethanesulfonate, mandelate, methylsulfate, pantothenate, stearate, as well as salts derived from ethanedioic, propanediol, butanedioic, (Z)-2-butenedioic, (E)2-butenedioic, 2-hydroxybutanedioic, 2,3-dihydroxybutane-dioic, 2-hydroxy-1,2,3-propanetricarboxylic and cyclohexanesulfamic acids and the like. Isothiazolo[4,3-b]pyridine derivatives of this invention, including the ones represented by the structural formula (I), having acidic properties may be converted in a similar manner into the corresponding therapeutically active, non-toxic base addition salt form. Examples of appropriate salt-forming bases include, for instance, inorganic bases like metallic hydroxides such as but not limited to those of alkali and alkaline-earth metals like calcium, lithium, magnesium, potassium and sodium, or zinc, resulting in the corresponding metal salt; organic bases such as but not limited to ammonia, alkylamines, benzathine, hydrabamine, arginine, lysine, $N^1N^2$-dibenzylethylenediamine, chloroprocaine, choline, diethanolamine, ethylene-diamine, N-methylglucamine, procaine and the like.

Reaction conditions for treating the isothiazolo[4,3-b] pyridine derivatives of this invention, including the ones represented by the structural formula (I), with an appropriate salt-forming acid or base are similar to standard conditions involving the same acid or base but different organic compounds with basic or acidic properties, respectively. Preferably, in view of its use in a pharmaceutical composition or in the manufacture of a medicament for treating specific diseases, the pharmaceutically acceptable salt will be designed, i.e. the salt-forming acid or base will be selected so as to impart greater water-solubility, lower toxicity, greater stability and/or slower dissolution rate to the isothiazolo[4,3-b]pyridine derivative of this invention.

The present invention further provides the use of isothiazolo[4,3-b]pyridine derivatives of this invention, including the ones represented by the structural formula (I), or a pharmaceutically acceptable salt or a solvate thereof, as a biologically active ingredient, i.e. active principle, especially as a medicine or a diagnostic agent or for the manufacture of a medicament or a diagnostic kit. In a particular embodiment, said medicine or medicament may be for the prevention or treatment of viral diseases or infection diseases, more particularly viral infection diseases. The present invention further provides the use of said isothiazolo[4,3-b] pyridine derivatives of this invention in combination with other antiviral drugs, for the use in the prevention of treatment of viral diseases, e.g. HCV, Dengue, Ebola, SARS, Yellow Fever, Polio and Influenza virus infection (or flu). In a more specific embodiment of the present invention, said combination of isothiazolo[4,3-b]pyridine derivatives of this invention with other drugs, is a combination with AAK1 (adaptor-associated protein kinase 1 or AP-2-associated protein kinase 1) inhibitors, such as sunitinib. More particularly said combinations show a surprising and synergistic effect, as exemplified for Ebola virus in Example 92. In a specific embodiment of the present invention, said isothiazolo[4,3-b]pyridine derivatives of this invention in combination with AAK1 inhibitors, such as sunitinib are used to treat or prevent Ebolavirus infections. AAK1 inhibitors include the inhibitors described in WO2013/134228, WO2013/134219 and WO2013/134336.

The invention further relates to a method of prevention or treatment of a viral disease including a viral infection, in an animal, comprising the administration of a therapeutically effective amount of an isothiazolo[4,3-b]pyridine derivative according to this invention, including the isothiazolo[4,3-b] pyridine derivatives of formula (I) and any subgroup thereof, optionally in combination with one or more pharmaceutically acceptable excipients. The present invention also concerns the isothiazolo[4,3-b]pyridine derivatives of formula (I), any subgroup thereof, for use as a medicine for the prevention or treatment of a viral infection in an animal. In an embodiment, said viral infection is an infection with a virus from the family of the Retroviridae, the Flaviviridae, the PicoRNAviridae, the Bunyaviridae, the Arenaviridae, the Togaviridae, the Coronaviridae, the Orthomyxoviridae, the Paramyxoviridae, or the Filoviridae. In an embodiment, said viral infection is an infection with a virus from the family of the Retroviridae, the family of the Flaviviridae or the PicoRNAviridae. In a more particular embodiment, said viral infection is an infection with a virus of the genus Lentivirus, Hepacivirus, Flavivirus, Enterovirus, Phlebovirus, Arenavirus, Alphavirus, Betacoronavirus, Influenzavirus, Pneumovirus or Ebolavirus. In another more particular embodiment, said viral infection is an infection with a virus of the genus Lentivirus, Hepacivirus, Flavivirus, or Enterovirus. In an even more particular embodiment, said viral infection is an infection with a virus of the species HIV1, HIV2, HCV, Dengue virus, Poliovirus, Rhinovirus (including Rhinovirus-A, -B, and -C), Yellow Fever Virus, West Nile Virus, Japanese encephalitis virus, Powassan virus, Ebola virus, Respiratory syncytial virus, Influenzavirus (including Influenzavirus-A, -B, and -C), SARS coronavirus, Venezuelean Equine encephalitis virus, Tacaribe virus, Rift Valley fever virus or Coxsackie virus. In an even more particular embodiment, said viral infection is an infection with a virus of the species HIV1, HIV2, HCV, Dengue virus, Poliovirus or Rhinovirus. In an embodiment, said animal is a mammal, preferably said mammal is a human being. In particular embodiments of the present invention, said viral infection is caused by a virus selected from the group of HIV, HCV, and Flaviviridae other than HCV and Dengue virus. In another particular embodiment of the present invention, said viral infection is caused by a virus from the family of the Flaviridae, such as a hepacivirus and a Flavivirus such as Dengue virus. In another particular embodiment of the present invention, said viral infection is caused by a Flavivirus, such as HCV, Dengue virus, Yellow Fever Virus, West Nile Virus, Japanese encephalitis virus or Powassan virus. In another more specific embodiment of the present invention, said viral infection is a HCV infection. In another specific embodiment of the present invention, said viral infection is a Dengue virus infection. In another particular embodiment of the present invention, said viral infection is caused by a virus from the family of the retroviridae, such as a lentivirus. In another more specific embodiment of the present invention, said viral infection is an infection with HIV, such as HIV-1 and HIV-2. In particular embodiments of the present invention, said animal is a mammal. In another, more particular embodiment, said animal is a human being.

The pathologic conditions and disorders concerned by the said use, and the corresponding methods of prevention or treatment, are detailed hereinbelow. Any of the uses mentioned with respect to the present invention may be restricted to a nonmedical use (e.g. in a cosmetic composition), a non-therapeutic use, a non-diagnostic use, a non-human use (e.g. in a veterinary composition), or exclusively an in-vitro use, or a use with cells remote from an animal. The invention further relates to a pharmaceutical composition comprising: (a) one or more isothiazolo[4,3-b]pyridine derivatives of this invention, including the ones represented by the structural formula (I), and (b) one or more pharmaceutically acceptable carriers, including its medical use such as its use as an antiviral medicament for the prevention or treatment of viral diseases or infection diseases, more particularly viral infection diseases.

The pathological conditions contemplated by this invention are infection diseases, more specifically viral infection diseases.

The invention further relates to a method of prevention or treatment of a viral disease in an animal, comprising the administration of a therapeutically effective amount of an isothiazolo[4,3-b]pyridine derivative according to this invention, including the isothiazolo[4,3-b]pyridine derivatives of formula (I) and any subgroup thereof, optionally in combination with one or more pharmaceutically acceptable excipients.

The term "pharmaceutically acceptable carrier or excipient" as used herein in relation to pharmaceutical compositions and combined preparations means any material or substance with which the active principle, i.e. the isothiazolo[4,3-b]pyridine derivative of this invention, including the ones represented by the structural formula (I), and optionally another antiviral compound may be formulated in order to facilitate its application or dissemination to the locus to be treated, for instance by dissolving, dispersing or diffusing said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders. Suitable pharmaceutical carriers for use in said pharmaceutical compositions and their formulation are well known to those skilled in the art. There is no particular restriction to their selection within the present invention although, due to the usually low or very low water-solubility of the isothiazolo[4,3-b]pyridine derivatives of this invention, special attention will be paid to the selection of suitable carrier combinations that can assist in properly formulating them in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals.

The pharmaceutical compositions of the present invention may be prepared in any known manner, for instance by homogeneously mixing, dissolving, spray-drying, coating and/or grinding the active ingredients, in a one-step or a multi-steps procedure, with the selected carrier material and, where appropriate, the other additives such as surface-active agents, may also be prepared by micronisation, for instance in view to obtain them in the form of microspheres usually having a diameter of about 1 to 10 µm, namely for the manufacture of microcapsules for controlled or sustained release of the biologically active ingredient(s).

Suitable surface-active agents to be used in the pharmaceutical compositions of the present invention are non-ionic, cationic and/or anionic surfactants having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphthalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanyl-phosphatidylcholine, dipalmitoylphoshatidylcholine and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediamino-polypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having four hydrocarbon radicals optionally substituted with halo, phenyl, substituted phenyl or hydroxy; for instance quaternary ammonium salts containing as N-substituent at least one $C_8$-$C_{22}$ alkyl radical (e.g. cetyl, lauryl, palmityl, myristyl, oleyl and the like) and, as further substituents, unsubstituted or halogenated lower alkyl, benzyl and/or hydroxy-$C_{1-4}$ alkyl radicals. A more detailed description of surface-active agents suitable for this purpose may be found for instance in "McCutcheon's Detergents and Emulsifiers Annual" (MC Publishing Crop., Ridgewood, N.J. 1981), "Tensid-Taschenbuch", $2^{nd}$ ed. (Hanser Verlag, Vienna, 1981) and "Encyclopaedia of Surfactants" (Chemical Publishing Co., New York, 1981). Structure-forming, thickening or gel-forming agents may be included into the pharmaceutical compositions and combined preparations of the invention. Suitable such agents are in particular highly dispersed silicic acid, such as the product commercially available under the trade name Aerosil; bentonites; tetraalkyl ammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antisettle).

Gelling agents which may be included into the pharmaceutical compositions and combined preparations of the present invention include, but are not limited to, cellulose derivatives such as carboxymethylcellulose, cellulose acetate and the like; natural gums such as arabic gum, xanthum gum, tragacanth gum, guar gum and the like; gelatin; silicon dioxide; synthetic polymers such as carbomers, and mixtures thereof. Gelatin and modified celluloses represent a preferred class of gelling agents.

Other optional excipients which may be included in the pharmaceutical compositions and combined preparations of the present invention include additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzylalcohol, methyl paraben, propyl paraben and the like; sequestering agents such as ethylene-diamine tetraacetic acid; flavoring agents such as natural vanillin; buffers such as citric acid and acetic acid; extenders or bulking agents such as silicates, diatomaceous earth, magnesium oxide or aluminum oxide; densification agents such as magnesium salts; and mixtures thereof. Additional ingredients may be included in order to control the duration of action of the biologically-active ingredient in the compositions and combined preparations of the invention. Control release compositions may thus be achieved by selecting appropriate polymer carriers such as for example polyesters, polyamino-acids, polyvinyl-pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethyl-cellulose, polymethyl methacrylate and the other above-described polymers. Such methods include colloid drug delivery systems including, but not limited to, liposomes, microspheres, microemulsions, nanoparticles, nanocapsules and so on. Depending on the route of administration, the pharmaceutical composition or combined preparation of the invention may also require protective coatings.

Pharmaceutical forms suitable for injectable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol, complexing agents such as cyclodextrins and the like, and mixtures thereof. Other modes of local drug administration can also be used. For example, the selected active agent may be administered by way of intracavernosal injection, or may be administered topically, in an ointment, gel or the like, or transdermal, including transscrotally, using a conventional transdermal drug delivery system. Intracavernosal injection can be carried out by use of a syringe or any other suitable device. An example of a hypodermic syringe useful herein is described in U.S. Pat. No. 4,127,118, injection being made on the dorsum of the penis by placement of the needle to the side of each dorsal vein and inserting it deep into the corpora.

Another embodiment of this invention includes the various precursor or "prodrug" forms of the compounds of the present invention. It may be desirable to formulate the compounds of the present invention in the form of a chemical species which itself is not significantly biologically active, but which when delivered to the body of a human being or higher mammal will undergo a chemical reaction catalyzed by the normal function of the body, inter alia, enzymes present in the stomach or in blood serum, said chemical reaction having the effect of releasing a compound as defined herein. The term "prodrug" or "pro-drug" thus relates to these species which are converted in vivo into the active pharmaceutical ingredient.

The pro-drugs of the present invention can have any form suitable to the formulator, for example, esters are non-limiting common pro-drug forms. In the present case, however, the pro-drug may necessarily exist in a form wherein a covalent bond is cleaved by the action of an enzyme present at the target locus. For example, a C—C covalent bond may be selectively cleaved by one or more enzymes at said target locus and, therefore, a pro-drug in a form other than an easily hydrolysable precursor, inter alia an ester, an amide, and the like, may be used.

For the purposes of the present invention the term "therapeutically suitable pro-drug" is defined herein as a compound modified in such a way as to be transformed in vivo to the therapeutically active form, whether by way of a single or by multiple biological transformations, when in contact with the tissues of humans or mammals to which the pro-drug has been administered, and without undue toxicity, irritation, or allergic response, and achieving the intended therapeutic outcome. The present invention will be further described with reference to certain more specific embodiments and examples, but the present invention is not limited thereto. The following examples are given by way of illustration only.

As used herein with respect to a substituting radical, and unless otherwise stated, the term "$C_{1-7}$ alkyl" means straight and branched chain saturated acyclic hydrocarbon monovalent radicals having from 1 to 7 carbon atoms such as, for example, methyl, ethyl, propyl, n-butyl, 1-methylethyl (isopropyl), 2-methylpropyl (isobutyl), 1,1-dimethylethyl (terbutyl), 2-methylbutyl, n-pentyl, dimethylpropyl, n-hexyl, 2-methylpentyl, 3-methylpentyl, n-heptyl and the like. By analogy, the term "$C_{1-2}$ alkyl" refers to such radicals having from 1 to 2 carbon atoms, i.e. including methyl and ethyl. By analogy, the term "$C_{1-4}$ alkyl" refers to such radicals having from 1 to 4 carbon atoms, i.e. up to and including butyl. By analogy, the term "$C_{1-12}$ alkyl" refers to such radicals having from 1 to 12 carbon atoms, i.e. up to and including dodecyl.

As used herein with respect to a substituting radical, and unless otherwise stated, the term "$C_{1-7}$ alkylene" means the divalent hydrocarbon radical corresponding to the above defined $C_{1-7}$ alkyl, such as methylene, bis(methylene), tris (methylene), tetramethylene, hexamethylene and the like.

As used herein with respect to a substituting radical, and unless otherwise stated, the term "$C_{3-10}$ cycloalkyl" means a mono- or polycyclic saturated hydrocarbon monovalent radical having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

As used herein with respect to a substituting radical, and unless otherwise stated, the term "$C_{3-10}$ cycloalkyl-alkyl" refers to an aliphatic saturated hydrocarbon monovalent radical (preferably a $C_{1-7}$ alkyl such as defined above) to which a $C_{3-10}$ cycloalkyl (such as defined above) is already linked such as, but not limited to, cyclohexylmethyl, cyclopentylmethyl and the like.

As used herein with respect to a substituting radical, and unless otherwise stated, the term "$C_{3-10}$ cycloalkylene" means the divalent hydrocarbon radical corresponding to the above defined $C_{3-10}$ cycloalkyl.

As used herein with respect to a substituting radical, and unless otherwise stated, the term "aryl" designate any mono- or polycyclic aromatic monovalent hydrocarbon radical having from 6 up to 30 carbon atoms such as but not limited to phenyl, naphthyl, anthracenyl, phenantracyl, fluoranthenyl, chrysenyl, pyrenyl, biphenylyl, terphenyl, picenyl, indenyl, biphenyl, indacenyl, benzocyclobutenyl, benzocyclooctenyl and the like, including fused benzo-$C_4$-β cycloalkyl radicals (the latter being as defined above) such as, for instance, indanyl, tetrahydronaphtyl, fluorenyl and the like, all of the said radicals being optionally substituted with one or more substituents independently selected from the group consisting of halogen, amino, trifluoromethyl, hydroxyl, sulfhydryl and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein, e.g. with respect to a substituting radical such as the combination of substituents in certain positions of isothiazolo[4,3-b]pyridine ring together with the carbon atoms in the same positions of said ring, and unless otherwise stated, the term "homocyclic" means a mono- or polycyclic, saturated or mono-unsaturated or polyunsaturated hydrocarbon radical having from 4 up to 15 carbon atoms but including no heteroatom in the said ring; for instance said combination of substituents may form a $C_{2-6}$ alkylene radical, such as tetramethylene, which cyclizes with the carbon atoms in certain positions of the isothiazolo[4,3-b]pyridine ring.

As used herein with respect to a substituting radical (including the combination of substituents in certain positions of the isothiazolo[4,3-b]pyridine ring together with the carbon atoms in the same positions of said ring), and unless otherwise stated, the term "heterocyclic" means a mono- or polycyclic, saturated or mono-unsaturated or polyunsaturated monovalent hydrocarbon radical having from 2 up to 15 carbon atoms and including one or more heteroatoms in one or more heterocyclic rings, each of said rings having from 3 to 10 atoms (and optionally further including one or more heteroatoms attached to one or more carbon atoms of said ring, for instance in the form of a carbonyl or thiocarbonyl or selenocarbonyl group, and/or to one or more heteroatoms of said ring, for instance in the form of a sulfone, sulfoxide, N-oxide, phosphate, phosphonate or selenium oxide group), each of said heteroatoms being independently selected from the group consisting of nitrogen, oxygen, sulfur, selenium and phosphorus, also including radicals wherein a heterocyclic ring is fused to one or more aromatic hydrocarbon rings for instance in the form of benzo-fused, dibenzo-fused and naphto-fused heterocyclic radicals; within this definition are included heterocyclic radicals such as, but not limited to, diazepinyl, oxadiazinyl, thiadiazinyl, dithiazinyl, triazolonyl, diazepinonyl, triazepinyl, triazepinonyl, tetrazepinonyl, benzoquinolinyl, benzothiazinyl, benzothiazinonyl, benzoxa-thiinyl, benzodioxinyl, benzodithiinyl, benzoxazepinyl, benzothiazepinyl, benzodiazepine, benzodioxepinyl, benzodithiepinyl, benzoxazocinyl, benzo-thiazocinyl, benzodiazocinyl, benzoxathiocinyl, benzodioxocinyl, benzotrioxepinyl, benzoxathiazepinyl, benzoxadiazepinyl, benzothia-diazepinyl, benzotriazepinyl, benzoxathiepinyl, benzotriazinonyl, benzoxazolinonyl, azetidinonyl, azaspiroundecyl, dithiaspirodecyl, selenazinyl, selenazolyl, selenophenyl, hypoxanthinyl, azahypo-xanthinyl, bipyrazinyl, bipyridinyl, oxazolidinyl, diselenopyrimidinyl, benzodioxocinyl, benzopyrenyl, benzopyranonyl, benzophenazinyl, benzoquinolizinyl, dibenzo-carbazolyl, dibenzoacridinyl, dibenzophenazinyl, dibenzothiepinyl, dibenzoxepinyl, dibenzopyranonyl, dibenzoquinoxalinyl, dibenzothiazepinyl, dibenzisoquinolinyl, tetraazaadamantyl, thiatetraazaadamantyl, oxauracil, oxazinyl, dibenzothiophenyl, dibenzofuranyl, oxazolinyl, oxazolonyl, azaindolyl, azolonyl, thiazolinyl, thiazolonyl, thiazolidinyl, thiazanyl, pyrimidonyl, thiopyrimidonyl, thiamorpholinyl, azlactonyl, naphtindazolyl, naphtindolyl, naphtothiazolyl, naphtothioxolyl, naphtoxindolyl, naphto-triazolyl, naphtopyranyl, oxabicycloheptyl, azabenzimidazolyl, azacycloheptyl, azacyclooctyl, azacyclononyl, azabicyclononyl, tetrahydrofuryl, tetrahydropyranyl, tetrahydro-pyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl (benzothiofuranyl), phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazirryl, tetrazinyl, trazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofutyl, furoyl, hydantoinyl, dioxolanyl, dioxolyl, dithianyl, dithienyl, dithiinyl, thienyl, indolyl, indazolyl, benzofutyl, quinolyl, quinazolinyl, quinoxalinyl, carbazolyl, phenoxazinyl, phenothiazinyl, xanthenyl, purinyl, benzothienyl, naphtothienyl, thianthrenyl,' pyranyl, pyronyl, benzopyronyl, isobenzofuranyl, chromenyl, phenoxathiinyl, indolizinyl, quinolizinyl, isoquinolyl, phthalazirryl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimi-dazolyl, pyrazolinyl, pyrazolidinyl, pyrrolinyl, pyrrolidinyl, piperazinyl, uridinyl, thymidinyl, cytidinyl, azirinyl, aziridinyl, diazirinyi, diaziridinyl, oxiranyl, oxaziridinyl, dioxiranyl, thiiranyl, azetyl, dihydroazetyl, azetidinyl, oxetyl, oxetanyl, oxetanonyl, homopiperazinyl, homopiperidinyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzocarbazolyl, benzochromonyl, benzisoalloxazinyl, benzocoumarinyl, thiocoumarinyl, pheno-metoxazinyl, phenoparoxazinyl, phentriazinyl, thiodiazinyl, thiodiazolyl, indoxyl, thioindoxyl, benzodiazinyl (e.g. phtalazinyl), phtalidyl, phtalimidinyl, phtalazonyl, alloxazinyl, dibenzopyronyl (i.e. xanthonyl), xanthionyl, isatyl, isopyrazolyl, isopyrazolonyl, urazolyl, urazinyl, uretinyl, uretidinyl, succinyl, succinimido, benzylsulfinyl, benzylsulfanyl and the like, including all possible isomeric forms thereof, wherein each carbon atom of said heterocyclic ring may furthermore be independently substituted with a substituent selected from the group consisting of halogen, nitro, $C_{1-7}$ alkyl (optionally containing one or more functions or radicals selected from the group consisting of carbonyl (oxo), alcohol (hydroxyl), ether (alkoxy), acetal, amino, imino, oximino, alkyloximino, amino-acid, cyano, carboxylic acid ester or amide, nitro, thio $C_{1-7}$ alkyl, thio $C_{3-10}$ cycloalkyl, $C_{1-7}$ alkylamino, cycloalkylamino, alkenylamino, cycloalkenylamino, alkynylamino, arylamino, arylalkyl-amino, hydroxylalkylamino, mercaptoalkylamino, heterocyclic-substituted alkylamino, heterocyclic amino, heterocyclic-substituted arylamino, hydrazino, alkyihydrazino, phenyihydrazino, sulfonyl, sulfonamido and halogen), $C_{3-7}$ alkenyl, $C_{2-7}$ alkynyl, halo $C_{1-7}$ alkyl, $C_{3-10}$ cycloalkyl, aryl, arylalkyl, alkylaryl, alkylacyl, arylacyl, hydroxyl, amino, $C_{1-7}$ alkylamino, cycloalkylamino, alkenylamino, cycloalkenylamino, alkynylamino, arylamino, arylalkylamino, hydroxyalkylamino, mercaptoalkylamino, heterocyclic-substituted alkylamino, heterocyclic amino, heterocyclic-substituted arylamino, hydrazino, alkyihydrazino, phenyihydrazino, sulfhydryl, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thioheterocyclic, arylalkylthio, heterocyclic-substituted alkylthio, formyl, hydroxylamino, cyano, carboxylic acid or esters or thioesters or amides thereof, tricarboxylic acid or esters or thioesters or amides thereof; depending upon the number of unsaturations in the 3 to 10 atoms ring, heterocyclic radicals may be sub-divided into heteroaromatic (or "heteroaryl") radicals and non-aromatic heterocyclic radicals; when a heteroatom of said non-aromatic heterocyclic radical is nitrogen, the latter may be substituted with a substituent selected from the group consisting of $C_{1-7}$ alkyl, $C_{3-10}$ cycloalkyl, aryl, arylalkyl, alkylaryl and carboxylic acid ester.

As used herein with respect to a substituting radical, and unless otherwise stated, the terms "$C_{1-7}$ alkoxy", "$C_{3-10}$ cycloalkoxy", "aryloxy", "arylalkyloxy", "oxyheterocyclic", "thio $C_{1-7}$ alkyl", "thio $C_{3-10}$ cycloalkyl", "arylthio", "arylalkylthio" and "thioheterocyclic" refer to substituents wherein a carbon atom of a $C_{1-7}$ alkyl, respectively a $C_{3-10}$ cycloalkyl, aryl, arylalkyl or heterocyclic radical (each of them such as defined herein), is attached to an oxygen atom or a divalent sulfur atom through a single bond such as, but not limited to, methoxy, ethoxy, propoxy, butoxy, pentoxy, isopropoxy, sec-butoxy, tert-butoxy, isopentoxy, cyclopropyloxy, cyclobutyloxy, cyclopentyloxy, thiomethyl, thioethyl, thiopropyl, thiobutyl, thiopentyl, thiocyclopropyl, thiocyclobutyl, thiocyclopentyl, thiophenyl, phenyloxy, benzyloxy, mercaptobenzyl, cresoxy, and the like.

As used herein with respect to a substituting atom, and unless otherwise stated, the term "halogen" or "halo" means any atom selected from the group consisting of fluorine, chlorine, bromine and iodine.

As used herein with respect to a substituting radical, and unless otherwise stated, the term "halo $C_{1-7}$ alkyl" means a $C_{1-7}$ alkyl radical (such as above defined) in which one or more hydrogen atoms are independently replaced by one or more halogens (preferably fluorine, chlorine or bromine), such as but not limited to difluoromethyl, trifluoromethyl, trifluoroethyl, octafluoropentyl, dodecafluoroheptyl, dichloromethyl and the like.

As used herein with respect to a substituting radical, and unless otherwise stated, the terms "$C_{2-7}$ alkenyl" designate a straight and branched acyclic hydrocarbon monovalent radical having one or more ethylenic unsaturations and having from 2 to 7 carbon atoms such as, for example, vinyl, 1-propenyl, 2-propenyl (allyl), 1-butenyl, 2-butenyl, 2-pentenyl, 3-pentenyl, 3-methyl-2-butenyl, 3-hexenyl, 2-hexenyl, 2-heptenyl, 1,3-butadienyl, pentadienyl, hexadienyl, heptadienyl, heptatrienyl and the like, including all possible isomers thereof.

As used herein with respect to a substituting radical, and unless otherwise stated, the term "$C_{3-10}$ cycloalkenyl" means a monocyclic mono- or polyunsaturated hydrocarbon monovalent radical having from 3 to 8 carbon atoms, such as for instance cyclopropenyl, cyclobutenyl, cyclopentenyl, cyclopentadienyl, cyclohexenyl, cyclohexadienyl, cycloheptenyl, cyclohepta-dienyl, cycloheptatrienyl, cyclooctenyl, cyclooctadienyl and the like, or a $C_{7-10}$ polycyclic mono- or polyunsaturated hydrocarbon mono-valent radical having from 7 to 10 carbon atoms such as dicyclopentadienyl, fenchenyl (including all isomers thereof, such as α-pinolenyl), bicyclo[2.2.1]hept-2-enyl, bicyclo[2.2.1]hepta-2,5-dienyl, cyclo-fenchenyl and the like.

As used herein with respect to a substituting radical, and unless otherwise stated, the term "$C_{2-7}$ alkynyl" defines straight and branched chain hydrocarbon radicals containing one or more triple bonds and optionally at least one double bond and having from 2 to 7 carbon atoms such as, for example, acetylenyl, 1-propynyl, 2-propynyl, 1-butynyl, 2-butynyl, 2-pentynyl, 1-pentynyl, 3-methyl-2-butynyl, 3-hexynyl, 2-hexynyl, 1-penten-4-ynyl, 3-penten-1-ynyl, 1,3-hexadien-1-ynyl and the like.

As used herein with respect to a substituting radical, and unless otherwise stated, the terms "arylalkyl", "arylalkenyl" and "heterocyclic-substituted alkyl" refer to an aliphatic saturated or ethylenically unsaturated hydrocarbon monovalent radical (preferably a $C_{1-7}$ alkyl or $C_{2-7}$ alkenyl radical such as defined above) onto which an aryl or heterocyclic radical (such as defined above) is already bonded via a carbon atom, and wherein the said aliphatic radical and/or the said aryl or heterocyclic radical may be optionally substituted with one or more substituents independently selected from the group consisting of halogen, amino, hydroxyl, sulfhydryl, $C_{1-7}$ alkyl, $C_{1-7}$ alkoxy, trifluoromethyl and nitro, such as but not limited to benzyl, 4-chlorobenzyl, 4-fluorobenzyl, 2-fluorobenzyl, 3,4-dichlorobenzyl, 2,6-dichlorobenzyl, 3-methylbenzyl, 4-methylbenzyl, 4-ter-butylbenzyl, phenylpropyl, 1-naphthylmethyl, phenylethyl, 1-amino-2-phenylethyl, 1-amino-2-[4-hydroxy-phenyl]ethyl, 1-amino-2-[indol-2-yl]ethyl, styryl, pyridylmethyl (including all isomers thereof), pyridylethyl, 2-(2-pyridyl)isopropyl, oxazolylbutyl, 2-thienylmethyl, pyrrolylethyl, morpholinylethyl, imidazol-1-yl-ethyl, benzodioxolylmethyl and 2-furylmethyl.

As used herein with respect to a substituting radical, and unless otherwise stated, the terms "alkylaryl" and "alkyl-substituted heterocyclic" refer to an aryl or, respectively, heterocyclic radical (such as defined above) onto which are bonded one or more aliphatic saturated or unsaturated hydrocarbon monovalent radicals, preferably one or more $C_{1-7}$ alkyl, $C_{2-7}$ alkenyl or $C_{3-10}$ cycloalkyl radicals as defined above such as, but not limited to, o-toluyl, m-toluyl, p-toluyl, 2,3-xylyl, 2,4-xylyl, 3,4-xylyl, o-cumenyl, m-cumenyl, p-cumenyl, o-cymenyl, m-cymenyl, p-cymenyl, mesityl, fer-butylphenyl, lutidinyl (i.e. dimethylpyridyl), 2-methylaziridinyl, methyl-benzimidazolyl, methylbenzofuranyl, methylbenzothiazolyl, methylbenzotriazolyl, methylbenzoxazolyl and methylbenzselenazolyl.

As used herein with respect to a substituting radical, and unless otherwise stated, the term "alkoxyaryl" refers to an aryl radical (such as defined above) onto which is (are) bonded one or more $C_{1-7}$ alkoxy radicals as defined above, preferably one or more methoxy radicals, such as, but not limited to, 2-methoxyphenyl, 3-methoxyphenyl, 4-methoxyphenyl, 3,4-dimethoxyphenyl, 2,4,6-trimethoxyphenyl, methoxynaphtyl and the like.

As used herein with respect to a substituting radical, and unless otherwise stated, the terms "alkylamino", "cycloalkylamino", "alkenylamino", "cyclo-alkenylamino", "arylamino", "arylalkylamino", "heterocyclic-substituted alkylamino", "heterocyclic-substituted arylamino", "heterocyclic amino", "hydroxy-alkylamino", "mercaptoalkylamino" and "alkynylamino" mean that respectively one (thus monosubstituted amino) or even two (thus disubstituted amino) $C_{1-7}$ alkyl, $C_{3-10}$ cycloalkyl, $C_{2-7}$ alkenyl, $C_{3-10}$ cycloalkenyl, aryl, arylalkyl, heterocyclic-substituted alkyl, heterocyclic-substituted aryl, heterocyclic (provided in this case the nitrogen atom is attached to a carbon atom of the heterocyclic ring), mono- or polyhydroxy $C_{1-7}$ alkyl, mono- or polymercapto $C_{1-7}$ alkyl, or $C_{2-7}$ alkynyl radical(s) (each of them as defined herein, respectively, and including the presence of optional substituents independently selected from the group consisting of halogen, amino, hydroxyl, sulfhydryl, $C_{1-7}$ alkyl, $C_{1-7}$ alkoxy, trifluoromethyl and nitro) is/are attached to a nitrogen atom through a single bond such as, but not limited to, anilino, 2-bromoanilino, 4-bromoanilino, 2-chloroanilino, 3-chloroanilino, 4-chloroanilino, 3-chloro-4-methoxyanilino, 5-chloro-2-methoxyanilino, 2,3-dimethylanilino, 2,4-dimethylanilino, 2,5-dimethylanilino, 2,6-dimethylanilino, 3,4-dimethylanilino, 2-fluoroanilino, 3-fluoroanilino, 4-fluoroanilino, 3-fluoro-2-methoxyanilino, 3-fluoro-4-methoxyanilino, 2-fluoro-4-methylanilino, 2-fluoro-5-methylanilino, 3-fluoro-2-methylanilino, 3-fluoro-4-methylanilino, 4-fluoro-2-methylanilino, 5-fluoro-2-methylanilino, 2-iodoanilino, 3-iodoanilino, 4-iodoanilino, 2-methoxy-5-methylanilino, 4-methoxy-2-methylanilino, 5-methoxy-2-methylanilino, 2-ethoxyanilino, 3-ethoxy-anilino, 4-ethoxyanilino, benzylamino, 2-methoxybenzylamino, 3-methoxybenzylamino, 4-methoxybenzylamino, 2-fluorobenzylamino, 3-fluorobenzylamino, 4-fluoro-benzylamino, 2-chlorobenzylamino, 3-chlorobenzylamino, 4-chlorobenzylamino, 2-aminobenzylamino, diphenylmethylamino, α-naphthylamino, methylamino, dimethylamino, ethylamino, diethylamino, isopropylamino, propenylamino, n-butylamino, ter-butylamino, dibutylamino, 1,2-diaminopropyl, 1,3-diaminopropyl, 1,4-diaminobutyl, 1,5-diaminopentyl, 1,6-diaminohexyl, morpholinomethylamino, 4-morpholinoanilino, hydroxymethylamino, β-hydroxyethylamino and ethynylamino; this definition also includes mixed disubstituted amino radicals wherein the nitrogen atom is attached to two such radicals belonging to two different sub-sets of radicals, e.g. an alkyl radical and an alkenyl radical, or to two different radicals within the same subset of radicals, e.g. methylethylamino; among di-substituted amino radicals, symmetrically-substituted amino radicals are more easily accessible and thus usually preferred from a standpoint of ease of preparation.

As used herein with respect to a substituting radical, and unless otherwise stated, the terms "(thio)carboxylic acid-ester", "(thio)carboxylic acid thioester" and "(thio)carboxylic acid amide" refer to radicals wherein the carboxyl or thiocarboxyl group is bonded to the hydrocarbonyl residue of an alcohol, a thiol, a polyol, a phenol, a thiophenol, a primary or secondary amine, a polyamine, an amino-alcohol or ammonia, the said hydrocarbonyl residue being selected from the group consisting of alkyl, alkenyl, alkynyl, cycloalkyl, cycloalkenyl, aryl, arylalkyl, alkylaryl, alkylamino, cycloalkylamino, alkenylamino, cycloalkenylamino, arylamino, arylalkylamino, heterocyclic-substituted alkylamino, heterocyclic amino, heterocyclic-substituted arylamino, hydroxyalkylamino, mercaptoalkylamino or alkynylamino (such as above defined, respectively).

As used herein with respect to a substituting radical, and unless otherwise stated, the term "amino-acid" refers to a radical derived from a molecule having the chemical formula $H_2N$—CHR—COOH, wherein R is the side group of atoms characterising the amino-acid type; said molecule may be one of the 20 naturally-occurring amino-acids or any similar non naturally-occurring amino-acid.

As used herein and unless otherwise stated, the term "stereoisomer" refers to all possible different isomeric as well as conformational forms which the compounds of formula (I) may possess, in particular all possible stereochemical and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a isothiazolo[4,3-b]pyridine derivative of this invention with a suitable inorganic solvent (e.g. hydrates) or organic solvent, such as but not limited to alcohols, ketones, esters, ethers, nitriles and the like.

Dose response curves of the GAK inhibitors' (Compound Example 49 (49) and Compound Example 50 (50)) effects on infection of Huh-7.5 cells with cell culture grown HCV (HCVcc) (A), entry of pseudoparticles of HCV (HCVpp) (B), HCV RNA replication 72 hours postelectroporation with J6/JFH(p7-Rluc2A) RNA (C), and intra-(D) and extra-cellular (E) infectivity in naive cells inoculated with cell lysates or supernatants derived from the electroporated cells, respectively. Plotted in black (left y-axes) are relative luciferase values normalized to DMSO treated controls. Corresponding cellular viability, as measured by alamarBlue-based assays, are plotted in grey (right y-axes). Data reflect means and s.d. (error bars). F. The effect of the inhibitors on AP2M1 phosphorylation by Western analysis in lysates derived from Huh-7.5 cells. A representative membrane blotted with anti-phospho-AP2M1 (p-AP2M1) and anti-AP2M1 antibodies is shown. Numbers represent relative p-AP2M1/total AP2M1 protein ratio normalized to DMSO controls.

Figure 2:
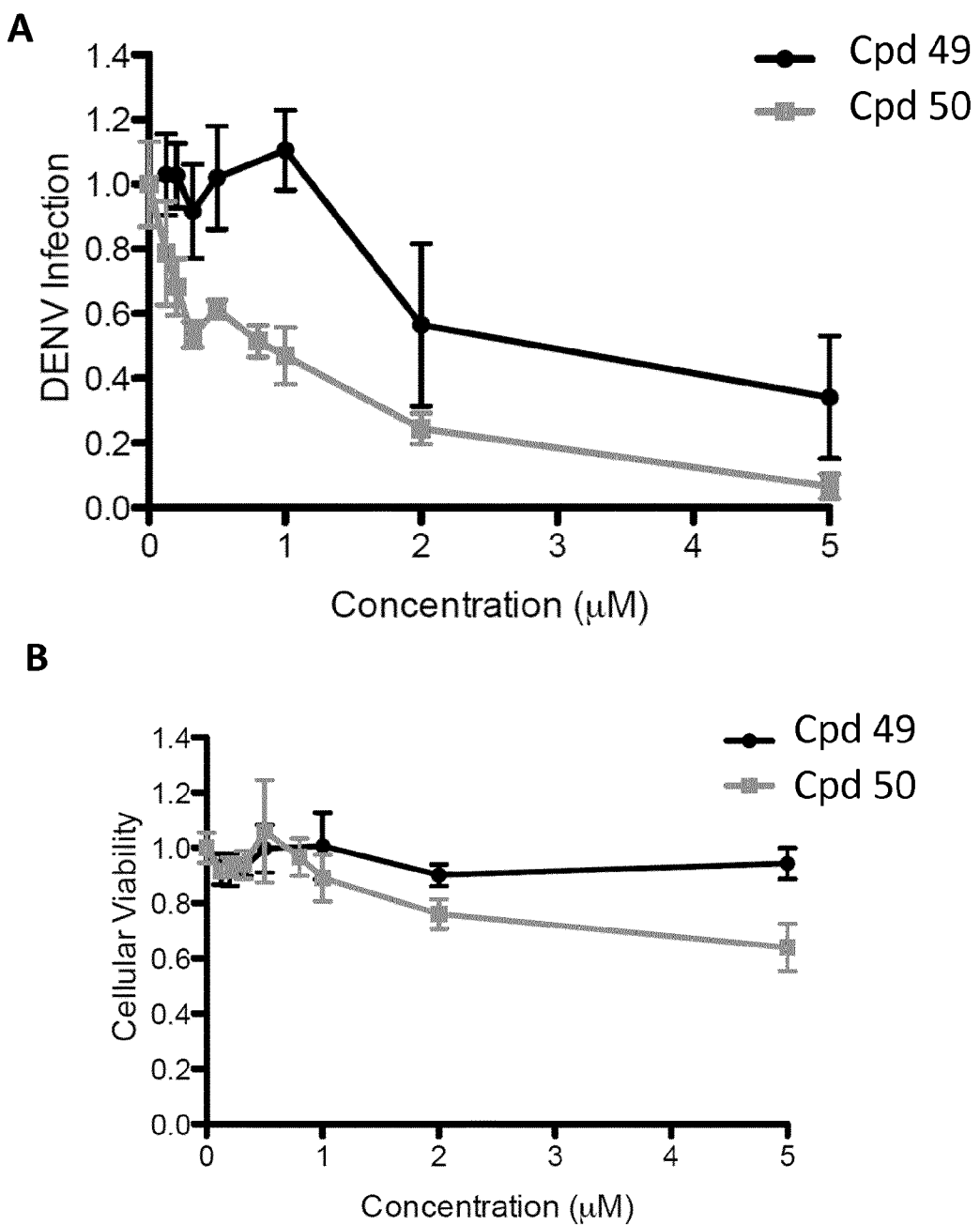

FIG. 2: Pharmacological inhibition of DENV infection

A. Dose response curves of the GAK inhibitors' (Compound Example 49 and Compound Example 50) effects on infection of Huh-7 cells with cell culture grown DENV. Infection was measured by *Renilla* luciferase assays following 72 hours of daily treatment and expressed relative to DMSO controls.

B. Cellular viability following daily treatment of DENV infected Huh-7 cells with the inhibitors for 72 hours, as measured by alamarBlue-based assay.

All treatments with cpd 49 are plotted in black and those with cpd 50 are plotted in grey. Data are normalized to vehicle control (DMSO). Data represent means and s.d. (error bars) from at least three experiments in triplicates.

Figure 3:
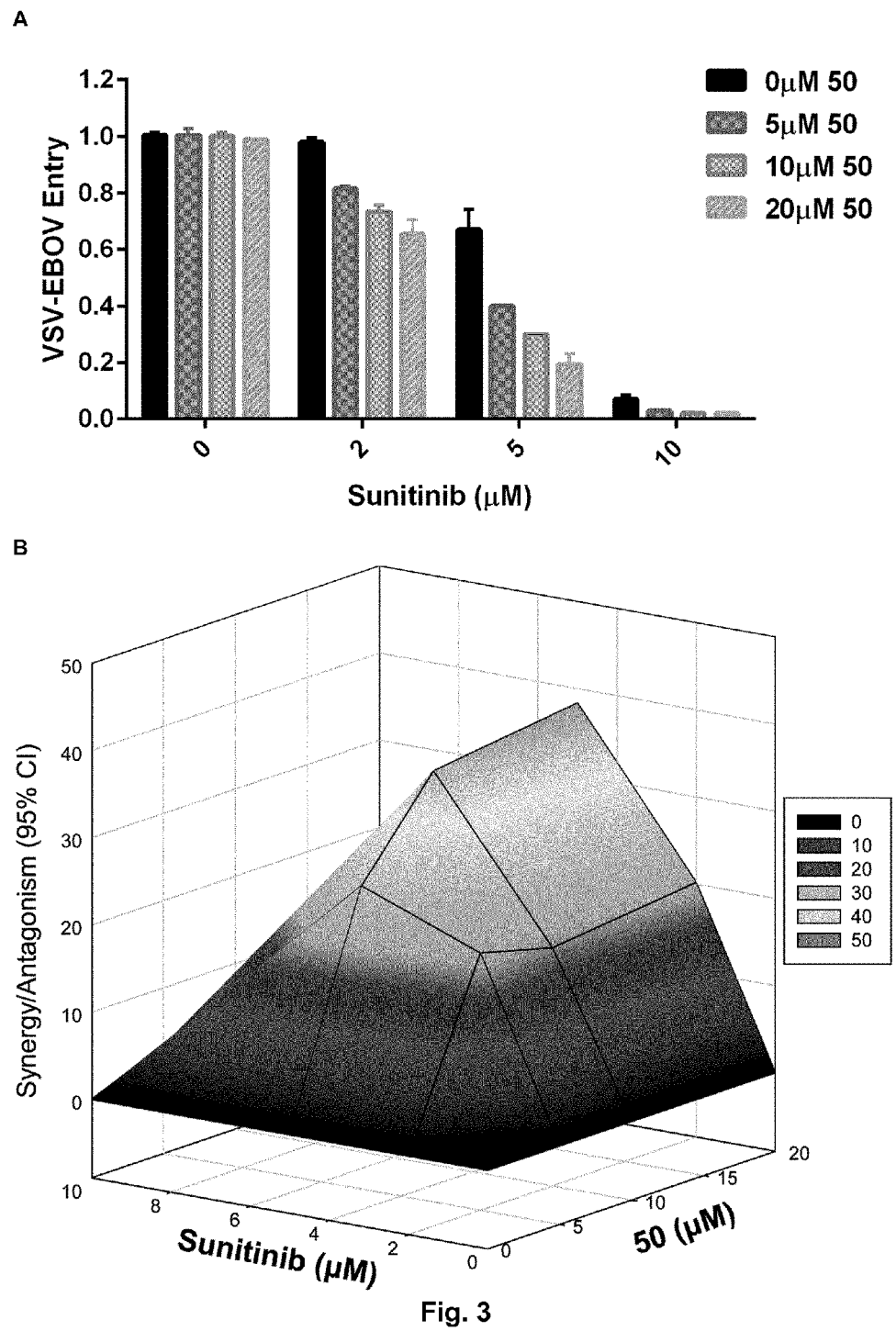

FIG. 3: Effect of combinations of GAK inhibitor of example 50 ("50") with sunitinib on Ebola virus entry Dose response curves of cpd 50 with Sunitinib on infection of Vero cells (African green monkey kidney cells) with VSV-EB GFP-reporter virus (VSV bearing surface glycoprotein of EBOV). (A): entry of VSV-EBOV and (B): differential surface analysis at the 95% confidence level (CI). Peaks above the theoretical additive plane indicate synergy, whereas depressions below it indicate antagonism. The level of synergy is as indicated by the grey scale on FIG. 3B. Results for drug treated samples were normalized to vehicle control and represented as relative fractions of infected/GFP positive cells. Sunitinib was tested in the concentration range from 0 μM to 10 μM, and compound "50" was tested in the range from 0 μM to 20 μM.

EXAMPLES

General

For all reactions, analytical grade solvents were used. All moisture-sensitive reactions were carried out in oven-dried glass-ware (135° C.). $^1$H-NMR spectra were recorded on a Bruker Advance 300 ($^1$H-NMR: 300 MHz) using tetramethylsilane as internal standard for $^1$H-NMR spectra. Abbreviations used are: s=singlet, d=doublet, t=triplet, q=quartet, m=multiplet, br s=broad signal. Coupling constants are expressed in Hz. Precoated aluminum sheets (Fluka Silica gel/TLC-cards, 254 nm) were used for TLC. Column chromatography (CC) was performed on ICN silica gel 63-200, 60 Å.

Example 1

Synthesis of
3-amino-5-bromopyridine-2-carbonitrile

A solution of iron powder (3.36 g, 60 mmol) in acetic acid (15 ml) was stirred at 0° C. To this solution was added dropwise a solution of 3-nitro-5-bromopyridine-2-carbonitrile (2.51 g, 11 mmol) In acetic acid (15 ml). The reaction mixture was stirred at room temperature for two hours. Then, ethyl acetate (300 ml) was added and the mixture was filtered (paper filter). The filter cake was washed with ethylacetate. The filtrate was evaporated and partitioned between ethylacetate (500 ml) and water (250 ml). The organic phase was washed with a 1 N NaOH solution (ca. 200 ml). The combined organic phases were dried and evaporated in vacuo, yielding a mixture of two compounds, i.e. 3-amino-5-bromopyridine-2-carbonitrile (major compound) and 3-amino-5-bromopyridine-2-carboxamide (minor compound). This mixture was used as such in the next reaction.

Example 2

Synthesis of
3-amino-5-bromo-2-pyridinecarbothioamide

To a solution of a mixture of 3-amino-5-bromopyridine-2-carbonitrile and 3-amino-5-bromopyridine-2-carboxamide (crude from example 1) in ethanol (25 ml) was added phosphorus pentasulfide (2 eq; 4.84 g). The mixture was heated overnight at 75° C. The solvents were evaporated and the crude residue was purified by flash chromatography on silica, using a mixture of cyclohexane/ethyl acetate (in a ratio of 7:1) as mobile phase, yielding the title compound (3.36 gram crude).

Example 3

3-amino-6-bromo-isothiazolo[4,3-b]pyridine

To a solution of 3-amino-5-bromo-2-pyridinecarbothioamide (as obtained in Example 2) in methanol (50 ml) was added dropwise a 30% $H_2O_2$ solution in water (3.5 ml) at 0° C. The reaction mixture was stirred overnight at room temperature and then cooled again to 0° C. The crystals were filtered off and washed with cold methanol yielding the title compound (1.6 g, 63%).

Examples 4-8

Synthesis of
3-amino-6-aryl-isothiazolo[4,3-b]pyridines

General Procedure

To a solution of 3-amino-6-bromo-isothiazolo[4,3-b]pyridine (166 mg, 0.72 mmol) in mixture of dioxane (10 ml) and water (1.5 ml) was added an appropriate boronic acid (2 eq), sodium carbonate (2 eq, 153 mg) and Pd(dppf)Cl$_2$ (0.1 eq, 59 mg) The reaction mixture was stirred overnight at 100° C. The reaction mixture was cooled down to room temperature and the reaction was partioned between ethylacetate (60 ml) and brine (30 ml). The aqueous phase was then extracted with ethyl acetate (40 ml). The combined organic phases were dried over MgSO$_4$ and evaporated in vacuo. The residue was purified by flash chromatography on silicagel yielding the pure title compounds.

The following compounds were made according to this procedure:

Example 4

3-amino-6-phenyl-isothiazolo[4,3-b]-pyridine

This compound was obtained using phenylboronic acid and the crude residue was purified by flash chromatography using a mixture of cyclohexane and ethylacetate (in a ratio of 4:1) as mobile phase, affording the title compound in 77% yield.

Example 5

3-amino-6-(3-pyridyl)-isothiazolo[4,3-b]pyridine

This compound was obtained using 3-pyridylboronic acid and the crude residue was purified by flash chromatography using a mixture of methanol and dichloromethane (in a ratio of 1:20) as mobile phase, affording the title compound in 75% yield.

$^1$H-NMR (300 MHz, DMSO-d$_6$): δ=7.52 (m, 1H, arom H), 7.95 (br s, 2H, NH$_2$), 8.02 (d, J=1.98 Hz, 1H, arom H), 8.24 (m, 1H, arom H), 8.66 (m, 2H, arom H), 9.03 (d, J=1.98 Hz, 1H, arom H) ppm.

Example 6

3-amino-6-(3,4-dimethoxyphenyl)-isothiazolo[4,3-b]pyridine

This compound was obtained using 3,4-dimethoxyphenylboronic acid and the crude residue was purified by flash chromatography using a mixture of methanol and dichloromethane (in a ratio of 1:40) as mobile phase, affording the title compound in 57% yield.

$^1$H-NMR (300 MHz, DMSO-d$_6$): δ=3.81 (s, 3H, OCH$_3$), 3.88 (s, 3H, OCH$_3$), 7.07 (d, J=8.89 Hz, 1H, arom H), 7.35 (m, 2H, arom H), 7.84 (br s, 2H, NH$_2$), 7.89 (d, J=1.92 Hz, 1H, arom H), 8.63 (d, J=1.95 Hz, 1H, arom H) ppm.

Example 7

3-amino-6-(4-fluorophenyl)-isothiazolo[4,3-b]pyridine

This compound was obtained using 4-fluorophenylboronic acid and the crude residue was purified by flash chromatography using a mixture of cyclohexane and ethylacetate (in a ratio of 4:1) as mobile phase, affording the title compound in 76% yield.

$^1$H-NMR (300 MHz, DMSO-d$_6$): δ=6.36 (br s, 2H, NH$_2$), 7.34 (m, 2H, arom H), 7.38 (d, J=3.1 Hz, 1H, arom H), 7.71 (m, 2H, arom H), 8.17 (d, J=1.92 Hz, 1H, arom H) ppm.

Example 8

3-amino-6-(3-thienyl)-isothiazolo[4,3-b]pyridine

This compound was obtained using 3-thienylboronic acid and the crude residue was purified by flash chromatography using a mixture of cyclohexane and ethylacetate (in a ratio of 3:2) as mobile phase, affording the title compound in 69% yield.

$^1$H-NMR (300 MHz, DMSO-d$_6$): δ=7.70 (m, 2H, arom H), 7.84 (br s, 2H, NH$_2$), 7.98 (d, J=1.89 Hz, 1H, arom H), 8.17 (q, J=1.32 Hz, 1H, arom H), 8.74 (d, J=1.95 Hz, 1H, arom H) ppm.

Example 9

Synthesis of 3,6-di-bromo-isothiazolo[4,3-b]pyridine

To a solution of 3-amino-6-bromo-isothiazolo[4,3-b]pyridine (115 mg, 0.5 mmol) in HBr (7 ml) at 0° C. was added portionwise sodium nitrite (3 eq, 104 mg). After 30 minutes, CuBr (2 eq, 144 mg) was added. The reaction mixture was stirred for two hours at 0° C. and then overnight at room temperature. The mixture was neutralized with solid potassium carbonate and extracted with ethyl acetate (2×15 ml). The combined organic phases were dried over MgSO$_4$ and evaporated in vacuo. The crude residue was purified by silicagel flash chromatography, the mobile phase being a mixture of cyclohexane and ethylacetate (in a ratio of 30:1), yielding the pure title compound (111 mg, 76%).

Example 10

Synthesis of 6-bromo-3-benzylamino-isothiazolo[4,3-b]pyridine

To a solution of 3,6-di-bromo-isothiazolo[4,3-b]pyridine (54 mg, 0.18 mmol) in ethanol (5 ml) was added benzylamine (3 eq, 61 μl). The reaction was stirred overnight at 75° C. The solvent was evaporated in vacuo the crude residue was purified by silicagel flash chromatography, the mobile phase being a mixture of cyclohexane and ethylacetate (in a ratio of 5:1), yielding the pure title compound (25 mg, 25%).

Examples 11-13

Synthesis of 6-bromo-3-substituted-isothiazolo[4,3-b]pyridines

General Procedure

To a solution of 3,6-di-bromo-isothiazolo[4,3-b]pyridine (150 mg, 0.51 mmol) in ethanol (10 ml) was added an appropriate nitrogen nucleophile (3 eq). The reaction was stirred overnight at 75° C. The solvent was evaporated in vacuo and the crude residue was purified by silicagel flash chromatography, the mobile phase being a mixture of cyclohexane and ethylacetate (in a ratio of 4:1), yielding the pure title compounds.

The following compounds were made according to this procedure:

Example 11

6-bromo-3-morpholino-isothiazolo[4,3-b]pyridine

This compound was made using morpholine as nucleophile and the crude residue was purified using a mixture of cyclohexane and ethylacetate (in a ratio of 4:1) as mobile phase, affording the title compound in 92% yield.

$^1$H-NMR (300 MHz, DMSO-d$_6$): δ=3.84 (br s, 4H, 2×NCH$_2$), 3.87 (br s, 4H, 2×OCH$_2$), 8.15 (s, 1H, arom H), 8.37 (s, 1H, arom H) ppm.

Example 12

6-bromo-6-ethanolamino-isothiazolo[4,3-b]pyridine

This compound was made using ethanolamine as nucleophile and the crude residue was purified using a mixture of cyclohexane and ethylacetate (in a ratio gradually ranging from 1:1 to 1:4) as mobile phase, affording the title compound in 94% yield.

$^1$H-NMR (300 MHz, DMSO-d$_6$): δ=3.39 (q, J=5.75 Hz, 2H, NCH$_2$), 3.68 (q, J=5.68 Hz, 2H, OCH$_2$), 4.91 (t, J=5.57 Hz, 1H), 8.04 (d, J=2.01 Hz, 1H, arom H), 8.29 (d, J=1.98 Hz, 1H, arom H), 8.66 (t, J=5.78 Hz, 1H) ppm.

Example 13

6-bromo-3-(N-methyl-piperazino-isothiazolo[4,3-b]pyridine

This compound was made using N-methyl-piperazine as nucleophile and the crude residue was purified using a mixture of methanol and dichloromethane (in a ratio of 3:100) as mobile phase, affording the title compound in 92% yield.

$^1$H-NMR (300 MHz, DMSO-d$_6$): δ=2.24 (s, 3H, NCH$_3$), 2.52 (m, 4H, 2×NCH$_2$), 3.88 (t, J=Hz, 4H, 2×NCH$_2$), 8.12 (d, J=2.01 Hz, 1H, arom H), 8.36 (d, J=1.23 Hz, 1H, arom H) ppm.

Example 14

Synthesis of 3-methoxy-6-bromo-isothiazolo[4,3-b]pyridine

To a solution of 3,6-dibromo-isothiazolo[4,3-b]pyridine (700 mg, 2.38 mmol) in absolute methanol (50 ml) was added carefully at 0° C. sodium methoxide (2.5 eq, 322 mg) in small portions. The resulting reaction mixture was stirred overnight at room temperature and then heated at 55° C. for 8 hours. The reaction was cooled down to room temperature, neutralized with a 5% HCl solution and evaporated in vacuo. The residue was divided between ethyl acetate (250 ml) and water (150 ml). The organic phase was dried and evaporated. The crude residue was purified by silica gel flash chromatography, the mobile phase being a mixture of cyclohexane and ethylacetate (in a ratio gradually ranging from 5:1 to 4:1), yielding the pure title compound (558 mg, 96%).

$^1$H-NMR (300 MHz, DMSO-$d_6$): δ=4.35 (s, 3H, OCH$_3$), 8.37 (d, J=2.01 Hz, 1H, arom H), 8.60 (d, J=1.98 Hz, 1H, arom H) ppm.

Examples 23-27

Synthesis of 3-morpholino-6-aryl-isothiazolo[4,3-b]pyridines

General Procedure

To a solution of 3-morpholino-6-bromo-isothiazolo[4,3-b]pyridine (0.37 mmol) in DME (5 ml) and water (1 ml) was added an appropriate boronic acid (2 eq), sodium carbonate (2 eq, 78 mg) and Pd(dppf)Cl$_2$ (0.1 eq, 30 mg). The reaction was heated overnight at 75° C. The reaction mixture was diluted with ethyl acetate (50 ml) and brine (30 ml). The aqueous phase was extracted with ethyl acetate (50 ml). The organic phases were dried and evaporated. The crude residue was purified by silicagel flash chromatography, yielding the pure title compounds.

The following compounds were made according to this procedure:

Example 23

3-morpholino-6-phenyl-isothiazolo[4,3-b]pyridine

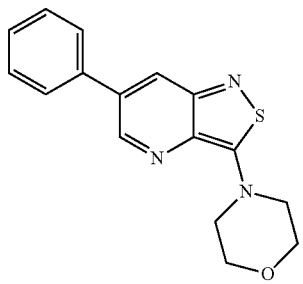 [SMILES: c1ccc(-c2cnc3c(N4CCOCC4)snc3c2)cc1]

This compound was prepared using phenylboronic acid and was purified using a mixture of cyclohexane/ethyl acetate in a ratio of 2:1, affording the title compound in 78% yield.

$^1$H-NMR (300 MHz, DMSO-$d_6$): δ=3.86 (br s, 4H, 2×NCH$_2$), 3.90 (br s, 4H, 2×OCH$_2$), 7.50 (m, 3H, arom H), 7.82 (m, 2H, arom H), 8.01 (d, J=2.1 Hz, 1H, arom H), 8.72 (d, J=2.1 Hz, 1H, arom H) ppm.

Example 24

3-morpholino-6-(4-fluoro-phenyl-isothiazolo[4,3-]pyridine

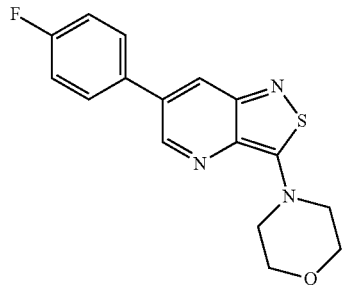 [SMILES: Fc1ccc(-c2cnc3c(N4CCOCC4)snc3c2)cc1]

This compound was prepared using 4-fluorophenylboronic acid and was purified using a mixture of cyclohexane/ ethyl acetate in a ratio of 3:1, affording the title compound in 95% yield.

$^1$H-NMR (300 MHz, DMSO-$d_6$): δ=3.85 (br s, 4H, 2×NCH$_2$), 3.89 (br s, 4H, 2×OCH$_2$), 7.34 (t, J=8.82 Hz, 2H, arom H), 7.87 (m, 2H, arom H), 8.00 (d, J=2.04 Hz, 1H, arom H), 8.69 (d, J=2.04 Hz, 1H, arom H) ppm.

Example 25

3-morpholino-6-(3-pyridyl)-isothiazolo[4,3-b]pyridine

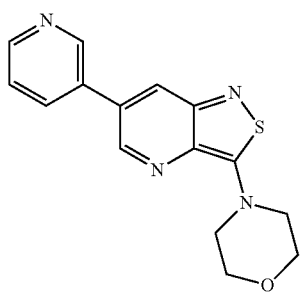 [SMILES: c1cncc(-c2cnc3c(N4CCOCC4)snc3c2)c1]

This compound was prepared using 3-pyridinyl boronic acid and was purified using a mixture of methanol/dichloromethane in a ratio of 1:25, affording the title compound in 80% yield.

$^1$H-NMR (300 MHz, DMSO-$d_6$): δ=3.86 (br s, 4H, 2×NCH$_2$), 3.91 (br s, 4H, 2×OCH$_2$), 7.55 (m, 1H, arom H), 8.15 (d, J=1.95 Hz, 2H, arom H), 8.26 (br d, 1H, arom H), 8.65 (br d, 1H, arom H), 8.76 (d, J=1.92 Hz, 1H, arom H), 9.05 (br s, 1H, arom H) ppm.

Example 26

3-morpholino-6-(3,4-dimethoxyphenyl-isothiazolo[4,3-b]pyridine

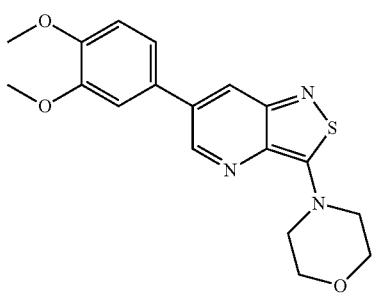 [SMILES: COc1ccc(-c2cnc3c(N4CCOCC4)snc3c2)cc1OC]

This compound was prepared using 3,4-dimethoxyphenylboronic acid and was purified using a mixture of cyclohexane/ethyl acetate in a ratio of 2:1, affording the title compound in 72% yield.

$^1$H-NMR (300 MHz, DMSO-$d_6$): δ=3.82 (s, 3H, OCH$_3$), 3.89 (br s, 11H, 2×NCH$_2$, 2×OCH$_2$ and OCH$_3$), 7.09 (d, J=8.04 Hz, 1H, arom H), 7.39 (m, 2H, arom H), 8.02 (d, J=2.01 Hz, 1H, arom H), 8.75 (d, J=1.95 Hz, 1H, arom H) ppm.

Example 27

3-morpholino-6-(3-thienyl-isothiazolo[4,3-b]pyridine

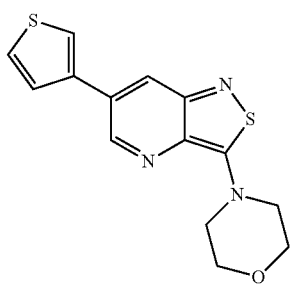 [SMILES: c1cc(-c2cnc3c(N4CCOCC4)snc3c2)cs1]

This compound was prepared using 3-thienylboronic acid and was purified using a mixture of cyclohexane/ethyl acetate in a ratio of 2:1, affording the title compound in 71% yield.

$^1$H-NMR (300 MHz, DMSO-$d_6$): δ=3.86 (br s, 4H, 2×NCH$_2$), 3.88 (br s, 4H, 2×OCH$_2$), 7.73 (m, 1H, arom H), 7.77 (m, 1H, arom H), 8.09 (d, J=2.01 Hz, 1H, arom H), 8.21 (m, 1H, arom H), 8.84 (d, J=2.04 Hz, 1H, arom H) ppm.

Examples 28-32

Synthesis of 3-ethanolamino-6-aryl-isothiazolo[4,3-b]pyridines

General Procedure

To a solution of 3-ethanolamino-6-bromo-isothiazolo[4,3-b]pyridine (0.37 mmol) in dioxane (5 ml) and water (1 ml) was added an appropriate boronic acid (2 eq), sodium carbonate (2 eq, 78 mg) and Pd(dppf)Cl$_2$ (0.1 eq, 30 mg). The reaction was overnight at 75° C. The reaction mixture was diluted with ethyl acetate (50 ml) and brine (30 ml). The aqueous phase was extracted with ethyl acetate (50 ml). The organic phases were dried and evaporated. The crude residue was purified by silicagel flash chromatography yielding the pure title compounds.

The following compounds were made according to this procedure:

Example 28

3-ethanolamino-6-(3-pyridyl-isothiazolo[4,3-b]pyridine

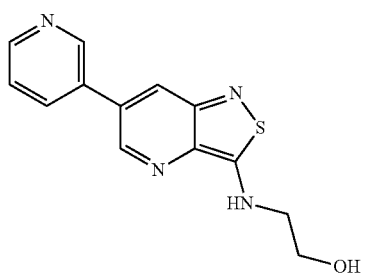 [SMILES: OCCNc1snc2cc(-c3cccnc3)cnc12]

This compound was prepared using 3-pyridyl boronic acid and was purified using a mixture of dichloromethane and methanol (in a ratio gradually ranging from 20:1 to 10:1), affording the title compound in 90% yield.

$^1$H-NMR (300 MHz, DMSO-$d_6$): δ=3.42 (q, J=5.67 Hz, 2H, NCH$_2$), 3.71 (t, J=5.64 Hz, 2H, OCH$_2$), 4.95 (br s, 1H), 7.54 (m, 1H, arom H), 8.05 (br s, 1H, arom H), 8.25 (br d, J=7.95 Hz, 1H, arom H), 8.52 (br t, 1H), 8.61 (m, 2H, arom H), 9.04 (d, J=2.13 Hz 1H, arom H) ppm.

Example 29

3-ethanolamino-6-(3,4-dimethoxyphenyl-isothiazolo[4,3-b]pyridine

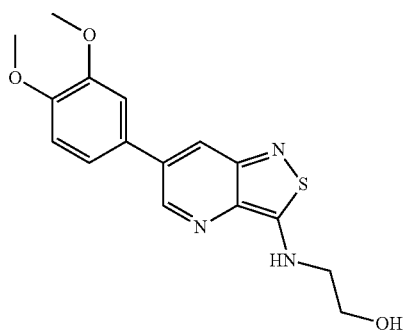 [SMILES: COc1ccc(-c2cnc3c(NCCO)snc3c2)cc1OC]

This compound was prepared using 3,4-dimethoxyphenylboronic acid and was purified using a mixture of dichloromethane and methanol (in a ratio 30:1), affording the title compound in 95% yield.

$^1$H-NMR (300 MHz, DMSO-$d_6$): δ=3.42 (q, J=5.62 Hz, 2H, NCH$_2$), 3.70 (q, J=5.42 Hz, 2H, OCH$_2$), 3.81 (s, 3H, OCH$_3$), 3.88 (s, 3H, OCH$_3$), 4.93 (t, J=5.67 Hz, 1H), 7.07 (d,

J=8.34 Hz, 1H, arom H), 7.36 (m, 2H, arom H), 7.92 (s, 1H, arom H), 8.40 (t, J=5.55 Hz, 1 arom H), 8.64 (br s, 1H, arom H) ppm.

Example 30

3-ethanolamino-6-(3-thienyl)-isothiazolo[4,3-b]pyridine

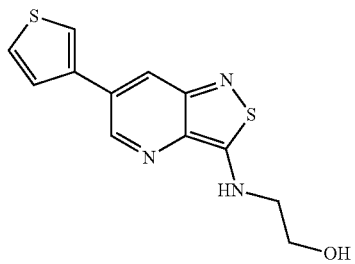 [SMILES: OCCNc1snc2cc(-c3ccsc3)cnc12]

This compound was prepared using 3-thienylboronic acid and was purified using a mixture of dichloromethane and methanol (in a ratio 30:1), affording the title compound in 90% yield.

$^1$H-NMR (300 MHz, DMSO-d$_6$): δ=3.40 (q, J=5.58 Hz, 2H, NCH$_2$), 3.70 (q, J=5.64 Hz, 2H, OCH$_2$), 4.93 (t, J=5.49 Hz, 1H), 7.74 (m, 2H, arom H), 8.01 (br s, 1H, arom H), 8.19 (br s, 1 arom H), 8.42 (br t, 1H), 8.75 (br s, 1H, arom H) ppm.

Example 31

3-ethanolamino-6-phenyl-isothiazolo[4,3-b]pyridine

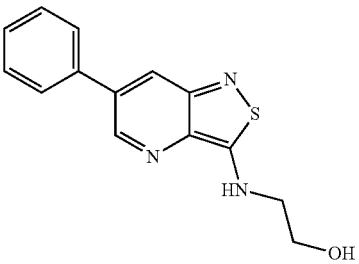 [SMILES: OCCNc1snc2cc(-c3ccccc3)cnc12]

This compound was prepared using phenylboronic acid and was purified using a mixture of dichloromethane and methanol (in a ratio 20:1), affording the title compound in 99% yield.

$^1$H-NMR (300 MHz, DMSO-d$_6$): δ=3.41 (q, J=5.80 Hz, 2H, NCH$_2$), 3.71 (q, J=5.61 Hz, 2H, OCH$_2$), 4.95 (t, J=5.52 Hz, 1H), 7.49 (m, 5H, arom H), 7.80 (br d, J=7.23 Hz, 1H, arom H), 7.91 (s, 1H, arom H), 8.50 (br t, 1H), 8.63 (d, J=1.59 Hz, 1H, arom H) ppm.

Example 32

3-ethanolamino-6-(3-(4-fluorophenyl))-isothiazolo[4,3-b]pyridine

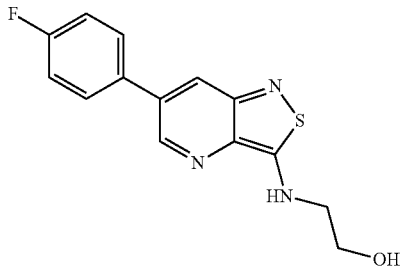 [SMILES: OCCNc1snc2cc(-c3ccc(F)cc3)cnc12]

This compound was prepared using 4-fluorophenylboronic acid and was purified using a mixture of dichloromethane and methanol (in a ratio 20:1), affording the title compound in 81% yield.

$^1$H-NMR (300 MHz, DMSO-d$_6$): δ=3.30 (2H, NCH$_2$, hidden under H$_2$O peak), 3.71 (q, J=5.61 Hz, 2H, OCH$_2$), 4.96 (t, J=5.45 Hz, 1H), 7.35 (t, J=8.64 Hz, 1H, arom H), 7.88 (m, 3H, arom H), 8.47 (br t, 1H), 8.62 (br s, 1H, arom H) ppm.

Examples 33-37

Synthesis of
3-methoxy-6-aryl-isothiazolo[4,3-b]pyridines

General Procedure

To a solution of 3-methoxy-6-bromo-isothiazolo[4,3-b]pyridine (100 mg, 0.41 mmol) in dioxane (5 ml) and water (1 ml) was added an appropriate boronic acid (2 eq), sodium carbonate (2 eq, 87 mg) and Pd(dppf)Cl$_2$ (0.1 eq, 33 mg). The reaction mixture was heated at 95° C. overnight. The reaction mixture was diluted with ethyl acetate (50 ml) and brine (30 ml). The aqueous phase was extracted with ethyl acetate (50 ml). The organic phases were dried and evaporated. The crude residue was purified by silicagel flash chromatography yielding the pure title compounds.

The following compounds were made according to this procedure:

Example 33

3-methoxy-6-phenyl-isothiazolo[4,3-b]pyridine

This compound was prepared using phenylboronic acid and the crude residue was purified using a mixture of cyclohexane and ethylacetate (in a ratio of 2:1), affording the title compound in 87% yield.

$^1$H-NMR (300 MHz, CDCl$_3$): δ=4.37 (s, 3H, OCH$_3$), 7.50 (m, 3H, arom H), 7.68 (m, 2H, arom H), 8.00 (d, J=2.01 Hz, 1H, arom H), 8.86 (d, J=1.98 Hz, 1H, arom H) ppm.

Example 34

3-methoxy-6-(4-fluoro-phenyl)-isothiazolo[4,3-b]pyridine

This compound was prepared using 4-fluoro-phenylboronic acid and the crude residue was purified using a mixture of cyclohexane and ethylacetate (in a ratio of 2:1), affording the title compound in 76% yield.

$^1$H-NMR (300 MHz, DMSO-$d_6$): δ=4.36 (s, 3H, OCH$_3$), 7.37 (t, J=8.79, 3H, arom H), 7.93 (m, 2H, arom H), 8.18 (d, J=1.98 Hz, 1H, arom H), 8.93 (d, J=1.92 Hz, 1H, arom H) ppm.

Example 35

3-methoxy-6-(3-pyridyl-isothiazolo[4,3-b]pyridine

This compound was prepared using 3-pyridylboronic acid and the crude residue was purified using a mixture of methanol and dichloromethane (in a ratio of 1:30), affording the title compound in 55% yield.

$^1$H-NMR (300 MHz, DMSO-$d_6$): δ=4.40 (s, 3H, OCH$_3$), 7.57 (m, 1H, arom H), 8.31 (m, 2H, arom H), 8.67 (d, J=4.23 Hz, 1H, arom H), 8.99 (d, J=1.71 Hz, 1H, arom H), 9.09 (d, J=1.89 Hz, 1H, arom H) ppm.

Example 36

3-methoxy-6-(3,4-dimethoxyphenyl-isothiazolo[4,3-b]pyridine

This compound was prepared using 3,4-dimethoxyphenylboronic acid and the crude residue was purified using a mixture of cyclohexane and ethylacetate (in a ratio of 1:1), affording the title compound in 74% yield.

$^1$H-NMR (300 MHz, DMSO-$d_6$): δ=3.82 (s, 3H, OCH$_3$), 3.89 (s, 3H, OCH$_3$), 4.35 (s, 3H, OCH$_3$), 7.09 (d, J=9 Hz, 1H, arom H), 7.42 (m, 2H, arom H), 8.16 (d, J=1.92 Hz, 1H, arom H), 8.97 (d, J=1.92 Hz, 1H, arom H) ppm.

Example 37

3-methoxy-6-(3-thienyl-isothiazolo[4,3-b]pyridine

This compound was prepared using 3-thienylboronic acid and the crude residue was purified using a mixture of cyclohexane and ethylacetate (in a ratio of 2:1), affording the title compound in 75% yield.

$^1$H-NMR (300 MHz, DMSO-$d_6$): δ=4.35 (s, 3H, OCH$_3$), 7.74 (m, 1H, arom H), 7.82 (m, 1H, arom H), 8.25 (d, J=1.98 Hz, 1H, arom H), 8.29 (m, 1H, arom H), 9.06 (d, J=1.95 Hz, 1H, arom H) ppm.

Examples 38-42

Synthesis of 3-(N-Me-piperazinyl)-6-aryl-isothiazolo[4,3-b]pyridines

General Procedure

To a solution of 3-(N-methylpiperazino)-6-bromo-isothiazolo[4,3-b]pyridine (100 mg, 0.32 mmol) in dioxane (6 ml) and water (2.5 ml) was added an appropriate boronic acid (2 eq), sodium carbonate (2 eq, 68 mg) and Pd(dppf)Cl$_2$ (0.1 eq, 26 mg). The reaction mixture was heated at 95° C. overnight. The reaction mixture was diluted with ethyl acetate (50 ml) and brine (30 ml). The aqueous phase was extracted with ethyl acetate (50 ml). The organic phases were dried and evaporated. The crude residue was purified by silicagel flash chromatography yielding the pure title compounds.

The following compounds were made according to this procedure:

Example 38

3-(N-Me-piperazinyl-6-phenyl-isothiazolo[4,3-b]pyridine

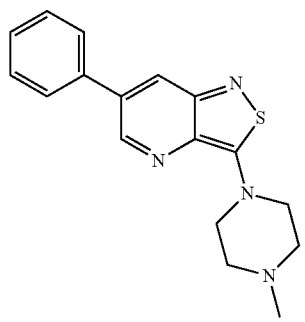 [SMILES: CN1CCN(c2snc3cc(-c4ccccc4)cnc23)CC1]

This compound was prepared using phenylboronic acid and the crude residue was purified using a mixture of methanol and dichloromethane (in a ratio of 3:100), affording the title compound in 91% yield.

$^1$H-NMR (300 MHz, CDCl$_3$): δ=2.39 (s, 3H, NCH$_3$), 2.67 (t, J=5.01 Hz, 4H, 2×NCH$_2$), 4.00 (t, J=4.99 Hz, 4H, 2×NCH$_2$), 7.47 (m, 3H, arom H), 7.65 (m, 2H, arom H), 7.89 (d, J=1.83 Hz, 1H, arom H), 8.63 (d, J=1.83 Hz, 1H, arom H) ppm.

Example 39

3-(N-Me-piperazinyl)-6-(3-pyridyl)-isothiazolo[4,3-b]pyridine

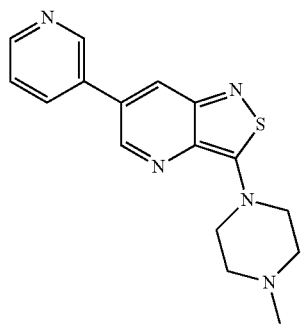 [SMILES: CN1CCN(c2snc3cc(-c4cccnc4)cnc23)CC1]

This compound was prepared using 3-pyridylboronic acid and the crude residue was purified using a mixture of methanol and dichloromethane (in a ratio of 1:20), affording the title compound in 83% yield.

$^1$H-NMR (300 MHz, DMSO-$d_6$): δ=2.26 (s, 3H, NCH$_3$), 2.55 (t, J=4.85 Hz, 4H, 2×NCH$_2$), 3.92 (t, J=4.80 Hz, 4H, 2×NCH$_2$), 7.54 (m, 1H, arom H), 8.12 (d, J=1.98 Hz, 1H, arom H), 8.24 (d, J=7.86 Hz, 1H, arom H), 8.65 (d, J=4.74 Hz, 1H, arom H), 8.75 (d, J=1.92 Hz, 1H, arom H), 9.04 (d, J=1.95 Hz, 1H, arom H) ppm.

Example 40

3-(N-Me-piperazinyl)-6-(3,4-dimethoxyphenyl)-isothiazolo[4,3-b]pyridine

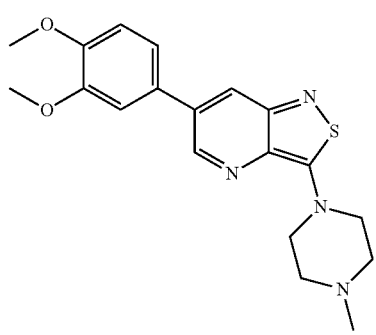 [SMILES: COc1ccc(-c2cnc3c(N4CCN(C)CC4)snc3c2)cc1OC]

This compound was prepared using 3,4-dimethoxyphenyl boronic acid and the crude residue was purified using a mixture of methanol and dichloromethane (in a ratio of 1:30), affording the title compound in 66% yield.

$^1$H-NMR (300 MHz, DMSO-d$_6$): δ=2.27 (s, 3H, NCH$_3$), 2.56 (t, J=4.91 Hz, 4H, 2×NCH$_2$), 3.82 (s, 3H, OCH$_3$), 3.88 (s, 3H, OCH$_3$), 3.92 (t, J=4.88 Hz, 4H, 2×NCH$_2$), 7.09 (d, J=8.43 Hz, 1H, arom H), 7.38 (m, 2H, arom H), 7.99 (d, J=1.98 Hz, 1H, arom H), 8.75 (d, J=2.01 Hz, 1H, arom H) ppm.

Example 41

3-(N-Me-piperazinyl)-6-(3-thienyl)-isothiazolo[4,3-b]pyridine

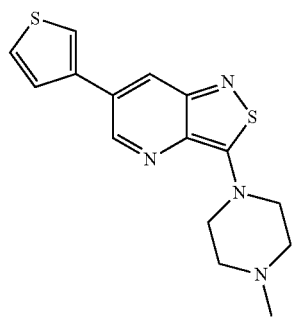 [SMILES: CN1CCN(c2snc3cc(-c4ccsc4)cnc23)CC1]

This compound was prepared using 3-thienylboronic acid and the crude residue was purified using a mixture of methanol and dichloromethane (in a ratio of 3:100), affording the title compound in 84% yield.

$^1$H-NMR (300 MHz, DMSO-d$_6$): δ=2.26 (s, 3H, NCH$_3$), 2.55 (t, J=4.91 Hz, 4H, 2×NCH$_2$), 3.91 (t, J=4.88 Hz, 4H, 2×NCH$_2$), 7.72 (m, 2H, arom H), 8.07 (br s, 1H, arom H), 8.07 (br s, 1H, arom H), 8.19 (br s, 1H, arom H), 8.83 (d, J=1.98 Hz, 1H, arom H) ppm.

Example 42

3-(N-Me-piperazinyl)-6-(4-fluorophenyl)-isothiazolo[4,3-b]pyridine

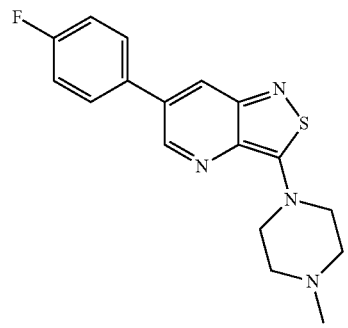 [SMILES: CN1CCN(c2snc3cc(-c4ccc(F)cc4)cnc23)CC1]

This compound was prepared using 4-fluorophenylboronic acid and the crude residue was purified using a mixture of methanol and dichloromethane (in a ratio of 3:100), affording the title compound in 96% yield.

$^1$H-NMR (300 MHz, CDCl$_3$): δ=2.40 (s, 3H, NCH$_3$), 2.68 (br s, 4H, 2×NCH$_2$), 4.00 (br s, 4H, 2×NCH$_2$), 7.19 (t, J=8.61 Hz, 1H, arom H), 7.59 (m, 2H, arom H), 7.84 (d, J=2.01 Hz, 1H, arom H), 8.57 (d, J=2.01 Hz, arom H) ppm.

Examples 43-54

Synthesis of 3-morpholino-6-aryl-isothiazolo[4,3-b]pyridines

General Procedure

To a solution of 3-morpholino-6-bromo-isothiazolo[4,3-b]pyridine in DME (2 ml) was added an appropriate boronic acid (2 eq or 1.5 eq) and potassium carbonate (2 eq, 1M solution in H$_2$O). Mixture was degassed and Pd(PPh$_3$)$_4$ (10 mol %) was added. The reaction was heated at 80° C. After the completion of reaction, solvents were evaporated. The crude residue was purified by silicagel flash chromatography, yielding the pure title compounds.

The following compounds were made according to this procedure:

Example 43

4-(6-(Thiophen-2-yl)isothiazolo[4,3-b]pyridin-3-yl)morpholine

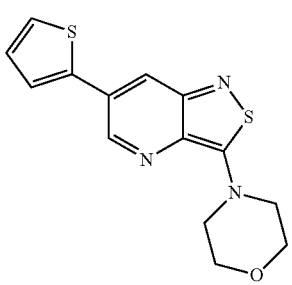 [SMILES: c1csc(-c2cnc3c(N4CCOCC4)snc3c2)c1]

This compound was prepared from 3-morpholino-6-bromo-isothiazolo[4,3-b]pyridine (90 mg, 0.3 mmol) using thiophene-2-boronic acid (0.6 mmol, 76 mg), 1M K$_2$CO$_3$ (0.6 ml) and Pd(PPh$_3$)$_4$ (0.03 mmol, 34 mg). Product was purified using a mixture of cyclohexane/ethyl acetate in a ratio of 1:1, affording the title compound in 78% yield (71 mg, 0.234 mmol).

1H-NMR (300 MHz, CDCl$_3$): δ=3.96 (m, 8H, 4×CH$_2$), 7.16 (dd, J=3.66 Hz, J=5.10 Hz, 1H, arom H), 7.42 (dd, J=1.08 Hz, J=5.10 Hz, 1H, arom H), 7.49 (dd, J=3.66 Hz, J=1.08 Hz, 1H, arom H), 7.93 (d, J=2.07 Hz, 1H, arom H), 8.69 (d, J=2.10 Hz, 1H, arom H) ppm.

Example 44

4-(6-(2,5-Dimethoxyphenyl)isothiazolo[4,3-b]pyridin-3-yl)morpholine

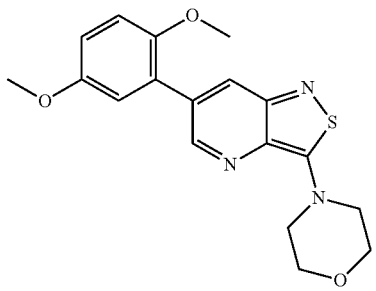 [SMILES: COc1ccc(OC)c(-c2cnc3c(N4CCOCC4)snc3c2)c1]

This compound was prepared from 3-morpholino-6-bromo-isothiazolo[4,3-b]pyridine (90 mg, 0.3 mmol) using 2,5-dimethoxyphenylboronic acid (0.6 mmol, 109 mg), 1M K$_2$CO$_3$ (0.6 ml) and Pd(PPh$_3$)$_4$ (0.03 mmol, 34 mg). Product was purified using a mixture of cyclohexane/ethyl acetate in a ratio of 2:1, affording the title compound in 69% yield (74 mg, 0.207 mmol).

1H-NMR (300 MHz, CDCl$_3$): δ=3.80 (s, 3H, OCH$_3$), 3.84 (s, 3H, OCH$_3$), 3.97 (m, 8H, 4×CH$_2$), 6.95-6.97 (m, 3H, arom H), 7.89 (d, J=1.95 Hz, 1H, arom H), 8.58 (d, J=1.92 Hz, 1H, arom H) ppm.

Example 45

4-(6-(2,4-Dimethoxyphenyl)isothiazolo[4,3-b]pyridin-3-yl)morpholine

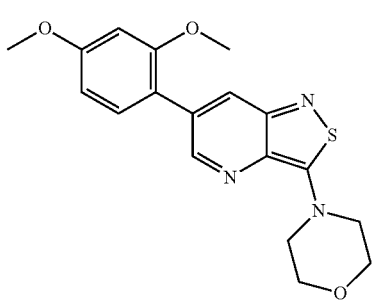 [SMILES: COc1ccc(-c2cnc3c(N4CCOCC4)snc3c2)c(OC)c1]

This compound was prepared from 3-morpholino-6-bromo-isothiazolo[4,3-b]pyridine (90 mg, 0.3 mmol) using 2,4-dimethoxyphenylboronic acid (0.6 mmol, 109 mg), 1M K$_2$CO$_3$ (0.6 ml) and Pd(PPh$_3$)$_4$ (0.03 mmol, 34 mg). Product was purified using a mixture of cyclohexane/ethyl acetate in a ratio of 2:1, affording the title compound in 73% yield (79 mg, 0.221 mmol).

1H-NMR (300 MHz, CDCl$_3$): δ=3.84 (s, 3H, OCH$_3$), 3.88 (s, 3H, OCH$_3$), 3.96 (m, 8H, 4×CH$_2$), 6.60-6.64 (m, 2H, arom H), 7.33 (d, J=8.19 Hz, 1H, arom H), 7.84 (d, J=1.95 Hz, 1H, arom H), 8.57 (d, J=1.92 Hz, 1H, arom H) ppm.

Example 46

Methyl 2-methoxy-4-(3-morpholinoisothiazolo[4,3-]pyridin-6-yl)benzoate

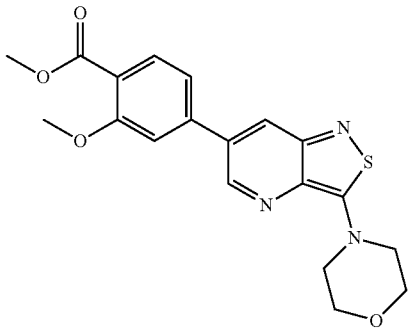 [SMILES: COC(=O)c1ccc(-c2cnc3c(N4CCOCC4)snc3c2)cc1OC]

This compound was prepared from 3-morpholino-6-bromo-isothiazolo[4,3-b]pyridine (60 mg, 0.2 mmol) using 4-methoxycarbonyl-3-methoxyphenylboronic acid (0.4 mmol, 84 mg), 1M K$_2$CO$_3$ (0.4 ml) and Pd(PPh$_3$)$_4$ (0.02 mmol, 23 mg). Product was purified using a mixture of cyclohexane/ethyl acetate in a ratio of 2:1, affording the title compound in 66% yield (51 mg, 0.132 mmol).

1H-NMR (300 MHz, CDCl$_3$): δ=3.96 (s, 3H, OCH$_3$), 3.98 (m, 8H, 4×CH$_2$), 4.00 (s, 3H, OCH$_3$(ester)), 7.23 (d, J=1.38 Hz, 1H, arom H), 7.27 (m, 1H, arom H), 7.93 (s, 1H, arom H), 7.96 (d, J=1.83 Hz, 1H, arom H), 8.64 (d, J=2.07 Hz, 1H, arom H) ppm.

Example 47

2-Methoxy-4-(3-morpholinoisothiazolo[4,3-b]pyridin-6-yl)phenyl acetate

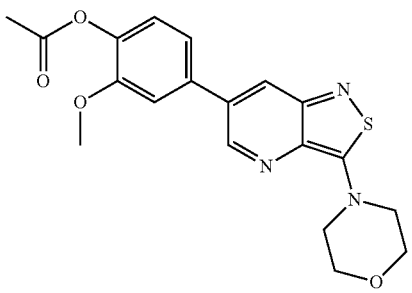 [SMILES: COc1cc(-c2cnc3c(N4CCOCC4)snc3c2)ccc1OC(C)=O]

This compound was prepared from 3-morpholino-6-bromo-isothiazolo[4,3-b]pyridine (60 mg, 0.2 mmol) using 4-acetoxy-3-methoxyphenylboronic acid pinacol ester (0.4 mmol, 116 mg), 1M K$_2$CO$_3$ (0.4 ml) and Pd(PPh$_3$)$_4$ (0.02 mmol, 23 mg). Product was purified using a mixture of cyclohexane/ethyl acetate in a ratio of 2:1, affording the title compound in 58% yield (45 mg, 0.116 mmol).

1H-NMR (300 MHz, CDCl$_3$): δ=2.37 (s, 3H, CH$_3$ (acetyl)), 3.93 (s, 3H, OCH$_3$), 3.98 (m, 8H, 4×CH$_2$), 7.16-

7.28 (m, 3H, arom H), 7.91 (d, J=1.98 Hz, 1H, arom H), 8.53 (d, J=2.01 Hz, 1H, arom H) ppm.

Example 48

4-(6-(3,5-Dimethoxyphenyl)isothiazolo[4,3-b]pyridin-3-yl)morpholine

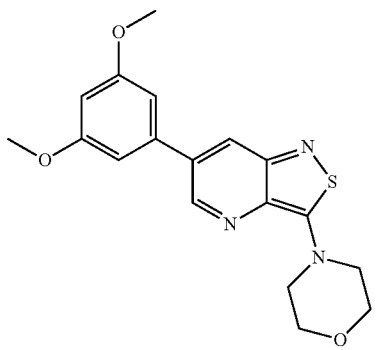 [SMILES: COc1cc(OC)cc(-c2cnc3c(N4CCOCC4)snc3c2)c1]

This compound was prepared from 3-morpholino-6-bromo-isothiazolo[4,3-b]pyridine (60 mg, 0.2 mmol) using 3,5-dimethoxyphenylboronic acid (0.4 mmol, 72 mg), 1M $K_2CO_3$ (0.4 ml) and $Pd(PPh_3)_4$ (0.02 mmol, 23 mg). Product was purified using a mixture of cyclohexane/ethyl acetate in a ratio of 2:1, affording the title compound in 70% yield (50 mg, 0.140 mmol).

1H-NMR (300 MHz, $CDCl_3$): δ=3.88 (s, 6H, 2×$OCH_3$), 3.98 (m, 8H, 4×$CH_2$), 6.55 (m, 1H, arom H), 6.80 (d, J=2.19 Hz, 2H, arom H), 7.92 (d, J=1.98 Hz, 1H, arom H), 8.63 (d, J=2.01 Hz, 1H, arom H) ppm.

Example 49

4-(6-(3,4,5-Trimethoxyphenyl)isothiazolo[4,3-b]pyridin-3-yl)morpholine

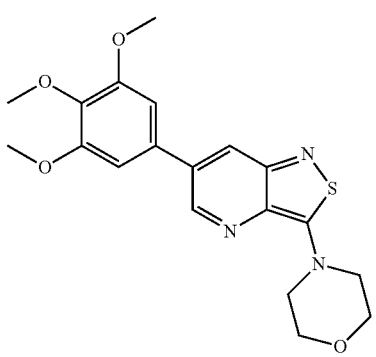 [SMILES: COc1cc(-c2cnc3c(N4CCOCC4)snc3c2)cc(OC)c1OC]

This compound was prepared from 3-morpholino-6-bromo-isothiazolo[4,3-b]pyridine (76 mg, 0.25 mmol) using 3,4,5-trimethoxyphenylboronic acid (0.5 mmol, 107 mg), 1M $K_2CO_3$ (0.5 ml) and $Pd(PPh_3)_4$ (0.025 mmol, 29 mg). Product was purified using a mixture of cyclohexane/ethyl acetate in a ratio of 2:1, affording the title compound in 56% yield (54 mg, 0.141 mmol).

1H-NMR (300 MHz, $CDCl_3$): δ=3.91 (s, 3H, $OCH_3$), 3.94 (s, 6H, 2×$OCH_3$), 3.96 (m, 8H, 4×$CH_2$), 6.85 (s, 2H, arom H), 7.88 (d, J=1.86 Hz, 1H, arom H), 8.62 (d, J=1.89 Hz, 1H, arom H) ppm.

Example 50

2-Methoxy-4-(3-morpholinoisothiazolo[4,3-]pyridin-6-yl)aniline

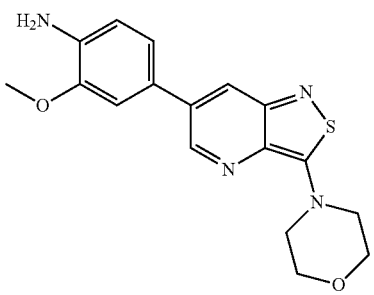

This compound was prepared from 3-morpholino-6-bromo-isothiazolo[4,3-b]pyridine (60 mg, 0.2 mmol) using 4-amino-3-methoxyphenylboronic acid pinacol ester (0.4 mmol, 99 mg), 1M $K_2CO_3$ (0.4 ml) and $Pd(PPh_3)_4$ (0.02 mmol, 23 mg). Product was purified using a mixture of cyclohexane/ethyl acetate in a ratio of 2:1, affording the title compound in 58% yield (40 mg, 0.116 mmol).

1H-NMR (300 MHz, $CDCl_3$): δ=3.95 (s, 3H, $OCH_3$), 3.97 (m, 8H, 4×$CH_2$), 6.82 (d, J=7.98 Hz, 1H, arom H), 7.10 (m, 2H, arom H), 7.85 (d, J=2.04 Hz, 1H, arom H), 8.66 (d, J=2.07 Hz, 1H, arom H) ppm.

Example 51

4-(6-(Benzo[d][1,3]dioxol-5-yl)isothiazolo[4,3-b]pyridin-3-yl)morpholine

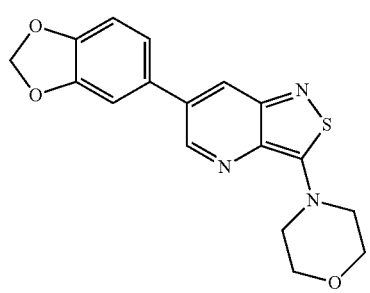 [SMILES: c1cc2c(cc1-c1cnc3c(N4CCOCC4)snc3c1)OCO2]

This compound was prepared from 3-morpholino-6-bromo-isothiazolo[4,3-b]pyridine (60 mg, 0.2 mmol) using 3,4-methylenedioxyphenylboronic acid (0.4 mmol, 66 mg), 1M $K_2CO_3$ (0.4 ml) and $Pd(PPh_3)_4$ (0.02 mmol, 23 mg). Product was purified using a mixture of cyclohexane/ethyl acetate in a ratio of 2:1, affording the title compound in 64% yield (43 mg, 0.128 mmol).

1H-NMR (300 MHz, $CDCl_3$): δ=3.96 (m, 8H, 4×$CH_2$), 6.05 (s, 2H, $CH_2$), 6.94 (d, J=7.86 Hz, 1H, arom H), 7.15 (m, 2H, arom H), 7.83 (d, J=2.01 Hz, 1H, arom H), 8.58 (d, J=2.04 Hz, 1H, arom H) ppm.

Example 52

4-(6-(Furan-3-yl)isothiazolo[4,3-b]pyridin-3-yl)morpholine

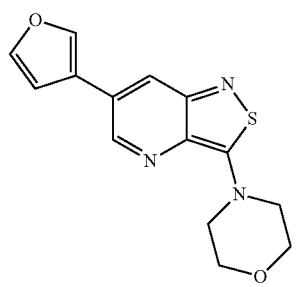 [SMILES: c1cc(-c2cnc3c(N4CCOCC4)snc3c2)co1]

This compound was prepared from 3-morpholino-6-bromo-isothiazolo[4,3-b]pyridine (40 mg, 0.133 mmol) using furan-3-boronic acid (0.2 mmol, 23 mg), 1M $K_2CO_3$ (0.26 ml) and $Pd(PPh_3)_4$ (0.013 mmol, 36 mg). Product was purified using a mixture of cyclohexane/ethyl acetate in a ratio of 2:1, affording the title compound in 51% yield (19 mg, 0.067 mmol).

1H-NMR (300 MHz, $CDCl_3$): δ=3.96 (m, 8H, 4×$CH_2$), 6.79 (s, 1H, arom H), 7.56 (m, 1H, arom H), 7.81 (d, J=2.01 Hz, 1H, arom H), 7.90 (s, 1H, arom H), 8.56 (d, J=2.01 Hz, 1H, arom H) ppm.

Example 53

Methyl 4-(3-morpholinoisothiazolo[4,3-b]pyridin-6-yl)benzoate

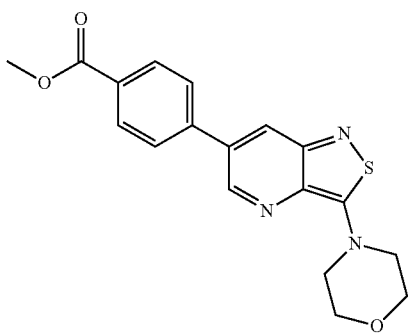 [SMILES: COC(=O)c1ccc(-c2cnc3c(N4CCOCC4)snc3c2)cc1]

This compound was prepared from 3-morpholino-6-bromo-isothiazolo[4,3-b]pyridine (40 mg, 0.133 mmol) using 3-ethoxycarbonylphenylboronic acid (0.2 mmol, 36 mg), 1M $K_2CO_3$ (0.26 ml) and $Pd(PPh_3)_4$ (0.013 mmol, 36 mg). Product was purified using a mixture of cyclohexane/ethyl acetate in a ratio of 3:1, affording the title compound in 67% yield (32 mg, 0.090 mmol).

1H-NMR (300 MHz, $CDCl_3$): δ=3.99 (m, 11H, 4×$CH_2$, $OCH_3$), 7.74 (d, J=8.1 Hz, 2H, arom H), 7.98 (d, J=1.47 Hz, 1H, arom H), 8.19 (d, J=8.1 Hz, 2H, arom H), 8.65 (d, J=1.46 Hz, 1H, arom H) ppm.

Example 54

N-Methyl-4-(3-morpholinoisothiazolo[4,3-b]pyridin-6-yl)benzamide

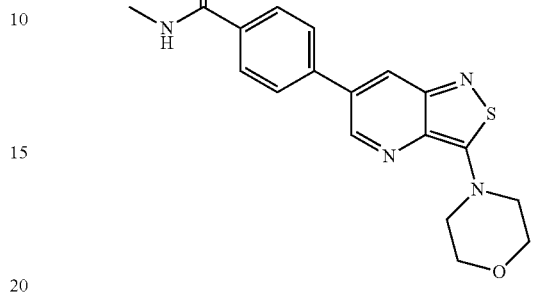

This compound was prepared from 3-morpholino-6-bromo-isothiazolo[4,3-b]pyridine (40 mg, 0.133 mmol) using 4-(N-methylaminocarbonyl)phenylboronic acid (0.2 mmol, 35 mg), 1M $K_2CO_3$ (0.26 ml) and $Pd(PPh_3)_4$ (0.013 mmol, 36 mg). Product was purified using a mixture of cyclohexane/ethyl acetate in a ratio of 2:3, affording the title compound in 31% yield (14 mg, 0.041 mmol).

1H-NMR (300 MHz, $CDCl_3$): δ=3.09 (d, J=4.71 Hz, 3H, $NCH_3$), 3.99 (m, 8H, 4×$CH_2$), 7.73 (d, J=8.25 Hz, 1H, arom H), 7.90 (d, J=8.22 Hz, 2H, arom H), 8.00 (d, J=1.89 Hz, 1H, arom H), 8.64 (d, J=1.86 Hz, 1H, arom H) ppm.

Examples 55-56

Synthesis of 3-substituted-6-bromo-isothiazolo[4,3-b]pyridines

General Procedure

These compounds were prepared according to the general procedure described for examples 11-13.

The following compounds were prepared according to this procedure:

Example 55

6-bromo-3-(piperidin-1-yl)isothiazolo[4,3-b]pyridine

This compound was made using piperidine as nucleophile and the crude residue was purified using a mixture of cyclohexane and ethylacetate (in a ratio of 4:1) as mobile phase, affording the title compound in 85% yield.

¹H-NMR (300 MHz, $CDCl_3$) δ=1.75 (m, 6H), 3.9 (t, J=5.22, 4H, 2×$NCH_2$), 7.89 (d, J=2.1 Hz, 1H, arom H), 8.25 (d, J=2.07 Hz, 1H, arom H) ppm.

Example 56

6-bromo-3-thiomorpholinoisothiazolo[4,3-b]pyridine

This compound was made using thiomorpholine as nucleophile and the crude residue was purified using a mixture of cyclohexane and ethylacetate (in a ratio of 4:1) as mobile phase, affording the title compound in 86% yield.

¹H-NMR (300 MHz, $CDCl_3$) δ=2.83 (m, 4H, 2×$SCH_2$), 4.82 (m, 4H, 2×$NCH_2$), 7.91 (d, J=2.07 Hz, 1H, arom H), 8.27 (d, J=2.04 Hz, 1H, arom H) ppm.

Examples 57-58

Synthesis of 3-substituted-6-aryl-isothiazolo[4,3-b]pyridines

General Procedure

These compounds were prepared according to the methods described for the synthesis of examples 23-27.

The following compounds were made according to this procedure:

Example 57

6-(3,4-dimethoxyphenyl-3-(piperidin-1-yl)isothiazolo[4,3-b]pyridine

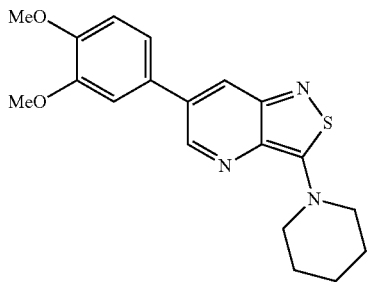 [SMILES: COc1ccc(-c2cnc3c(N4CCCCC4)snc3c2)cc1OC]

This compound was prepared using 3,4-dimethoxyphenylboronic acid and was purified using a mixture of cyclohexane and ethylacetate (in a ratio of 1:1), affording the title compound in 45% yield.

$^1$H-NMR (300 MHz, CDCl$_3$) δ=1.74 (m, 6H), 3.88 (br s, 4H, 2×NCH$_2$) 3.91 (d, J=6.78, 6H, 2×OCH$_3$), 6.95 (d, J=8.31 Hz, 1H, arom H), 7.13 (s, 1H, arom H), 7.19 (dd, J=1.93; 8.26 Hz, 1H arom H), 7.80 (d, J=1.98 Hz, 1H, arom H), 8.57 (d, J=1.98 Hz, 1H, arom H) ppm. $^{13}$C-NMR (300 MHz, CDCl$_3$), 24.0 (CH$_2$), 25.3 (CH$_2$), 51.8 (CH$_2$), 56.0 (CH$_3$), 56.0 (CH$_3$), 110.4 (CH), 111.7 (CH), 119.8 (CH), 124.6 (CH), 130.5 (C$_q$), 133.7 (C$_q$), 135.3 (C$_q$), 143.5 (CH), 149.5 (C$_q$), 156.3 (C$_q$), 173.5 (C$_q$) ppm.

Example 58

6-(3,4-dimethoxyphenyl)-3-thiomorpholinoisothiazolo[4,3-b]pyridine

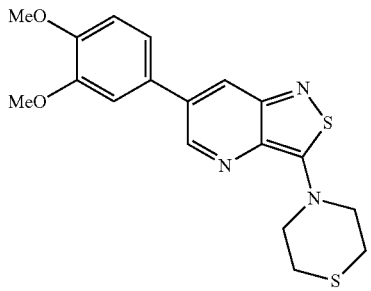 [SMILES: COc1ccc(-c2cnc3c(N4CCSCC4)snc3c2)cc1OC]

This compound was prepared using 3,4-dimethoxyphenylboronic acid and was purified using a mixture of cyclohexane and ethylacetate (in a ratio of 1:1), affording the title compound in 52% yield.

$^1$H-NMR (300 MHz, CDCl$_3$) δ=2.85 (m, 4H, 2×SCH$_2$), 3.92 (d, J=6.15, 6H, 2×OCH$_3$), 4.29 (m, 4H, 2×NCH$_2$), 6.96 (d, J=8.25 Hz, 1H, arom H), 7.13 (s, 1H, arom H), 7.20 (dd, J=1.45; 8.26 Hz, 1H, arom H), 7.81 (d, J=1.95 Hz, 1H, arom H), 8.58 (d, J=1.41 Hz, 1H, arom H) ppm. $^{13}$C-NMR (300 MHz, CDCl$_3$), 26.5 (CH$_2$), 53.2 (CH$_2$), 56.0 (CH$_3$), 56.0 (CH$_3$), 110.4 (CH), 111.7 (CH), 119.9 (CH), 124.8 (CH), 130.3 (C$_q$), 133.7 (C$_q$), 135.6 (C$_q$), 144.2 (CH), 149.5 (C$_q$), 149.6 (C$_q$), 156.6 (C$_q$), 172.3 (C$_q$) ppm.

Example 59

Synthesis of 3-bromo-6-(2-bromo-4,5-dimethoxyphenyl)isothiazolo[4,3-b]pyridine

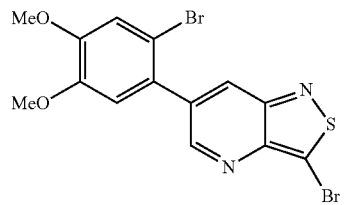 [SMILES: COc1cc(Br)c(-c2cnc3c(Br)snc3c2)cc1OC]

To a solution of 3-amino-6-(3,4-dimethoxyphenyl)-isothiazolo[4,3-b]pyridine (1 g, 3.5 mmol) in HBr (20 ml) at 0° C., was added portionwise sodium nitrite (2 eq, 0.48 g). After 30 minutes, CuBr (2 eq, 1.33 g) was added. The reaction mixture was stirred for two hours, at 0° C. and then heated to 80° C. for the other two hours. The mixture was neutralized with solid potassium carbonate and extracted with ethyl acetate (2×50 ml). The combined organic phases were dried over MgSO$_4$ and evaporated in vacuo. The crude residue was purified by silica gel flash chromatography, the mobile phase being a mixture of cyclohexane and ethylacetate (in a ratio of 9:1), yielding the pure title compound (0.93 g, 62%).

$^1$H-NMR (300 MHz, CDCl$_3$) δ=3.88 (s, 3H, OCH$_3$), 3.93 (s, 3H, OCH$_3$), 6.87 (s, 1H, arom H), 7.16 (s, 1H, arom H), 8.05 (t, J=0.96 Hz, 1H, arom H), 8.92 (t, J=0.95 Hz, 1H, arom H) ppm. $^{13}$C-NMR (300 MHz, CDCl$_3$), 56.3 (CH$_3$), 56.5 (CH$_3$), 113.0 (C$_q$), 113.9 (CH), 116.2 (CH), 129.0 (CH), 129.8 (C$_q$), 135.8 (C$_q$), 137.1 (C$_q$), 145.5 (C$_q$), 149.0 (C$_q$), 150.2 (C$_q$), 154.2 (CH), 154.7 (C$_q$) ppm.

Example 60

Synthesis of 4-(6-(2-bromo-4,5-dimethoxyphenyl)isothiazolo[4,3-b]pyridin-3-yl)morpholine

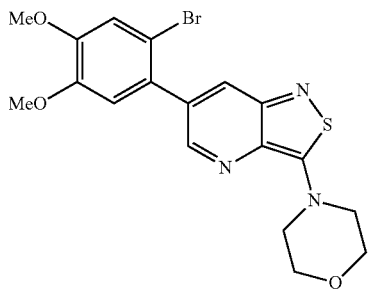 [SMILES: COc1cc(Br)c(-c2cnc3c(N4CCOCC4)snc3c2)cc1OC]

To a solution of 3-bromo-6-(2-bromo-4,5-dimethoxyphenyl)isothiazolo[4,3-b]pyridine (100 mg, 0.221 mmol) in ethanol (10 ml) was added morpholine (3 eq, 57.7 mg). The reaction was stirred overnight at 75° C. The solvent was evaporated in vacuo and the crude residue was purified by silicagel flash chromatography, the mobile phase being a mixture of cyclohexane and ethylacetate (in a ratio of 1:1), affording the title compound in 80% yield.

$^1$H-NMR (300 MHz, CDCl$_3$) δ=3.87 (s, 3H, OCH$_3$), 3.92 (s, 3H, OCH$_3$), 3.95 (s, 8H), 6.86 (s, 1H, arom H), 7.14 (s, 1H, arom H), 7.75 (d, J=1.98 Hz, 1H, arom H), 8.43 (t, J=1.95 Hz, 1H, arom H). $^{13}$C-NMR (300 MHz, CDCl$_3$), 50.5 (CH2), 56.3 (CH$_3$), 56.4 (CH$_3$), 66.3 (CH2), 112.9 (C$_q$), 113.9 (CH), 116.1 (CH), 128.5 (CH), 130.9 (C$_q$), 134.1 (C$_q$), 136.3 (C$_q$), 146.0 (CH), 148.8 (C$_q$), 149.8 (C$_q$), 155.8 (C$_q$), 173.5 (C$_q$) ppm.

Examples 61-63

Synthesis of 3-morpholino-6-aryl-isothiazolo[4,3-b]pyridines

General Procedure

To a solution of 3-morpholino-6-bromo-isothiazolo[4,3-b]pyridine (0.2 mmol, 60 mg) in DME (2 ml) was added an appropriate boronic acid (1.5 eq, 0.3 mmol) and potassium carbonate (2 eq, 400 μl, 1M solution in H$_2$O). The mixture was degassed and Pd(PPh$_3$)$_4$ (10 mol %, 0.02 mmol, 23 mg) was added. The reaction was heated at 80° C. After completion of the reaction, solvents were evaporated. The crude residue was purified by silicagel flash chromatography, yielding the pure title compounds.

The following compounds were made according to this procedure:

Example 61

4-(6-(3-methoxyphenyl)isothiazolo[4,3-b]pyridin-3-yl)morpholine

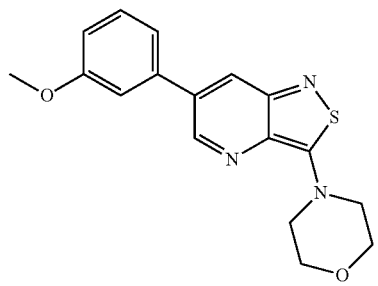 [SMILES: COc1cccc(-c2cnc3c(N4CCOCC4)snc3c2)c1]

This compound was prepared from 3-morpholino-6-bromo-isothiazolo[4,3-b]pyridine using 3-methoxyphenylboronic acid (46 mg). Product was purified using a mixture of cyclohexane/ethyl acetate in a ratio of 3:1, affording the title compound in 66% yield (43 mg, 0.133 mmol).

$^1$H-NMR (300 MHz, CDCl$_3$): δ=3.89 (s, 3H, OCH$_3$), 3.98 (m, 8H, 4×CH$_2$), 6.98 (dd, 1H, J=1.80 Hz, J=7.53 Hz arom H), 7.18-7.27 (m, 2H, arom H), 7.43 (t, 1H, J=7.98 Hz, arom H), 7.93 (bs, 1H, arom H), 8.65 (d, J=2.04 Hz, 1H, arom H) ppm.

Example 62

2-methoxy-5-(3-morpholinoisothiazolo[4,3-b]pyridin-6-yl)phenyl acetate

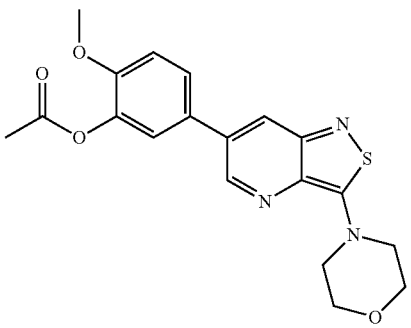 [SMILES: COc1ccc(-c2cnc3c(N4CCOCC4)snc3c2)cc1OC(C)=O]

This compound was prepared from 3-morpholino-6-bromo-isothiazolo[4,3-b]pyridine using 3-acetoxy-4-methoxyphenylboronic acid pinacol ester (87.6 mg). The crude product was purified using a mixture of cyclohexane/ethyl acetate in a ratio of 5:1, affording the title compound in 56% yield (43 mg, 0.112 mmol).

$^1$H-NMR (300 MHz, CDCl$_3$): δ=2.37 (s, 3H, CH$_3$ (acetyl)) 3.91 (s, 3H, OCH$_3$), 3.96 (m, 8H, 4×CH$_2$), 7.11 (d, J=8.58 Hz, 1H, arom H), 7.37 (d, J=2.25 Hz, 1H, arom H), 7.84 (dd, J=2.25 Hz, J=8.49 Hz, 1H, arom H), 7.87 (bs, 1H, arom H), 8.60 (d, J=2.01 Hz, 1H, arom H) ppm.

Example 63

4-(6-(4-methoxyphenyl)isothiazolo[4,3-b]pyridin-3-yl)morpholine

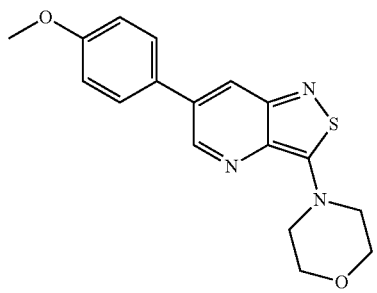 [SMILES: COc1ccc(-c2cnc3c(N4CCOCC4)snc3c2)cc1]

This compound was prepared from 3-morpholino-6-bromo-isothiazolo[4,3-b]pyridine using 4-methoxyphenylboronic acid (45.5 mg). The crude product was purified using a mixture of cyclohexane/ethyl acetate in a ratio of 5:1, affording the title compound in 73% yield (48 mg, 0.146 mmol).

$^1$H-NMR (300 MHz, CDCl$_3$): δ=3.75 (s, 3H, OCH$_3$), 3.97 (m, 8H, 4×CH$_2$), 7.06 (d, J=8.82 Hz, 2H, arom H), 7.63 (d, J=8.82 Hz, 2H, arom H), 7.87 (d, J=2.10 Hz, 1H, arom H), 8.64 (d, J=2.07 Hz, 1H, arom H) ppm.

Example 64

2-methoxy-4-(3-morpholinoisothiazolo[4,3-b]pyridin-6-yl)phenol

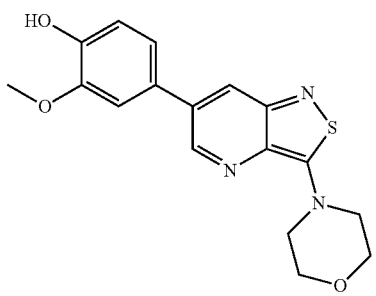

This compound was prepared from 3-morpholino-6-bromo-isothiazolo[4,3-b]pyridine (60 mg, 0.2 mmol) using methoxy-4-(4,4,5,5-tetramethyl-1,3,2-dioxaborolan-2-yl)phenol (0.3 mmol, 75 mg), 1M $K_2CO_3$ (0.4 ml) and $Pd(PPh_3)_4$ (0.02 mmol, 23 mg). Product was purified using a mixture of cyclohexane/ethyl acetate in a ratio of 3:2, affording the title compound in 44% yield (30 mg, 0.087 mmol).

1H-NMR (300 MHz, $CDCl_3$): δ=3.97 (m, 11H, 4×$CH_2$, $CH_3$), 5.93 (s, 1H, OH), 7.04 (d, J=8.16 Hz, 1H, arom H), 7.14 (d, J=1.95 Hz, 1H, arom H), 7.19 (dd, J=2.04 Hz, J=8.16 Hz, 1H, arom H), 7.87 (d, J=2.07 Hz, 1H, arom H), 8.64 (d, J=2.07 Hz, 1H, arom H) ppm.

Examples 65-76

Synthesis of 3-substituted 6-(3,4-dimethoxyphenyl)isothiazolo[4,3-b]pyridines General Procedure To a solution of 3,6-di-bromo-isothiazolo[4,3-b]pyridine in ethanol was added an appropriate nitrogen nucleophile (3 eq). The reaction was stirred at 75° C. After the reaction was finished, the solvent was evaporated in vacuo and the crude residue was purified by silicagel flash chromatography yielding the 3-substituted-6-bromo-isothiazolo[4,3-b]pyridine derivatives.

To a solution of this 3-substituted-6-bromo-isothiazolo[4,3-b]pyridine in DME (2 ml) was added an appropriate boronic acid (1.5 eq) and potassium carbonate (2 eq, 1M solution in $H_2O$). The reaction mixture was degassed and $Pd(PPh_3)_4$ (10 mol %) was added. The reaction was heated at 80° C. After the completion of the reaction, solvents were evaporated. The crude residue was purified by silicagel flash chromatography, yielding the pure title compounds.

The following compounds were made according to this procedure:

Example 65

1-(6-(3,4-dimethoxyphenyl)isothiazolo[4,3-b]pyridin-3-yl)piperidin-4-one

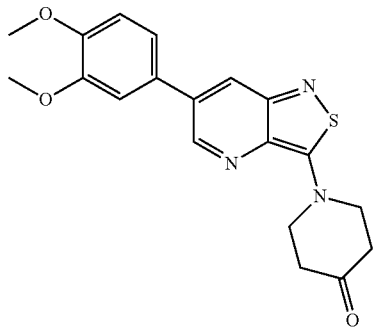 [SMILES: COc1ccc(-c2cnc3c(N4CCC(=O)CC4)snc3c2)cc1OC]

1-(6-bromoisothiazolo[4,3-b]pyridin-3-yl)piperidin-4-one was prepared from 3,6-di-bromo-isothiazolo[4,3-b]pyridine (146 mg, 0.5 mmol), piperidine-4-one hydrochloride (230 mg, 1.5 mmol) and DIPEA (0.256 ml, 1.50 mmol) in EtOH (10 ml). The crude product was purified using a mixture of cyclohexane/ethyl acetate in a ratio of 95:5, affording 1-(6-bromoisothiazolo[4,3-b]pyridin-3-yl)piperidin-4-one in 24% yield (38 mg, 0.121 mmol).

The title compound was prepared from 1-(6-bromoisothiazolo[4,3-b]pyridin-3-yl)piperidin-4-one (38 mg, 0.121 mmol) using 3,4-dimethoxyphenylboronic acid (0.181 mmol, 33 mg), 1M $K_2CO_3$ (0.24 ml) and $Pd(PPh_3)_4$ (0.012 mmol, 14 mg). The product was purified using a mixture of cyclohexane/ethyl acetate in a ratio of 1:1, affording the title compound in 53% yield (24.1 mg, 0.065 mmol).

$^1$H-NMR (300 MHz, $CDCl_3$): δ=2.76 (t, 4H, 2×$CH_2$), 3.97 (s, 3H, $OCH_3$), 3.98 (s, 3H, $OCH_3$), 4.39 (m, 4H, 2×$CH_2$), 7.03 (d, J=8.34 Hz, 1H, arom H), 7.19 (d, J=1.92 Hz, 1H, arom H), 7.25 (dd, J=2.04 Hz, 1H, arom H), 7.92 (d, J=1.92 Hz, 1H, arom H), 8.69 (d, J=1.98 Hz, 1H, arom H) ppm.

Example 66

1-(6-(3,4-dimethoxyphenyl)-isothiazolo[4,3-b]pyridin-3-yl)piperidin-4-ol

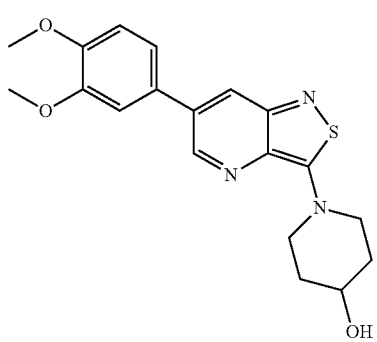 [SMILES: COc1ccc(-c2cnc3c(N4CCC(O)CC4)snc3c2)cc1OC]

1-(6-bromoisothiazolo[4,3-b]pyridin-3-yl)piperidin-4-ol was prepared from 3,6-di-bromo-isothiazolo[4,3-b]pyridine (0.5 mmol, 146 mg) and 4-hydroxypiperidine (1.5 mmol, 151 mg) in EtOH (10 ml). The crude product was purified using a mixture of DCM/MeOH in a ratio of 95:5, affording 1-(6-bromoisothiazolo[4,3-b]pyridin-3-yl)piperidin-4-ol in 82% yield (130 mg, 0.414 mmol).

The title compound was prepared from 1-(6-bromoisothiazolo[4,3-b]pyridin-3-yl)piperidin-4-ol (63 mg, 0.2 mmol) using 3,4-dimethoxyphenylboronic acid (0.3 mmol, 54.5 mg), 1M K$_2$CO$_3$ (0.4 ml) and Pd(PPh$_3$)$_4$ (0.02 mmol, 23 mg). The product was purified using a mixture of cyclohexane/ethyl acetate in a ratio of 1:1, affording the title compound in 57% yield (42.8 mg, 0.115 mmol).

1H-NMR (300 MHz, CDCl$_3$): δ=1.83 (m, 2H, CH$_2$), 2.09 (m, 2H, CH$_2$), 3.70 (m, 2H, CH$_2$), 3.94 (s, 3H, OCH$_3$), 3.96 (s, 3H, OCH$_3$), 4.06 (m, 1H, CH), 4.35 (m, 2H, CH$_2$), 6.97 (d, J=8.34 Hz, 1H, arom H), 7.17 (d, J=2.07 Hz, 1H, arom H), 7.24 (dd, J=8.28, J=2.07 Hz, 1H, arom H), 7.86 (d, J=2.01 Hz, 1H, arom H), 8.61 (d, J=2.04 Hz, 1H, arom H) ppm.

Example 67

5-(6-(3,4-dimethoxyphenyl)isothiazolo[4,3-b]pyridin-3-ylamino)pentan-1-ol

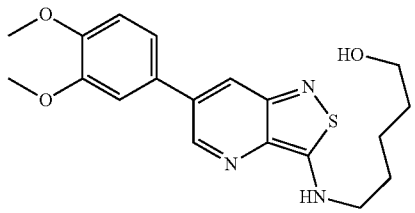 [SMILES: COc1ccc(-c2cnc3c(NCCCCCO)snc3c2)cc1OC]

5-(6-bromoisothiazolo[4,3-b]pyridin-3-ylamino)pentan-1-ol was prepared from 3,6-di-bromo-isothiazolo[4,3-b]pyridine (0.5 mmol, 146 mg) and 5-aminopentan-1-ol (1.5 mmol, 155 mg) in EtOH (10 ml). The product was purified using a mixture of DCM/MeOH in a ratio of 95:5, affording 5-(6-bromoisothiazolo[4,3-b]pyridin-3-ylamino)pentan-1-ol in 74% yield (118 mg, 0.373 mmol).

The title compound was prepared from 5-(6-bromoisothiazolo[4,3-b]pyridin-3-ylamino)pentan-1-ol (63 mg, 0.2 mmol) using 3,4-dimethoxyphenylboronic acid (0.3 mmol, 54.5 mg), 1M K$_2$CO$_3$ (0.4 ml) and Pd(PPh$_3$)$_4$ (0.02 mmol, 23 mg). The crude product was purified using a mixture of cyclohexane/ethyl acetate in a ratio of 1:3, affording the title compound in 12% yield (8.9 mg, 0.024 mmol).

1H-NMR (300 MHz, CDCl$_3$): δ=1.66 (m, 4H, 2×CH$_2$), 1.86 (m, 2H, CH2), 3.42 (m, 2H, CH$_2$), 3.74 (m, 2H, CH$_2$), 3.96 (s, 3H, OCH$_3$), 3.98 (s, 3H, OCH$_3$), 6.36 (t, 1H, NH), 7.02 (d, J=8.34 Hz, 1H, arom H), 7.16 (d, J=2.07 Hz, 1H, arom H), 7.24 (dd, J=8.25, J=2.07 Hz, 1H, arom H), 7.88 (d, J=1.92 Hz, 1H, arom H), 8.57 (d, J=1.95 Hz, 1H, arom H) ppm.

Example 68

1-(6-(3,4-dimethoxyphenyl)isothiazolo[4,3-b]pyridin-3-yl)piperidin-3-ol

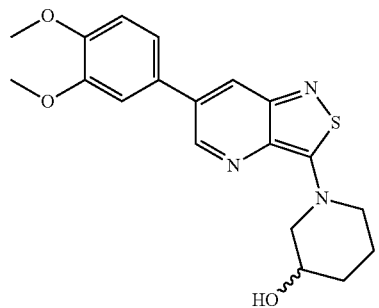 [SMILES: COc1ccc(-c2cnc3c(N4CCCC(O)C4)snc3c2)cc1OC]

1-(6-bromoisothiazolo[4,3-b]pyridin-3-yl)piperidin-3-ol was prepared from 3,6-di-bromo-isothiazolo[4,3-b]pyridine (0.5 mmol, 146 mg) and 3-hydroxypiperidine (1.5 mmol, 151 mg) in EtOH (10 ml). The product was purified using a mixture of cyclohexane/ethyl acetate in a ratio of 1:1, affording 1-(6-bromoisothiazolo[4,3-b]pyridin-3-yl)piperidin-3-ol in 89% yield (140 mg, 0.144 mmol).

The title compound was prepared from 1-(6-bromoisothiazolo[4,3-b]pyridin-3-yl)piperidin-3-ol (62.8 mg, 0.2 mmol) using 3,4-dimethoxyphenylboronic acid (0.3 mmol, 54.5 mg), 1M K$_2$CO$_3$ (0.4 ml) and Pd(PPh$_3$)$_4$ (0.02 mmol, 23 mg). The product was purified using a mixture of cyclohexane/ethyl acetate in a ratio of 1:1, affording the title compound in 24% yield (18 mg, 0.048 mmol).

$^1$H-NMR (300 MHz, CDCl$_3$): δ=1.80-2.1 (m, 5H, CH, 2×CH$_2$), 3.64 (m, 1H, CH), 3.95 (s, 3H, OCH$_3$), 3.97 (s, 3H, OCH$_3$), 4.13 (m, 3H, CH, CH$_2$), 6.99 (d, J=8.34 Hz, 1H, arom H), 7.17 (d, J=2.04 Hz, 1H, arom H), 7.24 (dd, J=8.28, J=2.07 Hz, 1H, arom H), 7.85 (d, J=2.01 Hz, 1H, arom H), 8.61 (d, J=2.04 Hz, 1H, arom H) ppm.

Example 69

6-(3,4-dimethoxyphenyl)-N-(tetrahydro-2H-pyran-4-yl)isothiazolo[4,3-]pyridin-3-amine

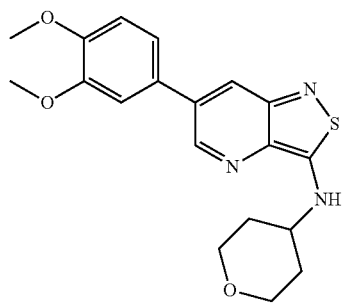 [SMILES: COc1ccc(-c2cnc3c(NC4CCOCC4)snc3c2)cc1OC]

6-bromo-N-(tetrahydro-2H-pyran-4-yl)isothiazolo[4,3-b]pyridin-3-amine was prepared from 3,6-di-bromo-isothiazolo[4,3-b]pyridine (0.5 mmol, 146 mg) and 4-aminopyrane (0.151 ml, 1.5 mmol) in EtOH (10 ml). The product was purified using a mixture of cyclohexane/ethyl acetate in a ratio of 3:1, affording 6-bromo-N-(tetrahydro-2H-pyran-4-yl)isothiazolo[4,3-b]pyridin-3-amine in 40% yield (64 mg, 0.203 mmol).

The title compound was prepared from 6-bromo-N-(tetrahydro-2H-pyran-4-yl)isothiazolo[4,3-b]pyridin-3-amine (64 mg, 0.203 mmol) using 3,4-dimethoxyphenylboronic acid (0.304 mmol, 55.3 mg), 1M $K_2CO_3$ (0.406 ml) and $Pd(PPh_3)_4$ (0.02 mmol, 23 mg). Product was purified using a mixture of cyclohexane/ethyl acetate in a ratio of 1:1, affording the title compound in 16% yield (5.5 mg, 0.015 mmol).

$^1$H-NMR (300 MHz, CDCl$_3$): δ=1.72 (m, 2H, 2×CH$_2$), 2.25 (m, 2H, CH$_2$), 3.54 (m, 3H, CH, CH$_2$) 3.95 (s, 3H, OCH$_3$), 3.97 (s, 3H, OCH$_3$), 4.12 (m, 2H, CH$_2$), 6.26 (d, J=7.59, 1H, NH) 6.99 (d, J=8.34 Hz, 1H, arom H), 7.16 (d, J=2.04 Hz, 1H, arom H), 7.24 (dd, J=8.28, J=2.04 Hz, 1H, arom H), 7.89 (d, J=1.89 Hz, 1H, arom H), 8.59 (d, J=1.89 Hz, 1H, arom H) ppm.

Example 70

2,2'-(6-(3,4-dimethoxyphenyl)isothiazolo[4,3-b]pyridin-3-ylazanediyl)diethanol

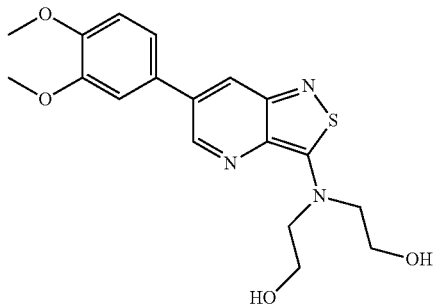 [SMILES: COc1ccc(-c2cnc3c(N(CCO)CCO)snc3c2)cc1OC]

2,2'-(6-bromoisothiazolo[4,3-b]pyridin-3-ylazanediyl)diethanol was prepared from 3,6-di-bromo-isothiazolo[4,3-b]pyridine (0.5 mmol, 146 mg) and diethanolamine (0.145 ml, 1.5 mmol) in EtOH (10 ml). The product was purified using a mixture of DCM/MeOH in a ratio of 95:5, affording 2,2'-(6-bromoisothiazolo[4,3-b]pyridin-3-ylazanediyl)diethanol in 81% yield (129 mg, 0.405 mmol).

The title compound was prepared from 2,2'-(6-bromoisothiazolo[4,3-b]pyridin-3-ylazanediyl)diethanol (63.6 mg, 0.2 mmol) using 3,4-dimethoxyphenylboronic acid (0.3 mmol, 54.5 mg), 1M $K_2CO_3$ (0.4 ml) and $Pd(PPh_3)_4$ (0.02 mmol, 23 mg). The crude product was purified using a mixture of DCM/MeOH in a ratio of 100:1, affording the title compound in 60% yield (45 mg, 0.12 mmol).

$^1$H-NMR (300 MHz, CDCl$_3$): δ=3.96 (s, 3H, OCH$_3$), 3.98 (s, 3H, OCH$_3$), 4.05 (m, 8H, 4×CH$_2$), 4.20 (m, 2H, 2×OH), 7.02 (d, J=8.31 Hz, 1H, arom H), 7.15 (d, J=2.04 Hz, 1H, arom H), 7.24 (dd, J=8.28, J=2.13 Hz, 1H, arom H), 7.86 (d, J=2.04 Hz, 1H, arom H), 8.56 (d, J=2.04 Hz, 1H, arom H) ppm.

Example 71

3-(6-(3,4-dimethoxyphenyl)isothiazolo[4,3-b]pyridin-3-ylamino)propane-1,2-diol

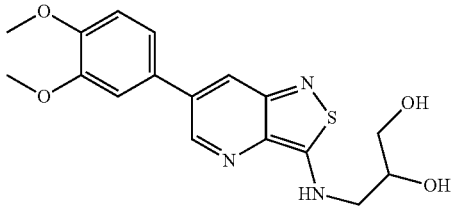 [SMILES: COc1ccc(-c2cnc3c(NCC(O)CO)snc3c2)cc1OC]

3-(6-bromoisothiazolo[4,3-b]pyridin-3-ylamino)propane-1,2-diol was prepared from 3,6-di-bromo-isothiazolo[4,3-b]pyridine (0.5 mmol, 146 mg) and 3-amino-1,2-propanediol (137 mg, 1.5 mmol) in EtOH (10 ml). The product was purified using a mixture of DCM/MeOH in a ratio of 95:5, affording 3-(6-bromoisothiazolo[4,3-b]pyridin-3-ylamino)propane-1,2-diol in 65% yield (99 mg, 0.325 mmol).

The title compound was prepared from 3-(6-bromoisothiazolo[4,3-b]pyridin-3-ylamino)propane-1,2-diol (60.8 mg, 0.2 mmol) using 3,4-dimethoxyphenylboronic acid (0.3 mmol, 54.5 mg), 1M $K_2CO_3$ (0.4 ml) and $Pd(PPh_3)_4$ (0.02 mmol, 23 mg). Product was purified using a mixture of DCM/MeOH in a ratio of 100:1, affording the title compound in 66% yield (48 mg, 0.132 mmol).

$^1$H-NMR (300 MHz, DMSO): δ=3.30-3.50 (m, 4H, 2×CH2), 3.82 (s, 3H, OCH$_3$), 3.84 (m, 1H, CH), 3.88 (s, 3H, OCH$_3$), 4.74 (t, 1H, OH), 5.05 (d, 1H, OH), 7.07 (d, J=8.76 Hz, 1H, arom H), 7.35 (m, 3H, arom H), 7.92 (s, 1H, arom H), 8.27 (t, 1H, NH), 8.64 (s, 1H, arom H) ppm.

Example 72 ethyl 4-(6-(3,4-dimethoxyphenyl)isothiazolo[4,3-b]pyridin-3-ylamino)piperidine-1-carboxylate

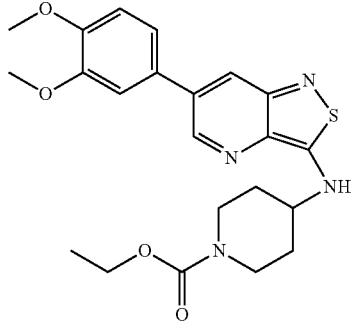 [SMILES: CCOC(=O)N1CCC(Nc2snc3cc(-c4ccc(OC)c(OC)c4)cnc23)CC1]

ethyl 4-(6-bromoisothiazolo[4,3-b]pyridin-3-ylamino)piperidine-1-carboxylate was prepared from 3,6-di-bromo-isothiazolo[4,3-b]pyridine (1.0 mmol, 293 mg) and ethyl 4-amino-1-piperidinecarboxylate (0.53 ml, 3.0 mmol) in EtOH (10 ml). The product was purified using a mixture of cyclohexane/ethylacetate in a ratio of 4:1, affording the ethyl 4-(6-bromoisothiazolo[4,3-b]pyridin-3-ylamino)piperidine-1-carboxylate in 42% yield (162 mg, 0.420 mmol).

The title compound was prepared from ethyl 4-(6-bromoisothiazolo[4,3-b]pyridin-3-ylamino)piperidine-1-carboxylate (162 mg, 0.42 mmol) using 3,4-dimethoxyphenylboronic acid (0.63 mmol, 114 mg), 1M $K_2CO_3$ (0.84 ml) and $Pd(PPh_3)_4$ (0.042 mmol, 48 mg). Product was purified using a mixture of cyclohexane/ethylacetate in a ratio of 1:1, affording the title compound in 13% yield (25 mg, 0.056 mmol).

$^1$H-NMR (300 MHz, CDCl$_3$): δ=1.27 (t, J=7.05 Hz, J=7.17 Hz, 1H, CH$_3$), 1.65 (m, 2H, CH$_2$), 2.23 (m, 1H, CH$_2$), 3.02 (m, 2H, CH$_2$), 3.47 (m, 1H, CH), 3.93 (s, 3H, OCH$_3$), 3.95 (s, 3H, OCH$_3$), 4.19 (m, 4H, CH$_2$, OCH$_2$) 6.34 (d, J=7.53 Hz, 1H, NH), 6.99 (d, J=8.28 Hz, 1H, arom H), 7.14 (d, 1H, J=1.83 Hz, arom H), 7.20 (dd, J=8.25, J=1.77 Hz, 1H, arom H), 7.86 (d, J=1.53 Hz, 1H, arom H), 8.64 (d, J=1.53 Hz, 1H, arom H) ppm.

Example 73

6-(3,4-dimethoxyphenyl)-3-(pyrrolidin-1-yl)isothiazolo[4,3-b]pyridine

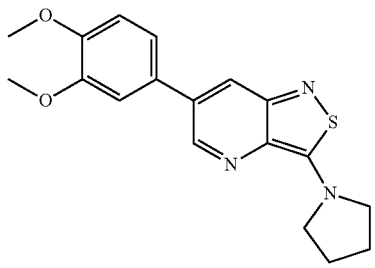 [SMILES: COc1ccc(-c2cnc3c(N4CCCC4)snc3c2)cc1OC]

6-bromo-3-(pyrrolidin-1-yl)isothiazolo[4,3-b]pyridine was prepared from 3,6-di-bromo-isothiazolo[4,3-b]pyridine (0.5 mmol, 146 mg) and pyrrolidine (0.04 ml, 1.5 mmol) in EtOH (10 ml). Product was purified using a mixture of cyclohexane/ethylacetate in a ratio of 4:1, affording the 6-bromo-3-(pyrrolidin-1-yl)isothiazolo[4,3-b]pyridine in 90% yield (128 mg, 0.450 mmol).

The title compound was prepared from 6-bromo-3-(pyrrolidin-1-yl)isothiazolo[4,3-b]pyridine (71 mg, 0.25 mmol) using 3,4-dimethoxyphenylboronic acid (0.375 mmol, 68 mg), 1M K$_2$CO$_3$ (0.50 ml) and Pd(PPh$_3$)$_4$ (0.025 mmol, 29 mg). The product was purified using a mixture of cyclohexane/ethylacetate in a ratio of 3:2, affording the title compound in 63% yield (54 mg, 0.158 mmol).

$^1$H-NMR (300 MHz, CDCl$_3$): δ=2.17 (m, 4H, 2×CH$_2$), 3.87 (m, 4H, 2×CH$_2$), 3.96 (s, 3H, OCH$_3$), 3.98 (s, 3H, OCH$_3$), 7.00 (d, J=8.28 Hz, 1H, arom H), 7.18 (d, 1H, J=2.01 Hz, arom H), 7.26 (dd, J=8.52, J=2.28 Hz, 1H, arom H), 7.82 (d, J=1.95 Hz, 1H, arom H), 8.58 (d, J=1.95 Hz, 1H, arom H) ppm.

Example 74

6-(3,4-dimethoxyphenyl)-N-phenethylisothiazolo[4,3-b]pyridin-3-amine

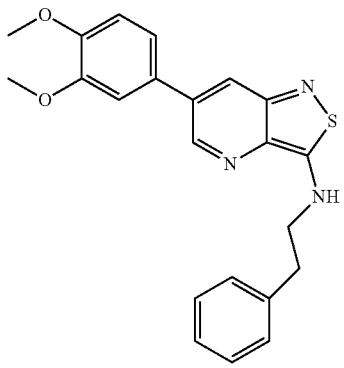 [SMILES: COc1ccc(-c2cnc3c(NCCc4ccccc4)snc3c2)cc1OC]

6-bromo-N-phenethylisothiazolo[4,3-b]pyridin-3-amine was prepared from 3,6-di-bromo-isothiazolo[4,3-b]pyridine (0.5 mmol, 146 mg) and phenethylamine (0.188 ml, 1.5 mmol) in EtOH (10 ml). The product was purified using a mixture of cyclohexane/ethylacetate in a ratio of 4:1, affording the 6-bromo-N-phenethylisothiazolo[4,3-b]pyridin-3-amine in 77% yield (130 mg, 0.389 mmol).

The title compound was prepared from 6-bromo-N-phenethylisothiazolo[4,3-b]pyridin-3-amine (130 mg, 0.389 mmol) using 3,4-dimethoxyphenylboronic acid (0.583 mmol, 106 mg), 1M K$_2$CO$_3$ (0.78 ml) and Pd(PPh$_3$)$_4$ (0.038 mmol, 45 mg). Product was purified using a mixture of cyclohexane/ethylacetate in a ratio of 9:1, affording the title compound in 25% yield (39 mg, 0.099 mmol).

$^1$H-NMR (300 MHz, CDCl$_3$): δ=3.11 (t, J=7.05 Hz, 1H, CH$_2$), 3.66 (m, 2H, CH$_2$), 3.95 (s, 3H, OCH$_3$), 3.97 (s, 3H, OCH$_3$), 6.36 (m, 1H, NH) 7.01 (d, J=8.31 Hz, 1H, arom H), 7.15 (d, 1H, J=1.89 Hz, arom H), 7.21-7.37 (m, 6H, arom H), 7.87 (d, J=1.86 Hz, 1H, arom H), 8.66 (d, J=1.83 Hz, 1H, arom H) ppm.

Example 75

6-(3,4-dimethoxyphenyl)-N-(2-methoxyethyl)isothiazolo[4,3-b]pyridin-3-amine

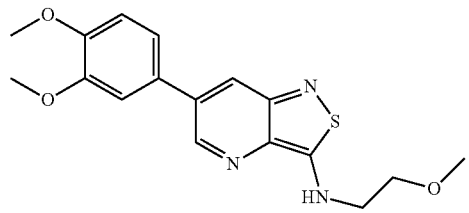

6-bromo-N-(2-methoxyethyl)isothiazolo[4,3-b]pyridin-3-amine was prepared from 3,6-di-bromo-isothiazolo[4,3-b]pyridine (0.5 mmol, 146 mg) and 2-methoxyethylamine (0.13 ml, 1.5 mmol) in EtOH (10 ml). The product was purified using a mixture of cyclohexane/ethylacetate in a ratio of 4:1, affording the 6-bromo-N-(2-methoxyethyl)isothiazolo[4,3-b]pyridin-3-amine in 83% yield (120 mg, 0.416 mmol).

The title compound was prepared from 6-bromo-N-(2-methoxyethyl)isothiazolo[4,3-b]pyridin-3-amine (57 mg, 0.2 mmol) using 3,4-dimethoxyphenylboronic acid (0.3 mmol, 54.5 mg), 1M K$_2$CO$_3$ (0.40 ml) and Pd(PPh$_3$)$_4$ (0.02 mmol, 23 mg). Product was purified using a mixture of cyclohexane/ethylacetate in a ratio of 1:1, affording the title compound in 22% yield (15 mg, 0.043 mmol).

$^1$H-NMR (300 MHz, CDCl$_3$): δ=3.40 (s, 3H, OCH$_3$), 3.55 (m, 2H, CH$_2$), 3.58 (m, 2H, CH$_2$), 3.95 (s, 3H, OCH$_3$), 3.97 (s, 3H, OCH$_3$), 6.53 (m, 1H, NH), 6.99 (d, J=8.31 Hz, 1H, arom H), 7.15 (d, 1H, J=1.98 Hz, arom H), 7.21 (dd, J=1.98 Hz, J=8.22 Hz, 1H, arom H), 7.87 (d, J=1.80 Hz, 1H, arom H), 8.60 (d, J=1.80 Hz, 1H, arom H) ppm.

Example 76

N-(cyclopropylmethyl)-6-(3,4-dimethoxyphenyl)isothiazolo[4,3-b]pyridin-3-amine

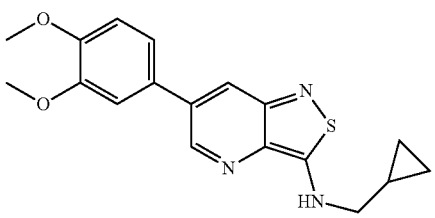 [SMILES: COc1ccc(-c2cnc3c(NCC4CC4)snc3c2)cc1OC]

6-bromo-N-(cyclopropylmethyl)isothiazolo[4,3-b]pyridin-3-amine was prepared from 3,6-di-bromo-isothiazolo[4,3-b]pyridine (0.5 mmol, 146 mg) and aminomethylcyclopropane (0.086 ml, 3.0 mmol) in EtOH (10 ml). The product was purified using a mixture of cyclohexane/ethylacetate in a ratio of 9:1, affording the 6-bromo-N-(cyclopropylmethyl)isothiazolo[4,3-b]pyridin-3-amine in 84% yield (120 mg, 0.422 mmol).

The title compound was prepared from 6-bromo-N-(cyclopropylmethyl)isothiazolo[4,3-b]pyridin-3-amine (85 mg, 0.3 mmol) using 3,4-dimethoxyphenylboronic acid (0.45 mmol, 82 mg), 1M $K_2CO_3$ (0.60 ml) and $Pd(PPh_3)_4$ (0.03 mmol, 34 mg). Product was purified using a mixture of cyclohexane/ethylacetate in a ratio of 4:1, affording the title compound in 73% yield (75 mg, 0.210 mmol).

$^1$H-NMR (300 MHz, $CDCl_3$): δ=0.67 (q, 2H, $CH_2$), 0.69 (q, 2H, $CH_2$), 1.25 (m, 1H, CH), 3.24 (q, 2H, $NCH_2$), 3.96 (s, 3H, $OCH_3$), 3.98 (s, 3H, $OCH_3$), 6.36 (t, 1H, NH), 7.02 (d, J=8.34 Hz, 1H, arom H), 7.17 (d, J=2.07 Hz, 1H, arom H), 7.25 (dd, J=8.28, J=2.1 Hz, 1H, arom H), 7.88 (d, J=1.92 Hz, 1H, arom H), 8.59 (d, J=1.95 Hz, 1H, arom H) ppm.

Example 77

Synthesis of 3-bromo-6-(4,5-dimethoxyphenyl)isothiazolo[4,3-b]pyridine

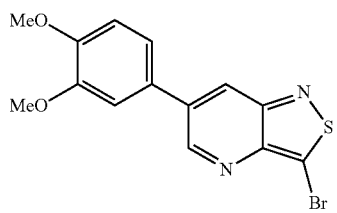 [SMILES: COc1ccc(-c2cnc3c(Br)snc3c2)cc1OC]

To a solution of 3-amino-6-(3,4-dimethoxyphenyl)-isothiazolo[4,3-b]pyridine (1 g, 3.5 mmol) in HBr (20 ml) at 0° C., was added portionwise sodium nitrite (2 eq, 0.48 g). After 30 minutes, CuBr (2 eq, 1.33 g) was added. The reaction mixture was stirred for two hours, at 0° C. and then stirred at room temperature overnight. The mixture was neutralized with solid potassium carbonate and extracted with ethyl acetate (2×50 ml). The combined organic phases were dried over $MgSO_4$ and evaporated in vacuo. The crude residue was purified by silica gel flash chromatography, the mobile phase being a mixture of cyclohexane and ethylacetate (in a ratio of 9:1), yielding the pure title compound (0.38 g, 31%).

$^1$H-NMR (300 MHz, $CDCl_3$) δ=3.96 (s, 3H, $OCH_3$), 3.99 (s, 3H, $OCH_3$), 7.02 (d, J=8.3 Hz, 1H, arom H), 7.20 (s, 1H, arom H), 7.28 (dd, J=2.2; 8.3 Hz, 1H arom H), 8.21 (dd, J=1.0; 2.0 Hz, 1H, arom H), 9.08 (d, J=1.9 Hz, 1H, arom H) ppm.

Examples 78-81

Synthesis of 3-substituted 6-(3,4-dimethoxyphenyl)-isothiazolo[4,3-b]pyridines

General Procedure

To a solution of 3-bromo-6-(4,5-dimethoxyphenyl)isothiazolo[4,3-b]pyridine (100 mg, 0.285 mmol) in ethanol (10 ml) was added an appropriate amine (3 eq, 0.855 mmol). The reaction was stirred overnight at 75° C. The solvent was evaporated in vacuo and the crude residue was purified by silicagel flash chromatography yielding the pure title compounds.

The following compounds were made according to this procedure:

Example 78

6-(3,4-dimethoxyphenyl)-N,N-dimethylisothiazolo[4,3-b]pyridin-3-amine

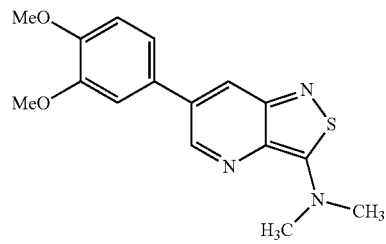 [SMILES: COc1ccc(-c2cnc3c(N(C)C)snc3c2)cc1OC]

This compound was prepared using dimethylamine and was purified using a mixture of cyclohexane and ethylacetate (in a ratio of 1:1), affording the title compound in 98% yield. $^1$H-NMR (300 MHz, $CDCl_3$) δ=3.49 (s, 6H, 2×$CH_3$), 3.94 (s, 3H, $OCH_3$), 3.99 (s, 3H, $OCH_3$), 6.97 (d, J=8.3 Hz, 1H, arom H), 7.15 (s, 1H, arom H), 7.21 (dd, J=2.1; 8.3 Hz, 1H arom H), 7.80 (d, J=2.0 Hz, 1H, arom H), 8.56 (d, J=2.0 Hz, 1H, arom H) ppm.

Example 79

6-(3,4-dimethoxyphenyl)-N,N-diethylisothiazolo[4,3-b]pyridin-3-amine

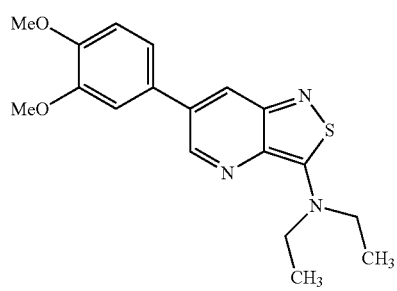 [SMILES: CCN(CC)c1snc2cc(-c3ccc(OC)c(OC)c3)cnc12]

This compound was prepared using diethylamine and was purified using a mixture of cyclohexane and ethylacetate (in a ratio of 1:1), affording the title compound in 80% yield.

¹H-NMR (300 MHz, CDCl₃) δ=1.34 (t, J=7.1 Hz, 6H, 2×CH₃), 3.93 (m, 10H, 2×OCH₃, 2×NCH₂), 6.97 (d, J=8.3 Hz, 1H, arom H), 7.16 (s, 1H, arom H), 7.22 (dd, J=2.1; 8.3 Hz, 1H arom H), 7.79 (d, J=2.1 Hz, 1H, arom H), 8.56 (d, J=2.1 Hz, 1H, arom H) ppm.

Example 80

(2R,6S)-4-(6-(3,4-dimethoxyphenyl)isothiazolo[4,3-b]pyridin-3-vi)-2,6-dimethylmorpholine

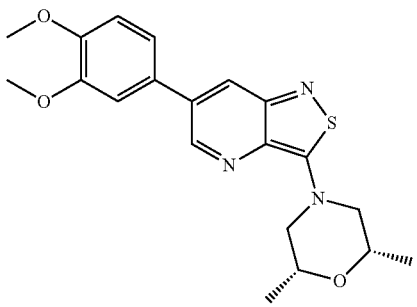

This compound was prepared using cis-2,6-dimethylmorpholine and was purified using a mixture of cyclohexane and ethylacetate (in a ratio of 1:1), affording the title compound in 78% yield.

¹H-NMR (300 MHz, CDCl₃) δ=1.31 (d, J=6.3 Hz, 6H, 2×CH₃), 2.90 (t, J=11.7 Hz, 2H, 2×NCH), 3.94 (m, 8H, 2×OCH₃, 2×OCH), 4.50, (d, J=12.6 Hz, 2×NCH), 6.98 (d, J=8.4 Hz, 1H, arom H), 7.15 (d, J=2.1 Hz, 1H, arom H), 7.23 (dd, J=2.2; 8.3 Hz, 1H arom H), 7.84 (d, J=2.1 Hz, 1H, arom H), 8.62 (d, J=2.1 Hz, 1H, arom H) ppm.

Example 81

8-(6-(3,4-dimethoxyphenyl)isothiazolo[4,3-b]pyridin-3-yl)-1,4-dioxa-8-azaspiro[4,5]decane

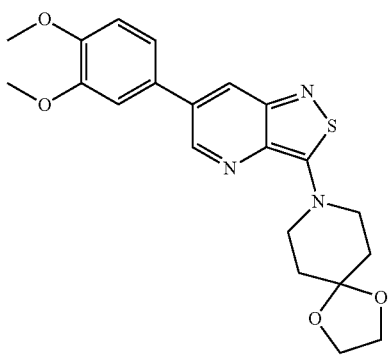 [SMILES: COc1ccc(-c2cnc3c(N4CCC5(CC4)OCCO5)snc3c2)cc1OC]

This compound was prepared using 1,4-dioxa-8-aza-spiro[4.5]decane and was purified using a mixture of cyclohexane and ethylacetate (in a ratio of 1:1), affording the title compound in 65% yield.

¹H-NMR (300 MHz, CDCl₃) δ=1.95 (t, J=5.9 Hz, 4H, 2×CCH₂), 3.93 (s, 3H, OCH₃), 3.95 (s, 3H, OCH₃), 4.01, (s, 4H, 2×OCH₂), 4.08 (t, J=5.8 Hz, 4H, 2×NCH₂), 6.98 (d, J=8.3 Hz, 1H, arom H), 7.15 (d, J=2.0 Hz, 1H, arom H), 7.22 (dd, J=2.1; 8.3 Hz, 1H arom H), 7.83 (d, J=2.0 Hz, 1H, arom H), 8.61 (d, J=1.9 Hz, 1H, arom H) ppm.

Examples 82-85

Synthesis of 3-aryl-6-(4,5-dimethoxyphenyl)isothiazolo[4,3-b]pyridines

General Procedure

To a solution of 3-bromo-6-(4,5-dimethoxyphenyl)isothiazolo[4,3-b]pyridine (25 mg, 0.067 mmol) in a mixture of dioxane (10 ml) and water (1.5 ml) was added an appropriate arylboronic acid (2 eq), sodium carbonate (2 eq, 16.3 mg) and Pd(dppf)Cl₂ (0.1 eq, 5.4 mg) The reaction mixture was stirred overnight at 100° C. The reaction mixture was cooled down to room temperature and the reaction was partioned between ethylacetate (30 ml) and brine (15 ml). The aqueous phase was then extracted with ethyl acetate (30 ml). The combined organic phases were dried over MgSO₄ and evaporated in vacuo. The residue was purified by flash chromatography on silicagel yielding the pure title compounds.

The following compounds were made according to this procedure:

Example 82

6-(3,4-dimethoxyphenyl)-3-phenylisothiazolo[4,3-b]pyridine

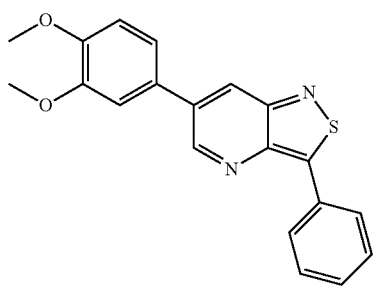 [SMILES: COc1ccc(-c2cnc3c(-c4ccccc4)snc3c2)cc1OC]

This compound was prepared using phenylboronic acid and was purified using a mixture of cyclohexane and ethylacetate (in a ratio of 1:1), affording the title compound in 52% yield.

¹H-NMR (300 MHz, CDCl₃) δ=3.96 (s, 3H, OCH₃), 3.99 (s, 3H, OCH₃), 7.03 (d, J=8.3 Hz, 1H, arom H), 7.21 (d, J=2.4 Hz, 1H, arom H), 7.30 (dd, J=2.1; 8.3 Hz, 1H, arom H), 7.53 (m, 3H, arom H), 8.19 (m, 3H, arom H), 9.11 (d, J=2.1 Hz, 1H, arom H) ppm.

Example 83

6-(3,4-dimethoxyphenyl)-3-(pyridin-4-yl)isothiazolo[4,3-b]pyridine

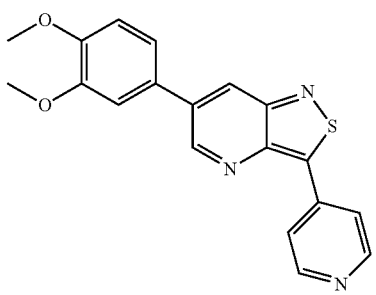 [SMILES: COc1ccc(-c2cnc3c(-c4ccncc4)snc3c2)cc1OC]

This compound was prepared using pyridine-4-boronic acid and was purified using a mixture of cyclohexane and ethylacetate (in a ratio of 1:1), affording the title compound in 48% yield.

$^1$H-NMR (300 MHz, CDCl$_3$) δ=3.97 (s, 3H, OCH$_3$), 3.99 (s, 3H, OCH$_3$), 7.03 (d, J=8.3 Hz, 1H, arom H), 7.21 (d, J=2.0 Hz, 1H, arom H), 7.30 (dd, J=1.9; 8.3 Hz, 1H, arom H), 8.13 (d, J=6.0 Hz, 2H, arom H), 8.21 (d, J=1.9 Hz, 1H, arom H), 8.80 (d, J=5.6 Hz, 1H, arom H), 9.16 (d, J=1.9 Hz, 1H, arom H) ppm.

Example 84

6-(3,4-dimethoxyphenyl-3-(thiophen-3-isothiazolo[4,3-b]pyridine

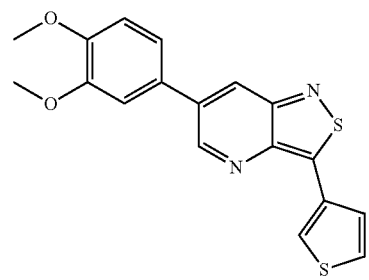 [SMILES: COc1ccc(-c2cnc3c(-c4ccsc4)snc3c2)cc1OC]

This compound was prepared using 3-thienylboric acid and was purified using a mixture of cyclohexane and ethylacetate (in a ratio of 1:1), affording the title compound in 56% yield.

$^1$H-NMR (300 MHz, CDCl$_3$) δ=3.96 (s, 3H, OCH$_3$), 3.99 (s, 3H, OCH$_3$), 7.03 (d, J=8.3 Hz, 1H, arom H), 7.21 (d, J=2.1 Hz, 1H, arom H), 7.30 (dd, J=2.1; 8.3 Hz, 1H, arom H), 7.51 (m, 1H, arom H), 7.76 (dd, J=1.2; 5.0 Hz, 1H, arom H), 8.14 (d, J=2.1 Hz, 1H, arom H), 8.52 (t, J=1.8 Hz, 1H, arom H), 9.08 (d, J=2.1 Hz, 1H, arom H) ppm.

Example 85

6-(3,4-dimethoxyphenyl)-isothiazolo[4,3-b]pyridine

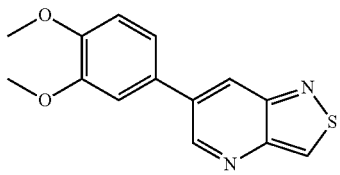 [SMILES: COc1ccc(-c2cnc3csnc3c2)cc1OC]

This compound was isolated as the major compound when using 3,5-dimethylisoxazole-4-boronic acid. The crude residue was purified using a mixture of cyclohexane and ethylacetate (in a ratio of 1:1), affording the title compound in 42% yield.

$^1$H-NMR (300 MHz, CDCl$_3$) δ=3.96 (s, 3H, OCH$_3$), 3.99 (s, 3H, OCH$_3$), 7.02 (d, J=8.3 Hz, 1H, arom H), 7.20 (d, J=2.1 Hz, 1H, arom H), 7.29 (dd, J=2.1; 8.3 Hz, 1H, arom H), 8.22 (s, 1H, arom H), 9.08 (d, J=2.0 Hz, 1H, arom H), 9.49 (s, 1H, arom H) ppm.

Examples 86-87

Synthesis of 3-bromo-6-(2-bromo-4,5-dimethoxyphenyl)isothiazolo[4,3-b]pyridines

General Procedure

To a solution of 3-bromo-6-(2-bromo-4,5-dimethoxyphenyl)isothiazolo[4,3-b]pyridine (50 mg, 0.116 mmol) in ethanol (10 ml) was added amine (3 eq, 0.349 mmol). The reaction was stirred overnight at 75° C. The solvent was evaporated in vacuo and the crude residue was purified by silicagel flash chromatography yielding the pure title compounds.

The following compounds were made according to this procedure:

Example 86

6-(2-bromo-4,5-dimethoxyphenyl)-3-(4-methylpiperidin-1-yl)isothiazolo[4,3-b]pyridine

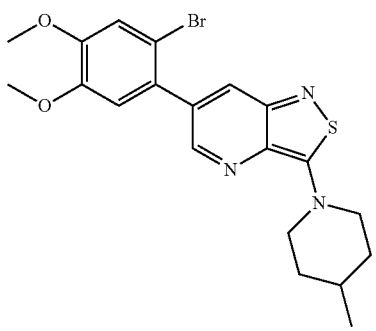 [SMILES: COc1cc(Br)c(-c2cnc3c(N4CCC(C)CC4)snc3c2)cc1OC]

This compound was prepared using 4-methylpiperidine and was purified using a mixture of cyclohexane and ethylacetate (in a ratio of 1:1), affording the title compound in 65% yield. $^1$H-NMR (300 MHz, CDCl$_3$) δ=1.02 (d, J=6.3 Hz, 3H, CH$_3$), 1.55 (m, 3H, CHCH$_3$, 2×CHCH$_2$), 1.84 (d, J=14.6 Hz, 2H, 2×CHCH$_2$), 2.22 (t, J=12.76 Hz, 2H, 2×NCH$_2$), 3.87 (s, 3H, OCH$_3$), 3.93 (s, 3H, OCH$_3$), 4.69, (d, J=12.9 Hz, 2×NCH$_2$), 6.97 (s, 1H, arom H), 7.15 (s, 1H, arom H), 7.71 (d, J=2.0 Hz, 1H, arom H), 8.40 (d, J=2.0 Hz, 1H, arom H) ppm.

Example 87

6-(2-bromo-4,5-dimethoxyphenyl)-3-ethoxyisothiazolo[4,3-b]pyridine

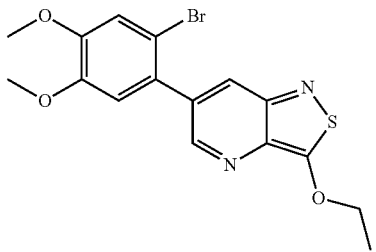 [SMILES: CCOc1snc2cc(-c3cc(OC)c(OC)cc3Br)cnc12]

This compound was isolated as the major compound when using 2-methylpiperidine as nitrogen nucleophile. The crude residue was purified using a mixture of cyclohexane and ethylacetate (in a ratio of 1:1), affording the title compound in 55% yield.

$^1$H-NMR (300 MHz, CDCl$_3$) δ=1.68 (t, J=7.0 Hz, 3H, CH$_3$), 3.88 (s, 3H, OCH$_3$), 3.92 (s, 3H, OCH$_3$), 4.54 (q, J=7.0 Hz, 2H, CH$_2$), 6.87 (s, 1H, arom H), 7.15 (s, 1H, arom H), 7.83 (d, J=1.9 Hz, 1H, arom H), 8.65 (d, J=1.8 Hz, 1H, arom H) ppm.

Example 88

GAK binding assay

The compounds of the invention were assayed for their GAK kinase binding affinity using the protocols, as described in Fabian, M. A. et al. A small molecule-kinase interaction map for clinical kinase inhibitors. *Nat. Biotechnol.* 23, 329-336 (2005). Table 1 summarizes the biological data.

Kinase Assays.

T7 kinase-tagged phage strains were grown in parallel in 24- or 96-well blocks in an *E. coli* host derived from the BL21 strain. *E. coli* were grown to log phase and infected with T7 phage from a frozen stock (multiplicity of infection ~0.1) and incubated with shaking at 32° C. until lysis (~90 min). The lysates were centrifuged (6,000 g) and filtered (0.2 μM) to remove cell debris. Streptavidin-coated magnetic beads were treated with biotinylated small molecule ligands for 30 min at 25° C. to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce nonspecific phage binding. Binding reactions were assembled by combining phage lysates, liganded affinity beads and test compounds in 1× binding buffer (20% SeaBlock, 0.17×PBS, 0.05% Tween 20, 6 mM DTT). Test compounds were prepared as 1,000× stocks in DMSO and rapidly diluted into the aqueous environment (0.1% DMSO final). DMSO (0.1%) was added to control assays lacking a test compound. All reactions were carried out in polystyrene 96-well plates that had been pretreated with blocking buffer in a final volume of 0.1 ml. The assay plates were incubated at 25° C. with shaking for 1 h, long enough for binding reactions to reach equilibrium, and the affinity beads were washed four times with wash buffer (1×PBS, 0.05% Tween 20, 1 mM DTT) to remove unbound phage. After the final wash, the beads were resuspended in elution buffer (1×PBS, 0.05% Tween 20, 2 mM nonbiotinylated affinity ligand) and incubated at 25° C. with shaking for 30 min. The phage titer in the eluates was measured by standard plaque assays or by quantitative PCR.

The compounds were tested at a single concentration of 10 μM. The results of this primary screening are reported as '% Ctrl', where lower numbers indicate stronger hits (Table 1). % Ctrl is calculated using the following equation:

$$\left( \frac{\text{test compound signal} - \text{positive control signal}}{\text{negative control signal} - \text{positive control signal}} \right) \times 100$$

Binding Constant Measurements

For selected compounds where single concentration results at 10 μM had shown % control <5, Kd values were determined.

The equilibrium binding equations yield the following expression for the binding constant for the interaction between the free test compound and the kinase (Kd(test)), assuming that the phage concentration is below Kd(test): Kd(test)=(K$_{d(probe)}$/(K$_{d(probe)}$+[Probe]))×[test]$_{1/2}$. K$_{d(probe)}$ is the binding constant for the interaction between the kinase and the immobilized ligand, [Probe] is the concentration of the immobilized ligand and [test]$_{1/2}$ is the concentration of the free test compound at the midpoint of the transition. If [Probe] is below K$_{d(probe)}$ the expression simplifies to K$_{d(test)}$=[test]$_{1/2}$. Under these conditions the binding constants measured for the interaction between kinases and test compounds (K$_{d(test)}$) are therefore independent of the affinity of the immobilized ligand for the kinase (K$_{d(probe)}$). T7 phage grow to a titer of 10$^8$-10 plaque forming units (PFU)/ml, and the concentration of phage-tagged kinase in the binding reaction is therefore in the low picomolar range. The concentration of the immobilized ligand is kept in the low nanomolar range, below its binding constant for the kinase. Binding data were fit to the equation PFU=L+((H−L)×(K$_{d(test)}$)/(K$_{d(test)}$+[test])), where L is the lower baseline, H is the upper baseline, K$_{d(test)}$ is the binding constant for the interaction between the test compound and the kinase, and [test] is the free test compound concentration. Binding constants measured in duplicate on the same day as part of the same experiment generally were within twofold. Duplicate measurements performed on separate days generally varied by no more than fourfold. Clustering and visualization was performed with Cluster 3.0 (M. Eisen, Stanford University) and Mapletree software (M. Eisen, Stanford University; L. Simirenko, Lawrence Berkeley National Lab). For kinase/compound combinations where no interaction was observed, the binding constant was arbitrarily set to 1 M.

TABLE 1

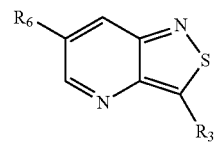

| Example | % Ctrl | Kd (μM) |
|---------|--------|---------|
| 4 | 68 | |
| 7 | 55 | |

TABLE 1-continued

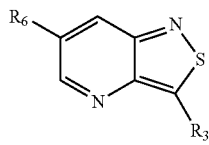

| Example | % Ctrl | Kd (µM) |
|---|---|---|
| 14 | 87 | |
| 23 | 0.8 | 0.5 |
| 24 | 11 | |
| 25 | 25 | |
| 26 | 0 | 0.052 |
| 27 | 0.1 | 0.042 |
| 31 | 18 | |
| 32 | 2.2 | |
| 33 | 9.4 | |
| 34 | 37 | |
| 28 | 45 | |
| 29 | 0.4 | 0.12 |
| 30 | 0.3 | 0.3 |
| 12 | 62 | |
| 11 | 50 | |
| 3 | 97 | |
| 14 | 100 | |
| 35 | 93 | |
| 36 | 19 | |
| 37 | 22 | |
| 6 | 70 | |
| 5 | 80 | |
| 39 | 88 | |
| 40 | 19 | |
| 38 | 76 | |
| 8 | 61 | |
| 41 | 7.4 | |
| 42 | 72 | |
| 43 | 0.05 | 0.047 |
| 44 | 0.7 | 0.13 |
| 45 | 6.3 | |
| 46 | 2.8 | 0.019 |
| 47 | 0 | 0.018 |
| 48 | 0.2 | 0.072 |
| 49 | 0 | 0.0083 |
| 50 | 0 | 0.0089 |
| 51 | 51 | |
| 52 | 0.15 | 0.2 |
| 53 | 9 | |
| 54 | 0.05 | 0.088 |
| 57 | 2.6 | 0.27 |
| 58 | 0.8 | 0.23 |
| 60 | 1.1 | 0.18 |
| 61 | 0.05 | 0.18 |
| 62 | 0 | 0.082 |
| 63 | 0.6 | 0.14 |
| 64 | 0 | 0.018 |
| 65 | 0 | 0.031 |
| 66 | 0.1 | 0.063 |
| 67 | 0.85 | 0.21 |
| 68 | 0.05 | 0.069 |
| 69 | 0.1 | 0.088 |
| 70 | 4 | 0.32 |
| 71 | 2.6 | 0.33 |
| 72 | 40 | |
| 73 | 0 | 0.1 |
| 74 | 81 | |
| 75 | 0.1 | 0.14 |
| 76 | 0 | 0.027 |
| 78 | 0.1 | 0.19 |
| 79 | 0.05 | 0.21 |
| 80 | 0.1 | 0.11 |
| 81 | 12 | |
| 82 | 0.15 | 0.26 |
| 83 | 0.05 | 0.052 |
| 84 | 0 | 0.14 |
| 85 | 31 | |
| 86 | 92 | |
| 87 | 4.3 | 0.33 |

Example 89

Antiviral HCV Assays

We have recently shown that GAK is a regulator of HCV entry and assembly and therefore represents a potential target for anti-HCV treatment (Neveu, G. et al. AAK1 and GAK regulate hepatitis C virus entry and are potential drug targets. *J. Virol.* 2015, 89, 4387-4404; Neveu, G. *PLoS Pathog.* 2012, 8(8), e1002845).

Moreover, erlotinib, an approved anticancer drug known to target GAK significantly inhibited binding of HCV core to AP2M1, HCV entry, and assembly. Nevertheless, while erlotinib binds GAK with a high affinity (Kd=3.4 nM), it binds EGFR, its primary anticancer target, with a comparable affinity (Kd=1 nM), and several other kinases (albeit at a lower affinity). The use of erlotinib as a chemical tool to probe the role of GAK in HCV infection is therefore somewhat limited, particularly, since EGFR has also been recognized as an essential host factor for HCV infection. Moreover, the limited selectivity contributes to erlotinib's side effects, which may reduce its potential as an antiviral agent, particularly in long duration regimens as those required for the treatment of HCV. We therefore hypothesized that since the isothiazolo[4,3-b]pyridines of example 49 and example 50 are structurally unrelated to erlotinib and lack anti-EGFR activity, they represent attractive chemical tools to study the role of GAK in HCV infection, and that their strong potency, promising selectivity profile and favorable drug-like properties make them a potential novel class of antiviral agents.

Figure 1:
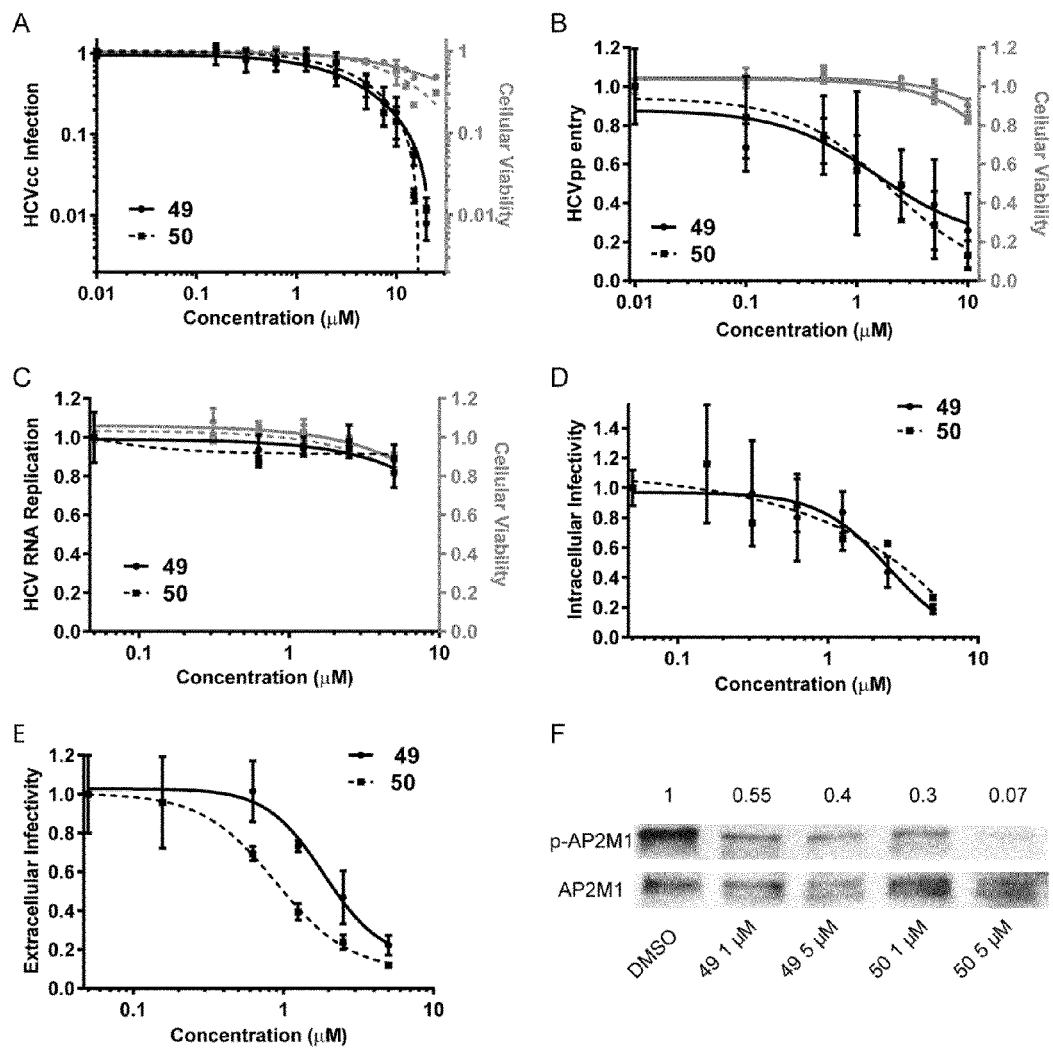
FIG. 1: Selective GAK inhibitors inhibit HCV infection and AP2M1 phosphorylation.

To further validate GAK as an antiviral target and determine the antiviral effect of these compounds on HCV infection, Huh-7.5 (human hepatoma) cells were infected with cell culture grown J6/JFH(p7-Rluc2A) HCV (HCVcc), a *Renilla* luciferase-containing reporter virus that replicates and produces high viral titers in Huh-7.5 cells. Infected cells were treated with various concentrations of the compounds of example 49, and example 50, or DMSO. Drug-containing media was replenished every 24 hours. Antiviral activity and cellular viability were measured by luciferase and alamarBlue-based assays, respectively, 72 hours postinfection. As shown in FIG. 1A, treatment with either 49 or 50 resulted in a dose-dependent inhibition of viral replication. Half maximal effective concentration ($EC_{50}$) values were 2.55±0.43 µM (p=0.0002) and 2.81±0.8 µM (p=0.009) for 49 and 50, respectively. The half maximal cytotoxic concentration ($CC_{50}$) values were 23.27±3.4 µM (p=0.000012) for 49 and 8.92±1.43 µM (p=0.000044) for 50.

Next, we sought to pinpoint the step of the viral lifecycle that is disrupted by these GAK inhibitors. To study the effect of the GAK inhibitors on HCV entry, we measured the entry of pseudoparticles of HCV (HCVpp) (lentiviral vectors that incorporate the HCV glycoproteins on the viral envelope) upon a 4 hour treatment with various concentrations of 49 and 50 using luciferase reporter-based assays. Huh-7.5 cells were infected with HCVpp for 1 hour on ice followed by a temperature shift to 37° C., 4 hour treatment with various concentrations of the compounds or DMSO, and medium replacement for removal of residual drugs and unbound virus. These compounds inhibited HCVpp entry in a dose-dependent manner, with half maximal effective concentrations ($EC_{50}$'s) of 3.6±1.2 µM (p=0.03) and 2.05±0.36 µM (p=0.0025), respectively, and a minimal effect on cellular viability (FIG. 1B).

To determine the effect of the compounds on later steps of the HCV lifecycle and distinguish between a defect in viral RNA replication, assembly and/or release, Huh-7.5 cells were electroporated with in vitro transcribed luciferase reporter J6/JFH(p7-Rluc2A) HCV RNA[24] and treated daily for 72 hours with either 49, 50 or DMSO. HCV RNA replication was measured by luciferase assays 72 hours postelectroporation and intra- and extra-cellular infectivity were measured by luciferase assays in naïve cells inoculated with either clarified cell lysates or supernatants derived from the electroporated cells, respectively. Treatment with 49 and 50 did not affect HCV RNA replication (FIG. 1C). Nevertheless, 49 and 50 demonstrated a dose-dependent effect on intracellular infectivity (FIG. 1D), with $EC_{50}$ values of 1.64±0.272 µM (p=0.009) and 2.43±0.72 µM (p=0.0281), respectively. Moreover, 49 and 50 significantly inhibited extracellular infectivity (FIG. 1E), with $EC_{50}$ values of 2.13±0.72 µM (p=0.04) and 2.47±0.9 µM (p=0.04), respectively. These data indicate that the two selective GAK inhibitors tested disrupt HCV assembly and infectious virus production without affecting HCV RNA replication.

Similar to small interfering RNAs (siRNAs) that target GAK as well as erlotinib, these compounds thus inhibit two temporally distinct steps in the HCV lifecycle: entry and assembly. The $EC_{50}$ values for the antiviral effect of these compounds range from ~1.5-3 µM, depending on the assay used. These $EC_{50}$ values are slightly higher or comparable to those of erlotinib (0.5-1.5 µM), likely reflecting the absence of EGFR inhibition exhibited by erlotinib.

Taken together, these results provide a pharmacological validation of the requirement for GAK in the regulation of HCV entry and assembly. Moreover, the selective GAK inhibitors represent candidate compounds to target two steps of the HCV lifecycle: viral entry and assembly. To validate the mechanism of action of these compounds, we studied their effect on AP2M1 phosphorylation. Huh-7.5 cells were treated with various concentrations of the compounds or DMSO. Since AP2M1 phosphorylation is transient (due to the activity of the phosphatase PP2A) to allow capturing of the phosphorylated AP2M1 state, these cells were incubated for 1 hour in the presence of the PP2A inhibitor, calyculin A prior to lysis. The ratio of phosphorylated AP2M1 (p-AP2M1) to total AP2M1 was measured by quantitating Western blot band intensity. p-AP2M1 to AP2M1 ratios were reduced by either 49 or 50 in a dose-dependent manner and were significantly lower than the ratios measured in the DMSO control (FIG. 1F). These results indicate that 49 and 50 modulate AP2M1 phosphorylation, as predicted for compounds that target GAK.

Materials and Methods

Plasmids pFL-J6/JFH(p7-Rluc2A) was a gift from Dr. C. M. Rice (*J. Virol.* 2007, 81, 10220-10231).

Plasmids used in the HCVpp entry assays (pNL4-3.Luc.R-E, pcDM8 and pcDM8-E1E2) were a gift from Dr. Shoshana Levy.

Cells

Huh-7.5 cells and 293T cells were grown in Dulbecco's modified Eagle medium (DMEM; Mediatech) supplemented with 10% fetal bovine serum (Omega Scientific), nonessential amino acids (Gibco), 1% L-glutamine (Gibco), and 1% penicillin-streptomycin (Gibco), and maintained in 5% $CO_2$ at 37° C.

In Vitro Transcription of Viral RNA, Transfection, and HCVcc Generation

HCV RNA was generated and delivered into Huh-7.5 cells, as previously described (*Science* 2005, 309, 623-626). Briefly, RNA was reverse transcribed from Xbal-linearized J6/JFH(p7-Rluc2A) template using the T7 MEGAscript kit according to the manufacturer's instructions (Ambion). Viral RNA was purified using the RNeasy kit (Qiagen). $6×10^6$ Huh7.5 cells were washed three times with ice-cold RNase-free PBS (BioWhittaker) and electroporated (0.82 kV, five 99 µs pulses) with 2 µg of viral RNA in a 2 mm-gap cuvette (BTX) using a BTX-830 electroporator. After a 15 min recovery at room temperature, cells were resuspended in pre-warmed growth medium and plated into 96 or 6-well culture plates. For HCVcc generation, cells were diluted in 30 ml of prewarmed growth medium and plated. Viral supernatants were collected daily from up to 5 passages of the electroporated cells, filtered through a 0.22 micron cellulose nitrate filter, and kept at –80° C. Viral titers were determined by limiting dilution and immunohistochemical staining using an antibody directed to core. 50% tissue culture infectious dose ($TCID_{50}$) was calculated, as described. Results are expressed as $TCID_{50}$/ml.

HCVcc Infection $6×10^3$ Huh-7.5 cells seeded in 96-well plates were infected in triplicates with HCVcc J6/JFH(p7-Rluc2A) at MOI (multiplicity of infection) of 0.1 in the presence of serial dilutions of the compounds. Culture medium was replaced daily with medium containing serial dilutions of the inhibitors. HCVcc infection was measured by standard luciferase assays at 72 hours postinfection, using a *Renilla* luciferase substrate and a Tecan luminometer (Tecan) according to the manufacturers' protocols. Alternatively, 4 hours postinfection, cells were washed and medium was replaced, followed by standard luciferase assays at 24 hours postinfection.

HCV RNA Replication by Luciferase Assays

HCV RNA replication was measured at 72 hours postelectroporation, as described (*PLoS Pathog.* 2012, 8(8), e1002845). Electroporated cells plated in quadruplicates in 96-well plates were washed twice with PBS and lysed with 30 µl of *Renilla* lysis buffer (Promega). Following 15 minute shaking at room temperature, luciferase activity was quantified by standard luciferase assays.

Extracellular and Intracellular Infectivity

Huh-7.5 cells electroporated with J6/JFH(p7-Rluc2A) RNA and plated in 6-well dishes were treated every 24 hours with GAK inhibitors for a total of 72 hours. For measurements of extracellular infectivity, supernatants were harvested, filtered using a 0.22-µm-pore size filter and used to infect naïve Huh-7.5 cells in triplicates. For intracellular infectivity measurements, electroporated cells were trypsinized, collected by centrifugation, resuspended in 500 µl medium, lysed by 4 freeze-thaw cycles, and pelleted at 3,650×g. Clarified supernatants were diluted in complete medium and used to inoculate naive Huh-7.5 cells in triplicates. At 72 hours postinfection cells were lysed and luciferase activity quantified as above.

HCVpp Production and Entry Assays

HCVpp (H77c strain, genotype 1a) were generated as described previously (*J. Exp. Med.* 2003, 197, 633-642). Briefly, 293T cells were transfected with a 1:1 ratio of plasmids encoding HIV provirus expressing luciferase and HCV E1E2 envelope glycoproteins. Supernatants were harvested 48 hours posttransfection and filtered. Huh-7.5 cells were infected with HCVpp and 8 mg/ml polybrene (Sigma) for 4 hours. Cell lysates were collected at 48 hours after HCVpp infection, and firefly luciferase (Promega) activity was measured using a Tecan luminometer (Tecan).

Viability Assay

Following treatment with GAK inhibitors, Huh-7.5 cells either infected with HCVcc and HCVpp or electroporated with HCV RNA were incubated for 2-4 hours with media supplemented with 10% AlamarBlue reagent (TREK Diagnostic Systems) at 37° C. Fluorescence at 560 nm was measured via FLEXstation II 384 (Molecular Devices, Inc.) as readout of cellular metabolic activity.

The Effect of the Compounds on AP2M1 Phosphorylation

Huh-7.5 cells were treated with various concentrations of the compounds or DMSO in serum free medium. To allow capturing of the phosphorylated AP2M1 state, 100 nM of the PP2A inhibitor calyculin A was added to all wells 30 min after drug administration. 1 hour later cells were lysed and samples subjected to SDS-PAGE and blotting with antibodies targeting AP2M1 (Santa Cruz Biotechnology) and p-AP2M1 (Cell Signaling).

Example 9

Antiviral Dengue Virus Assays

As shown in FIG. 2A, treatment with either cpd 49 or cpd 50 resulted in a dose-dependent inhibition of viral replication. Half maximal effective concentration (EC50) values were 0.8 µM and 2.6 µM for cpd 49 and cpd 50, respectively. These drugs had a minimal effect on cellular viability in the concentration range used, as measured by alamarBlue-based assays (FIG. 2B). Taken together, these data indicate that the two selective GAK inhibitors tested inhibit Dengue virus infection.

These results, taken together with the HCV results of example 89 and the mechanism of action of these compounds corroborate towards a broad-spectrum antiviral use of the compounds of the present invention.

Materials and Methods

Plasmids. pACYC Rluc2A TSV was a gift from Dr. Pei-Yong Shi (Zou, G et al. Antiviral Research, 2011).

Cell Cultures. Huh-7 and BHK cells were maintained in DMEM (Gibco) supplemented with 1% L-glutamine (Gibco), 1% penicillin, 1% streptomycin (Gibco), 1× non-essential amino acids (Gibco), and 10% fetal bovine serum (Omega Scientific).

In vitro transcription of viral RNA and viral production. RNA was reverse transcribed from ClaI-linearized pACYC Rluc2A TSV template using the T17 mMESSAGE mMACHINE kit according to the manufacturer's instructions (Ambion). Reactions were incubated for 2 hr at 37° C. followed by DNase treatment for 15 min at 37° C. Viral RNA was purified using the RNeasy kit (Qiagen). $6 \times 10^6$ BHK cells were washed three times with ice-cold RNase-free PBS (BioWhittaker) and electroporated (0.82 kV, five 99 µs pulses) with 2 µg of viral RNA in a 2 mm-gap cuvette (BTX) using a BTX-830 electroporator. After a 15 min recovery at room temperature, cells were resuspended in pre-warmed growth medium and plated in 10 cc dish. Cells were cultured and split every other day. Virus-containing supernatant was harvested prior to cell splitting up to day 10 post electroporation. Viral supernatants were pooled and filtered through 0.22-µm-pore size filter. Viral titers were determined by standard plaque assay on BHK cells.

Infection Studies. $6 \times 10^3$ Huh-7 cells were seeded in 96-well plates and infected at MOI of 0.1 with cell culture-grown DENV the next day. 30 minutes prior to infection and daily thereafter culture medium was replaced with medium containing serial dilutions of GAK inhibitors or DMSO control. At 72 hours postinfection, samples were subjected to viability assay, followed by luciferase assay. For luciferase assays cells were lysed with 30 µl of *Renilla* lysis buffer per well (Promega). Following 15 minute shaking at room temperature, luciferase activity was quantified using a *Renilla* luciferase substrate (Promega) and a Tecan luminometer (Tecan) according to the manufacturers' instructions.

Viability assay. Huh-7 cells infected and treated daily with GAK inhibitors for a total of 72 hours were incubated for 2-4 hours with media supplemented with 10% AlamarBlue reagent (TREK Diagnostic Systems) at 37° C. Fluorescence at 560 nm was measured via FLEXstation II 384 (Molecular Devices, Inc.) as readout of cellular metabolic activity.

Example 91

Antiviral Activity of GAK Inhibitors Against the SARS Coronavirus (Virus strain: Urbani; Cell line: Vero76)

Primary cytopathic effect (CPE) reduction assay. Four-concentration CPE inhibition assays are performed. Confluent or near-confluent cell culture monolayers in 96-well disposable microplates are prepared. Cells are maintained in MEM or DMEM supplemented with FBS as required for each cell line. For antiviral assays the same medium is used but with FBS reduced to 2% or less and supplemented with 50 µg/ml gentamicin. The test compound is prepared at four $\log_{10}$ final concentrations, usually 0.1, 1.0, 10, and 100 µg/ml or µM. The virus control and cell control wells are on every microplate. In parallel, a known active drug (M128533, a protease inhibitor) is tested as a positive control drug using the same method as is applied for test compounds. The positive control is tested with each test run. The assay is set up by first removing growth media from the 96-well plates of cells. Then the test compound is applied in 0.1 ml volume to wells at 2× concentration. Virus, normally at <100 50% cell culture infectious doses (CCID50) in 0.1 ml volume, is placed in those wells designated for virus infection. Medium devoid of virus is placed in toxicity control wells and cell control wells. Virus control wells are treated similarly with virus. Plates are incubated at 37° C. with 5% $CO_2$ until maximum CPE is observed in virus control wells. The plates are then stained with 0.011% neutral red for approximately two hours at 37° C. in a 5% $CO_2$ incubator. The neutral red medium is removed by complete aspiration, and the cells may be rinsed 1× with phosphate buffered solution (PBS) to remove residual dye. The PBS is completely removed and the incorporated neutral red is eluted with 50% Sorensen's citrate buffer/50% ethanol (pH 4.2) for at least 30 minutes. Neutral red dye penetrates into living cells, thus, the more intense the red color, the larger the number of viable cells present in the wells. The dye content in each well is quantified using a 96-well spectrophotometer at 540 nm wavelength. The dye content in each set of wells is converted to a percentage of dye present in untreated control wells using a Microsoft Excel computer-based spreadsheet. The 50% effective ($EC_{50}$, virus-inhibitory) concentrations and 50% cytotoxic ($CC_{50}$, cell-inhibitory) concentrations are then calculated by linear regression analysis. The quotient of $CC_{50}$ divided by $EC_{50}$ gives the selectivity index (SI) value.

| Example | Drug Assay | $EC_{50}$ (µg/ml) | $CC_{50}$ (µg/ml) | SI |
|---------|------------|-------------------|-------------------|-----|
| 49 | Visual | 1.2 | 34 | 28 |
| 49 | Neutral Red | 0.77 | 50 | 65 |
| 50 | Visual | 2.4 | 15 | 6.3 |
| 50 | Neutral Red | 3.2 | 13 | 4.1 |
| 64 | Visual | >0.42 | 0.42 | 0 |

-continued

| Example | Drug Assay | EC$_{50}$ (µg/ml) | CC$_{50}$ (µg/ml) | SI |
|---|---|---|---|---|
| 64 | Neutral Red | >0.97 | 0.97 | 0 |
| 76 | Visual | 0.86 | 18 | 21 |
| 76 | Neutral Red | 0.54 | 33 | 61 |
| 23 | Visual | 4.5 | 34 | 11 |
| 23 | Neutral Red | 4.4 | 50 | 11 |
| 52 | Visual | 44 | >100 | >2.3 |
| 52 | Neutral Red | 49 | >100 | >2.0 |
| 66 | Visual | 50 | >100 | >2.0 |
| 66 | Neutral Red | 38 | >100 | >2.6 |
| 74 | Visual | 4.5 | >100 | >22 |
| 74 | Neutral Red | 5.8 | >100 | >17 |

Example 92

Combinations of the Selective GAK Inhibitor of Example 50 ("50") with Sunitinib have a Synergistic Effect on Ebola Virus Entry Vero cells (African green monkey kidney cells) were pre-treated with the indicated drug combinations for 1 hour, followed by infection with VSV-EB GFP-reporter virus (VSV bearing surface glycoprotein of EBOV) at MOI of 1 for additional 3 hours in the presence of the drugs. Subsequently, the virus and drug containing media was removed, cells were washed once with PBS and fresh drug-free media replenished. At 20-24 hours following infection, cells were harvested by trypsinization, fixed with 1% PFA and analyzed by flow cytometry (BD LSRII instrument). Fraction of GFP positive cells out of total live cells in each population was calculated. Results for drug treated samples were normalized to vehicle control and represented as relative fractions of infected/GFP positive cells. Sunitinib was tested in the concentration range from 0 µM to 10 µM, while "50" was tested in the range from 0 µM to 20 µM. While sunitinib treatment alone resulted in a substantial dose-dependent reduction of VSV-EB infection, treatment with '50' resulted in minimal inhibition of infection in the concentration range tested. However, combination drug treatment displayed synergy of 150, with log volume of 26.34 as analyzed by MacSynergy. Importantly, no antagonism was detected by MacSynergy in the concentration range tested. The results are shown in FIG. 3.

Example 93

Screening of the GAK Inhibitors of Examples 49, 50, 64 and 76 Against Influenza A Virus H1N1, Pollovirus 3 and Yellow Fever Virus Viruses Used
Influenza A virus H1N1
  Virus strain: California/07/2009
  Cell line: MDCK
Poliovirus 3
  Virus strain: WM-3
  Cell line: Vero76
Yellow fever virus
  Virus strain: 17D
  Cell line: Vero76
Primary Cytopathic Effect (CPE) Reduction Assay.

Four-concentration CPE inhibition assays were performed. Confluent or near-confluent cell culture monolayers in 96-well disposable microplates were prepared. Cells were maintained in MEM or DMEM supplemented with FBS as required for each cell line. For antiviral assays the same medium was used but with FBS reduced to 2% or less and supplemented with 50 µg/ml gentamicin. The test compound was prepared at four log$_{10}$ final concentrations, usually 0.1, 1.0, 10, and 100 µg/ml or µM. The virus control and cell control wells were on every microplate. In parallel, a known active drug was tested as a positive control drug using the same method as was applied for test compounds. This drug was ribavirin for influenza, infergen for yellow fever viruses, Pirodavir for Polio viruses. The positive control was tested with each test run. The assay was set up by first removing growth media from the 96-well plates of cells. Then the test compound was applied in 0.1 ml volume to wells at 2× concentration. Virus, normally at <100 50% cell culture infectious doses (CCID50) in 0.1 ml volume, was placed in those wells designated for virus infection. Medium devoid of virus was placed in toxicity control wells and cell control wells. Virus control wells were treated similarly with virus. Plates were incubated at 37° C. with 5% CO$_2$ until maximum CPE was observed in virus control wells. The plates were then stained with 0.011% neutral red for approximately two hours at 37° C. in a 5% CO$_2$ incubator. The neutral red medium was removed by complete aspiration, and the cells were optionally rinsed 1× with phosphate buffered solution (PBS) to remove residual dye. The PBS was completely removed and the incorporated neutral red was eluted with 50% Sorensen's citrate buffer/50% ethanol (pH 4.2) for at least 30 minutes. Neutral red dye penetrates into living cells, thus, the more intense the red color, the larger the number of viable cells present in the wells. The dye content in each well was quantified using a 96-well spectrophotometer at 540 nm wavelength. The dye content in each set of wells was converted to a percentage of dye present in untreated control wells using a Microsoft Excel computer-based spreadsheet. The 50% effective (EC$_{50}$, virus-inhibitory) concentrations and 50% cytotoxic (CC$_{50}$, cell-inhibitory) concentrations were then calculated by linear regression analysis. The quotient of CC$_{50}$ divided by EC$_{50}$ gives the selectivity index (SI) value. The majority of the compounds tested, were found to generate EC$_{50}$ values of 30 µg/ml or below in the antiviral assays against influenza, yellow fever viruses, and Polio viruses and an SI value of 3 or more.

The invention claimed is:

1. A method of treatment of a viral infection in an animal, mammal or human, comprising administration of a therapeutically effective amount of an isothiazolo[4,3-b)] pyridine derivative according to formula I, and/or a pharmaceutical acceptable addition salt thereof and/or a stereoisomer thereof and/or a solvate thereof, wherein
  R$_3$ is selected from the group consisting of halogen, amino, morpholinyl, thiomorpholinyl, pyrrolidinyl, piperazinyl, homopiperazinyl, piperidinyl, (mono- or di-) C$_{1-12}$ alkylamino, (mono- or di-) C$_{2-12}$ alkenylamino, (mono- or di-) C$_{2-12}$ alkynylamino, monoarylamino; diarylamino; (mono- or di-) C$_{3-10}$ cycloalkylamino, $C_{3-10}$ cycloalkyl$C_{1-4}$ alkylamino, (mono- or di-) $C_{3-10}$ cycloalkenylamino, (mono- or di-) hydroxy $C_{1-7}$ alkylamino, (mono- or di-) $C_{1-4}$ alkylarylamino, (mono- or di-) aryl$C_{1-4}$ alkylamino, mercapto $C_{1-7}$ alkyl, $C_{1-7}$ alkoxy, $C_{1-4}$ alkylamino, alkoxyaryl, $C_{3-10}$ cycloalkoxy, heterocyclic-substituted alkylamino, heterocyclic-substituted aryl amino, heterocyclic amino, hydroxy-alkylamino, mercaptoalkylamino, hydroxypiperidinyl, aryl and heteroaryl groups, and, wherein said morpholinyl, thiomorpholinyl, pyrrolidinyl, piperazinyl, piperidinyl, heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, and, wherein one or more carbon atoms in any ring group may be replaced with —C(=O)—;

$R_6$ is selected from the group consisting of halogen, heteroaryl and aryl groups, wherein said heteroaryl or aryl groups are optionally substituted with one or more substituents selected from the group consisting of halogen, $C_{1-7}$ alkyl, $C_{2-7}$ alkenyl, $C_{2-7}$ alkynyl, halo $C_{1-7}$ alkyl, nitro, hydroxyl, sulfhydryl, amino, $C_{1-7}$ alkoxy, $C_{3-10}$ cycloalkoxy, aryloxy, arylalkyloxy, oxyheterocyclic, heterocyclic-substituted alkyloxy, thio $C_{1-7}$ alkyl, thio $C_{3-10}$ cycloalkyl, thioaryl, thio-heterocyclic, arylalkylthio, heterocyclic-substituted alkylthio, formyl, carbamoyl, thiocarbamoyl, ureido, thioureido, sulfonamido, hydroxylamino, alkoxy-amino, mercaptoamino, thioalkylamino, acylamino, thioacylamino, cyano, carboxylic acid or esters or thioesters or halides or anhydrides or amides thereof, thiocarboxylic acid or esters or thioesters or halides or anhydrides or amides thereof, alkylamino, cycloalkylamino, alkenylamino, cycloalkenylamino, alkynylamino, arylamino, arylalkylamino, hydroxyalkylamino, mercaptoalkylamino, heterocyclic amino.

2. The method according to claim 1, wherein said viral infection is an infection with an RNA-virus.

3. The method according to claim 1, wherein said viral infection is a Retroviral or a Flaviviral infection.

4. The method according to claim 1, wherein said viral infection is a HIV-1 infection, a HIV-2 infection, a HCV infection, a Dengue virus infection or an infection with a Flavivirus other than HCV and Dengue virus.

* * * * *